(12) United States Patent
Darnell

(10) Patent No.: US 8,193,313 B2
(45) Date of Patent: Jun. 5, 2012

(54) METHODS AND COMPOSITIONS FOR TUMOR VACCINATION AND THERAPY

(75) Inventor: Robert B. Darnell, New York, NY (US)

(73) Assignee: The Rockefeller University, New York, NY (US)

(*) Notice: Subject to any disclaimer, the term of this patent is extended or adjusted under 35 U.S.C. 154(b) by 0 days.

(21) Appl. No.: 13/046,875

(22) Filed: Mar. 14, 2011

(65) Prior Publication Data

US 2011/0280896 A1    Nov. 17, 2011

Related U.S. Application Data

(62) Division of application No. 12/168,629, filed on Jul. 7, 2008, now Pat. No. 7,928,190.

(60) Provisional application No. 60/958,497, filed on Jul. 5, 2007.

(51) Int. Cl.
*A61K 38/08* (2006.01)

(52) U.S. Cl. .................................................... 530/328

(58) Field of Classification Search .................. 530/328
See application file for complete search history.

(56) References Cited

U.S. PATENT DOCUMENTS 6,750,029 B1    6/2004    Darnell et al.
7,928,190 B2    4/2011    Darnell et al.

FOREIGN PATENT DOCUMENTS

CA         2387391 A1 * 11/2002

* cited by examiner

*Primary Examiner* — Misook Yu
*Assistant Examiner* — Brad Duffy
(74) *Attorney, Agent, or Firm* — Fox Rothschild LLP; Gerard P. Norton

(57) ABSTRACT

The present invention relates to peptide vaccines, pharmaceutical compositions thereof, and associated methodologies that promote the immune-mediated regression of tumors expressing an onconeural antigen, e.g. a cdr-2 antigen, HuD antigen. The cancer peptide vaccines of the present invention are antigenic peptides capable of being faithfully presented on the MHC I complex of a target cell or antigen presenting cell. This external cellular presentation of these peptides promotes a specific cytotoxic T lymphocyte (CTL)-mediated immune response against tumor cells expressing these proteins, thereby, inducing immunological reactivity.

3 Claims, 20 Drawing Sheets

ATG GAC AAG ATT CTG ACA GCA TCA TTT TTA CTC CTA GGC CTT CAC CTA GCT
 M   D   K   I   L   T   A   S   F   L   L   L   G   L   H   L   A

GGG GTG AAT GGC CAG CAG AAG GAG AAA CAT GAC CAG CAG CAG GTG ACA CAA
 G   V   N   G   Q   Q   K   E   K   H   D   Q   Q   Q   V   R   Q

AGT CCC CAA TCT CTG ACA GTC TGG GAA GGA GGA ACC ACA GTT CTG ACC TGC
 S   P   Q   S   L   T   V   W   E   G   G   T   T   V   L   T   C

AGT TAT GAG GAC AGC ACT TTT AAC TAC TTC CCA TGG TAC CAA CAG TTC CCT
 S   Y   E   D   S   T   F   N   Y   F   P   W   Y   Q   Q   F   P

GGG GAA GGC CCT GCA CTT CTG ATA TCC ATA CTT TCA GTG TCC GAT AAA AAG
 G   E   G   P   A   L   L   I   S   I   L   S   V   S   D   K   K

GAA GAT GGA CGA TTC ACA ACC TTC TTC AAT AAA AGG GAG AAA AAG CTC TCC
 E   D   G   R   F   T   T   F   F   N   K   R   E   K   K   L   S

TTG CAC ATC ATA GAC TCT CAG CCT GGA GAC TCA GCC ACC TAC TTC TGT GCA
 L   H   I   I   D   S   Q   P   G   D   S   A   T   Y   F   C   <u>A</u>

GCA AGT CGG GCT TCT GGA GGA AGC AAT GCA AAG CTA ACC TTC GGG AAA GGC
 <u>A   S   G   A   S   G   G   S   N   A   K   L   T   F   G   K   G</u>

ACT AAA CTC TCT GTT AAA TCA AAC ATC CAG AAC CCA GAA CCT GCT GTG TAC
 T   K   L   S   V   K   S   N   I   Q   N   P   E   P   A   V   Y

```
CAG TTA AAA GAT CCT CGG TCT CAG GAC AGC ACC CTC TGC CTG TTC ACC GAC
 Q   L   K   D   P   R   S   Q   D   S   T   L   C   L   F   T   D

TTT GAC TCC CAA ATC AAT GTG CCG AAA ACC ATG GAA TCT GGA ACG TTC ATC
 F   D   S   Q   I   N   V   P   K   T   M   E   S   G   T   F   I

ACT GAC AAA ACT GTG CTG GAC ATG AAA GCT ATG GAT TCC AAG AGC AAT GGG
 T   D   K   T   V   L   D   M   K   A   M   D   S   K   S   N   G

GCC ATT GCC TGG AGC AAC CAG ACA AGC TTC ACC TGC CAA GAT ATC TTC AAA
 A   I   A   W   S   N   Q   T   S   F   T   C   Q   D   I   F   K

GAG ACC AAC GCC ACC TAC CCC AGT TCA GAC GTT CCC TGT GAT GCC ACG TTG
 E   T   N   A   T   Y   P   S   S   D   V   P   C   D   A   T   L

ACT GAG AAA AGC TTT GAA ACA GAT ATG AAC CTA AAC TTT CAA AAC CTG TCA
 T   E   K   S   F   E   T   D   M   N   L   N   F   Q   N   L   S

GTT ATG GGA CTC CGA ATC CTC CTG CTG AAA GTA GCC GGA TTT AAC CTG CTC
 V   M   G   L   R   I   L   L   L   K   V   A   G   F   N   L   L

ATG ACG CTG AGG CTG TGG TCC AGT
 M   T   L   R   L   W   S   S
```

FIG. 5A

```
ATG TCT AAC ACT GTC CTC GCT GAT TCT GCC TGG GGC ATC ACC CTG CTA TCT
 M   S   N   T   V   L   A   D   S   A   W   G   I   T   L   L   S

TGG GTT ACT GTC TTT CTC TTG GGA ACA AGT TCA GCA GAT TCT GGG GTT GTC
 W   V   T   V   F   L   L   G   T   S   S   A   D   S   G   V   V

CAG TCT CCA AGA CAC ATA ATC AAA GAA AAG GGA GGA AGG TCC GTT CTG ACG
 Q   S   P   R   H   I   I   K   E   K   G   G   R   S   V   L   T

TGT ATT CCC ATC TCT GGA CAT AGC AAT GTG GTC TGG TAC CAG CAG ACT CTG
 C   I   P   I   S   G   H   S   N   V   V   W   Y   Q   Q   T   L

GGG AAC CAA TTA AAC TTC CTT ATT CAG CAT TAT CAA AAC CTC GAG AGA GAC
 G   K   E   L   K   F   L   I   Q   H   Y   E   K   V   E   R   D

AAA GGA TTC CTA CCC AGC AGA TTC TCA GTC CAA CAG TTT GAT GAC TAT CAC
 K   G   F   L   P   S   R   F   S   V   Q   Q   P   D   D   Y   H

TCT GAA ATG AAC ATG AGT GCC TTG GAA CTG GAG GAC TCT GCT ATG TAC TTC
 S   E   M   N   M   S   A   L   E   L   E   D   S   A   M   Y   F

TGT GCC AGC TCT CTC GGA GGA TGG GCT GAG CAG TTC TTC GGA CCA GGG ACA
 C   A   S   S   L   G   G   W   A   E   Q   F   F   G   P   G   T

CGA CTC ACC GTC CTA GAG GAT CTG AGA AAT GTG ACT CCA CCC AAG GTC TCC
 R   L   T   V   L   E   D   L   R   N   V   T   P   P   K   V   S

TTG TTT GAG CCA TCA AAA GCA GAG ATT GCA AAC AAA CAA AAG GCT ACC CTC
 L   F   E   P   S   K   A   E   I   A   N   K   Q   K   A   T   L

GTG TGC TTG GCC AGG GGC TTC TTC CCT GAC CAC GTG GAG CTG AGC TGG TGG
 V   C   L   A   R   G   F   F   P   D   H   V   E   L   S   W   W

GTG AAT GGC AAG GAG GTC CAC AGT GGG GTC AGC ACG GAC CCT CAG GCC TAC
 V   N   G   K   E   V   H   S   G   V   S   T   D   P   Q   A   Y

AAG GAG AGC AAT TAT AGC TAC TGC CTG AGC AGC CGC CTG AGG GTC TCT GCT
 K   E   S   N   Y   S   Y   C   L   S   S   R   L   R   V   S   A

ACC TTC TGG CAC AAT CCT CGA AAC CAC TTC CGC TGC CAA GTG CAG TTC CAT
 T   F   W   H   N   P   R   N   H   F   R   C   Q   V   Q   F   H

GGG CTT TCA GAG GAG GAC AAG TCG CCA GAG GGC TCA CCC AAA CCT GTC ACA
 G   L   S   E   E   D   K   W   P   E   G   S   P   K   P   V   T

CAG AAC ATC AGT GCA GAG GCC TGG GGC CGA GCA GAC TGT GGA ATC ACT TCA
 Q   N   I   S   A   E   A   W   G   R   A   D   C   G   I   T   S

GCA TCC TAT CAT CAG GGG GTT CTG TCT GCA ACC ATC CTC TAT GAG ATC CTA
 A   S   Y   H   Q   G   V   L   S   A   T   I   L   Y   E   I   L

CTG GGG AAG GCC ACC CTA TAT GCT GTG CTG GTC AGT GGC CTG GTG CTG ATG
 L   G   K   A   T   L   Y   A   V   L   V   S   G   L   V   L   M

GCC ATG GTC AAG AAA AAA AAT TCC TGA
 A   M   V   K   K   K   N   S   *
```

FIG. 5B

D

FIG. 6D

METHODS AND COMPOSITIONS FOR TUMOR VACCINATION AND THERAPY

CROSS REFERENCE TO RELATED PATENT APPLICATION

The present application is a divisional patent application of U.S. patent application Ser. No. 12/168,629 filed on Jul. 7, 2008 now U.S. Pat. No. 7,928,190, which claims priority from Provisional U.S. Patent Application Ser. No. 60/958,497 entitled "Methods and Compositions for Tumor Vaccination and Therapy," which was filed on Jul. 5, 2007.

STATEMENT REGARDING FEDERALLY SPONSORED RESEARCH OR DEVELOPMENT

The invention described herein was supported in whole or in part by grants from The National Institute of Health (Grant Nos. R01 CA85784, M01-RR00102, and GM07739). The government has certain rights in the invention.

FIELD OF INVENTION

The present invention relates to peptide vaccines, pharmaceutical compositions thereof, and associated methodologies that promote the immune-mediated regression of tumors expressing an onconeural antigen, e.g. a cdr-2 antigen or HuD antigen. The cancer peptide vaccines of the present invention are antigenic peptides capable of being faithfully presented on the MHC I complex of a target cell or antigen presenting cell. This external cellular presentation of the onconeural peptide promotes a specific cytotoxic T lymphocyte (CTL)-mediated immune response against tumor cells expressing these proteins, thereby, inducing immunological reactivity.

BACKGROUND OF THE INVENTION

Cancer remains one of the leading causes of death among humans worldwide. Current treatment methods often involve chemotherapy, surgery and/or radiation therapy. These mechanisms, while effective in short term treatment, are often accompanied by harsh side effects and offer little guarantee of preventing future relapses. In light of these problems, other long-term strategies for treating cancer have been researched.

One such strategy involves the use of exogenous mechanisms to stimulate a patient's immune system to target the aberrant cancer cells. Rosenberg, S. A. *Nature.* 411 380-384 (2001); Dudley, et al. *Nat Rev Cancer.* 3 666-675 (2003); Boon, et al. *Annu Rev Immunol.* 24 175-208 (2006). More specifically, tumor cells are understood in the art to display unique proteins on their cell surface that may act as antigens. Such antigens are most often comprised of epitopes or small peptide sequences within the antigen that, when recognized by the host's immune system, generate an immunological response. Such an immunological response occurs when the antigenic protein is engulfed and degraded within an antigen presenting cell through intracellular proteolytic breakdown. Peptide fragments, i.e. epitopes, are then associated with immunity stimulating molecules of the Major Histocompatibility Complex (MHC), often in the endoplasmic reticulum of the cell and transported to the cell surface for extracellular presentation and immunological stimulation. With respect to cancer cells, peptide antigens are often associated with class I MHC molecules and presented on the cell surface of the cancer cell.

The MHC class I molecule is a tetramer comprised of an alpha and a beta chain. The alpha chain has three polymorphic domains, $\alpha_1$, $\alpha_2$, $\alpha_3$ wherein the degraded antigen binds within clefts formed therebetween. Because one MHC molecule can bind numerous antigens, each molecule is named according to its locus within the Human Leukocyte Antigen (HLA) region of the genome. More specifically, HLA-A, HLA-B, and HLA-C each refer to different loci wherein superfamilies of Class I MHC molecules are encoded, and HLA-DP, HLA-DQ, and HLA-DR each refer to different loci where Class II MHC molecules are encoded. Once the appropriate MHC molecule is bound to the antigen and the complex is transported to the cell surface, the cell is then in a condition for recognition by, for example, a lymphocyte.

T lymphocytes (T cells), among many functions, recognize antigens or immunodominant epitopes that are associated with alleles of the human leukocyte antigens (HLA). There are at least two distinct types of T lymphocytes: CD4+ helper T lymphocytes (TH cells) and CD8+ cytotoxic T lymphocytes (CTLs). TH cells are involved in both humoral and cell-mediated forms of immune responses and typically, though not exclusively, recognize antigens in association with class II MHC molecules. CTLs, however, recognize and destroy cells which display foreign antigens on their surfaces wherein the antigens are typically associated with class I MHC molecules. The CTL's recognition of such foreign antigens occurs through a T cell receptor (TCR) located on the surface of the CTL.

A TCR is a immunoglobin protein that may be comprised of at least an alpha chain with a variable region and a constant region, a beta chain with a variable region and a constant region, and a transmembrane region. The variable region of the alpha chain may by comprised of at least three complementarity determining regions (cdr1, cdr2, and cdr3, respectively) and the variable region of the beta chain may be comprised of at least four complementarity determining regions (cdr1, cdr2, cdr3, and cdr4, respectively). While all three cdr regions of the alpha chain and all four cdr regions of the beta chain function to facilitate recognition of an antigen/MHC complex, the cdr3 is the most variable and plays a large role in determining which epitopes and antigen/MHC complex(es) the TCR will recognize. Recognition of an antigen/MHC complex by the TCR triggers a cascade of protein and cytokine interactions leading to, among other interactions, the activation, maturation and proliferation of the precursor CTLs and resulting in CTL clones capable of destroying the cells exhibiting the antigens recognized as foreign.

Paraneoplastic neurologic disorders (PND) are autoimmune disorders caused by an onconeural antigen eliciting such a CTL mediated response. More specifically, cerebellar degeneration-related 2 protein (cdr2 protein) is one such onconeural protein normally expressed within immunoprivileged sites of the cerebellar Purkinje neurons in the brain, some brainstem neurons, and spermatogonia. Corradi, et al. *J Neurosci.* 17 1406-1415 (1997). However, research into paraneoplastic cereballar degeneration (PCD), a PND disorder wherein the patient's immune system destroys Purkinje neurons in the cerebellar cortex of the brain, revealed that the cdr2 protein is not limited to these cell types and may also be found within some gynecological tumor cells. (FIG. 1 in Corradi, et al. *J Neurosci.* 17 1406-1415 (1997)). Current research further suggests that the autoimmune effects of PCD are actually caused by cdr2-specific CTLs stimulated by the cdr2-expressing gynecologic carcinomas. Albert, et al. *Nat. Med.* 4 1321-1324 (1998). In other words, cdr2-specific CTLs within the PCD patient, while competent to elicit an immunological response to the cdr2 expressing tumor cells, secondarily recognize and elicit an autoimmune response to the cdr2 expressing Purkinje cells. Accordingly, the epitopes of the cdr2 proteins are, in fact, onconeural antigens in that they signal the presence of a carcinoma, but also elicit an autoimmune response to neural cells.

Another such onconeural antigen is an antigen of the Hu protein family. The Hu protein family, also normally expressed exclusively in neurons, has been linked as a intracellular antigen associated with small cell lung cancers (SCLC). Darnell, et al. *J Neurosci.* 11 1224-1230, Darnell, et al. *Proc Natl Acad Sci USA* 93 4529-4536. It is believed that HuD expression by tumor cells exposes the antigen to the immune system, generating an HuD-specific and CTL driven immune response. This results in appropriate and partially effective tumor immunity against the SCLC. Darnell et al. *N Engl J Med.* 349 1543-1554, Darnell et al. *Semin Oncol* 33 170-298. However, many Hu patients typically first present to clinicians with neurological symptoms triggered when this CTL driven tumor immune response, by unknown means, becomes competent to attack the nervous system, i.e. HuD expressing neurons.

There are, however, large populations of individuals with similar onconeural antigen expressing tumors who do not develop a PND. Darnell et al. *Cancer Res.* 60 2136-2139 (2000), Dalmau et al. *Ann Neurol* 27 544-552. Such populations suggest that antigen directed immunotherapy may be possible without the risk of developing PND, but only if the appropriate epitopes can be established. In fact, ~20% of SLCL patients develop immune responses to the Hu antigen that correlate with improved clinical outcome, in the absence any signs of neurologic PND symptoms Graus, F. et al. *J. Clin. Oncol.* 15, 2866-2872 (1997); Dalmau, J., Furneaux, H. M., Gralla, R. J., Kris, M. G. & Posner, J. B. *Ann. Neurol.* 27, 544-552 (1990). In particular, strategies that might target a peripheral tumor, but that are not able to either get across the blood-brain barrier or are otherwise incompetent to attack neurons, may target tumor cells without inducing autoimmune disease. However, exactly which onconeural antigens are optimally recognized by a CTL, and which corresponding TCRs are present on those T cells were previously unknown.

Based on the foregoing, there is a need in the art for compositions and methods providing therapeutic avenues of treatment for subjects suffering from onconeural antigen expressing tumors and/or a PND. The present invention addresses and meets this need by providing a series of HLA allele-specific, immunodominant peptides as disclosed that elicit an immune response to the carcinoma with little to no autoimmue side-effect. Moreover, this invention addresses these needs by identifying TCRs able to recognize these HLA-peptide complexes present on tumor cells, and demonstrates that they are sufficient to induce killing in an otherwise naïve CTL.

SUMMARY OF THE INVENTION

The present invention relates to peptide vaccines, and pharmaceutical compositions thereof, which promote the immune-mediated regression of tumors expressing an onconeural protein, e.g. a cdr-2 antigen or HuD antigen. The cancer peptide vaccines of the present invention are antigenic peptides capable of being faithfully presented on the MHC I complex of a target cell or antigen presenting cell. This external cellular presentation of the peptides promotes a specific cytotoxic T lymphocyte (CTL)-mediated immune response against tumor cells expressing these onconeural proteins. To this end, the present invention relates to the cdr2 and HuD specific peptide antigens disclosed herein, as well as peptide variants or homologs that generate a substantially similar therapeutic immune response when compared to the disclosed antigenic peptide. These specific cdr2 and HuD peptides may be administered through various vaccination strategies to directly promote a specific and thereapeutically relevant immune response against an onconeural antigen expressing tumor via stimulation of tumor specific CD8+ cytotoxic T lymphocytes. In one embodiment, the cdr2 or HuD epitope may bind to an HLA-A*0201 allele. In another embodiment, the cdr2 or HuD epitop may bind to an HLA-A*0301 allele. However, the present invention is not limited to these embodiments and the targeted MHC molecule may be comprised of any HLA allele that binds a cdr2 or HuD peptide disclosed herein, including but not limited to HLA-A*0101, HLA-A*1101, HLA-A*2402, HLA-B*0702, HLA-B*0801, and HLA-A*1501 or any allele within the HLA-A*01 superfamily, HLA-A*02 superfamily, HLA-A*03 superfamily, HLA-A*11 superfamily, HLA-A*24 superfamily, HLA-B*7 superfamily, HLA-B*8 superfamily, HLA-B*27 superfamily, or any other superfamily of an HLA allele that is understood in the art to bind a cdr2 or HuD peptide.

The present invention further relates to pharmaceutically acceptable compositions comprising one or more of the HLA allele specific cdr2 and HuD peptides disclosed herein. Upon appropriate administration to a subject, such a composition will provide for optimal in vivo presentation of a respective cdr2 or HuD peptide(s) so as to promote a specific CTL-mediated immune response against an onconeural gene expressing tumor. These compositions may include, but are not limited to, (i) one or more cdr2 peptides as disclosed herein, (ii) one or more HuD peptide as disclosed herein, or (iii) a polypeptide comprising an amino acid sequence of more than one epitope disclosed herein, so as to provide an opportunity to present multiple epitopes within a single polypeptide. Alternatively, a composition of the present invention may comprise a nucleic acid molecule, such as in the form of RNA, viral or plasmid DNA vector construct, which encodes and effectively presents at least one epitopic sequence disclosed herein, up to and including a nucleic acid molecule which encodes the entire coding region or multiple epitopes of a cdr2 protein or an HuD protein. Any such immunogenic composition may be delivered to any antigen presenting cell by any means discussed herein or any means known in the art.

In a further embodiment of the present invention, the immunogenic composition is provided comprising at least one isolated onconeural peptide wherein the peptide binds to MHC complex and elicits an immune response through a T cell receptor on the surface of a T lymphocyte. A composition may comprise a cdr2 peptide comprising of SEQ ID NO: 1. However, the cdr2 peptide is not limited to this embodiment and may be comprised of any human or non-human cdr2 peptide sequence within the cdr2 protein SEQ ID NO: 145 including, but not limited to SEQ ID NO: 1-SEQ ID NO: 41 and SEQ ID NO: 54-SEQ ID NO: 144.

In an alternative embodiment, the immunogenic composition may alternatively comprise a HuD peptide comprising SEQ ID NO: 146 or SEQ ID NO: 147.

In further embodiments, the immunogenic composition may optionally be comprised of an immune stimulating and/or neurological disease preventing adjuvant.

The present invention further relates to in vivo methods of anti-tumor vaccination with a pharmaceutically effective immunogenic composition which comprises delivery to or contacting an antigen presenting cell with a peptide antigen disclosed herein under conditions that induce a specific CTL-mediated immune response against the onconeural antigen expressing cells of the tumor. These methods may employ various techniques known in the art, including but not limited to (i) antigen loading of dendritic cells with one or more cdr2 or HuD specific peptides, polypeptides or nucleic acid molecules encoding such peptides as disclosed herein; and/or, (ii) local injection of one or more cdr2 or HuD specific peptides, polypeptides or nucleic acid molecules encoding such peptides as disclosed herein so as to promote delivery of the peptide, polypeptide or nucleic acid vector to an appropriate antigen presenting cell, such as a dentritic cell. These targeted dendritic cells then migrate to secondary lymphoid tissues where they present the respective antigen epitopes to T cells to induce an cytolytic T cell response against the onconeural antigen-expressing tumor cells.

The present invention also relates to methods of promoting regression of an onconeural antigen expressing tumor through adoptive T cell therapy. Various adoptive T cell therapeutic strategies are contemplated in light of the present disclosure. For example, peripheral blood lymphocytes may be acquired and stimulated in vitro with a peptide disclosed herein so as to elicit cdr2-specific or HuD-specific CD8+ T cells. These antigen specific T cells may be subsequently administered to the subject to promote an effective cell mediated immune response against a target tumor, e.g. a gynecological tumor, SCLC, etc. Additionally, antigen-specific CTL clones may be identified which exhibit high binding affinity and functional avidity to a specific cdr2 peptide or HuD peptide. A clonal cell line may be established to serve as a source to isolate and characterize the gene encoding the TCR αβ heterodimer. These nucleic acid molecules may be used to transduce a population of peripheral blood lymphocytes for use in adoptive transfer-based treatments. Thus, one embodiment of the present invention relates to an ex vivo method of treating a onconeural antigen expressing tumor which comprises obtaining a population of T-cells, such as human autologous T-cells, and transfecting these T-cells with genes encoding specific alpha- and beta-T-cell receptor subunits which show high affinity towards a respective cdr2 or HuD peptide. This population of transfected T-cells may be cultured and subsequently administered to a patient so as to promote a specific immune response against cdr2 or HuD expressing tumor cells. The alpha and beta TCR genes may encode a TCR from a mammalian source, including but not limited to a murine or human source, so long as any such TCR exhibits high specificity and affinity for the respective cdr2 or HuD peptide sequence. Thus, methods are disclosed herein for treating a onconeural-expressing cancer in a subject by inducing an immune response comprising engineering a T cell to express the TCR and administering to the subject an engineered T cell of the present invention to target or recognize an APC presenting a cdr2/MHC antigen complex or a HuD/MHC antigen complex, thereby treating a onconeural antigen-expressing cancer in a subject. The cdr2-expressing cancer cells may be a breast carcinoma, a cervical carcinoma, an ovarian carcinoma, a prostatic adenocarcinoma, a gastric adenocarcinoma, a fallopian tube adenocarcinoma, an esophageal adenocarcinoma, an addometrial carcinoma, a transitional cell carcinoma of the bladder or any other type of cdr2 expressing carcinoma known in the art. The HuD-expressing carcinomas may be any form of a small cell lung cancer or oat cell carcinoma known in the art.

The present invention further relates to an isolated nucleic acid molecule that encodes a mammalian TCR, wherein the TCR recognizes a MHC molecule associated with at least one onconeural antigen. One embodiment of this portion of the invention relates to a nucleic acid molecule encoding a cdr2-specific murine form of the alpha SEQ ID NO: 44 and beta (SEQ ID NO: 50) chains of the TCR. To this end, this portion of the invention also relates to isolated polypeptides which encode the exemplified murine form of the alpha (SEQ ID NO: 47) and beta (SEQ ID NO: 53) forms of the TCR.

In another embodiment, the present invention provides a method of detecting a presence of a PND and/or an onconeural antigen expressing carcinoma within a subject, comprising the step of detecting a presence in the subject of a T cell receptor (TCR) that recognizes an MHC molecule associated with a onconeural peptide. As noted above, detection of the onconeural antigen in accordance with the foregoing method leads to the diagnosis of an onconeural antigen expressing carcinoma within the patient. In specific embodiments, the foregoing method of detection may be used to detect the presence of SCLC or a gynecological tumor. More specifically, with respect to gynecological tumors, the present invention may be used to detect the presence of breast or ovarian cancers. Finally, for those patients exhibiting symptoms associated with a PND, the present method may also be used as a diagnostic tool for PND detection.

In a further embodiment, the present invention provides a method of detecting a presence of a PND and/or an onconeural antigen expressing carcinoma within a subject, comprising the step of detecting an epitope associated with the onconeural antigenic protein. As discussed further herein, the peptides of the present invention present potential epitopes associated with a onconeural antigenic protein. To this end, these epitopes are expressed in both the onconeural antigen expressing carcinomas and the neural cells associated with PND. Detection of the onconeural epitope in accordance with the foregoing method leads to the diagnosis of an onconeural antigen expressing carcinoma within the patient as well as diagnosis of PND, where applicable.

In another embodiment, the present invention provides a method of treating a PND and/or onconeural antigen expressing carcinoma in a subject, comprising the step of administering to the subject a tolerogenic composition. The tolerogenic composition may be comprised of a cdr2 peptide or HuD peptide and/or an engineered T cell adapted to recognize either the cdr2 peptide or HuD peptide in conjunction with a class I MHC molecule. Administration of the tolerogenic composition to the subject acts to regress the onconeural antigen carcinoma, specifically, those associated with cdr2 or HuD antigens, e.g. gynecological tumors or SCLC. Moreover, the foregoing method of treating a the carcinoma utilizes epitopes that stimulate an immunological response to the carcinoma cell population, while reducing the autoimmune effect associated with a PND, where present.

Accordingly, one object of the present invention is to isolate peptides of onconeural genes which function as epitopes, while reducing the risk of associated PND autoimmune disorders, and incorporate those epitopes into an immunogenic or tolerogenic composition.

Another object of the present invention is to contact a lymphocyte population, preferably and autologous population, with the immunogenic population such that the CTLs of the population are competent to elicit an immune response to an APC expressing either the cdr2 epitopes or the HuD epitopes.

A further object of the present invention is to administer cdr2-epitope specific or HuD-epitope specific CTLs to a subject with an onconeural carcinoma such that the CTLs both elicit an immune response to and ameliorate the presence of the onconeural cancer cells.

Another object of the present invention is to isolate a TCR that recognizes either a cdr2 antigen or HuD antigen when associated with an MHC class I molecule.

Another object of the present invention is to engineer a T cell such that it recognizes either a cdr2 antigen or HuD antigen through its TCR.

Another object of the present invention is to administer the cdr2 specific CTL or HuD-specific CTL to a subject with a onconeural carcinoma such that the CTL both elicit an immune response to and ameliorate the presence of the cancer cells.

Another object of the present invention is to detect for the presence of an onconeural antigen expressing carcinoma and/or a PND in a patent. More specifically, an object of the present invention is to detect for the presence of an SCLC or a gynecological tumor. Additionally, for those patients exhibiting the autoimmune response, an object of the present invention is to simultaneously detect for the presence of a PND. Such detection is accomplished through the use of targeted peptides and TCRs associated with the onconeural antigen within the carcinoma and the neural cells associated with the PND.

An further object is to administer a tolerogenic composition to a patient with an onconeural antigen expressing carcinoma and/or PCD such that the tolerogenic composition treats the carcinoma and the PCD.

BRIEF DESCRIPTION OF THE FIGURES

FIG. 5A. Nucleotide and deduced amino acid sequence of the cdr2 TCR α chain. The constant region is boxed. The CD3 domain of the variable region is underlined. The V gene segment (unboxed) was classified according to IMGT, the international ImMunoGeneTics Information System® (Lefranc, M-P et al, IMGT unique numbering for immunoglobulin and T cell receptor variable domains and Ig superfamily V-like domains. Dev. Comp. Immunol., 2003, 27, 55-77) and was determined to be TRV α 14D-1*01J42*01; CD3 sequence: CAASGASGGSNAKLTF (SEQ ID NO: 45).

FIG. 5B. Nucleotide and deduced amino acid sequence of the cdr2 TCR β chain. Upper box: CD3 domain. Lower box: constant region. To confirm TCR sequence analysis, CD8-purified clone 11 CTL were analyzed by staining with a panel of Vβ-subfamily domain antibodies (purple filled) or isotype control antibody (green line) followed by flow cytometry. Clone 11 CTL were determined to express only Vβ5, thus providing independent confirmation of both the clonality of the population and the results of the sequencing.

DETAILED DESCRIPTION OF THE INVENTION

Figure 1:
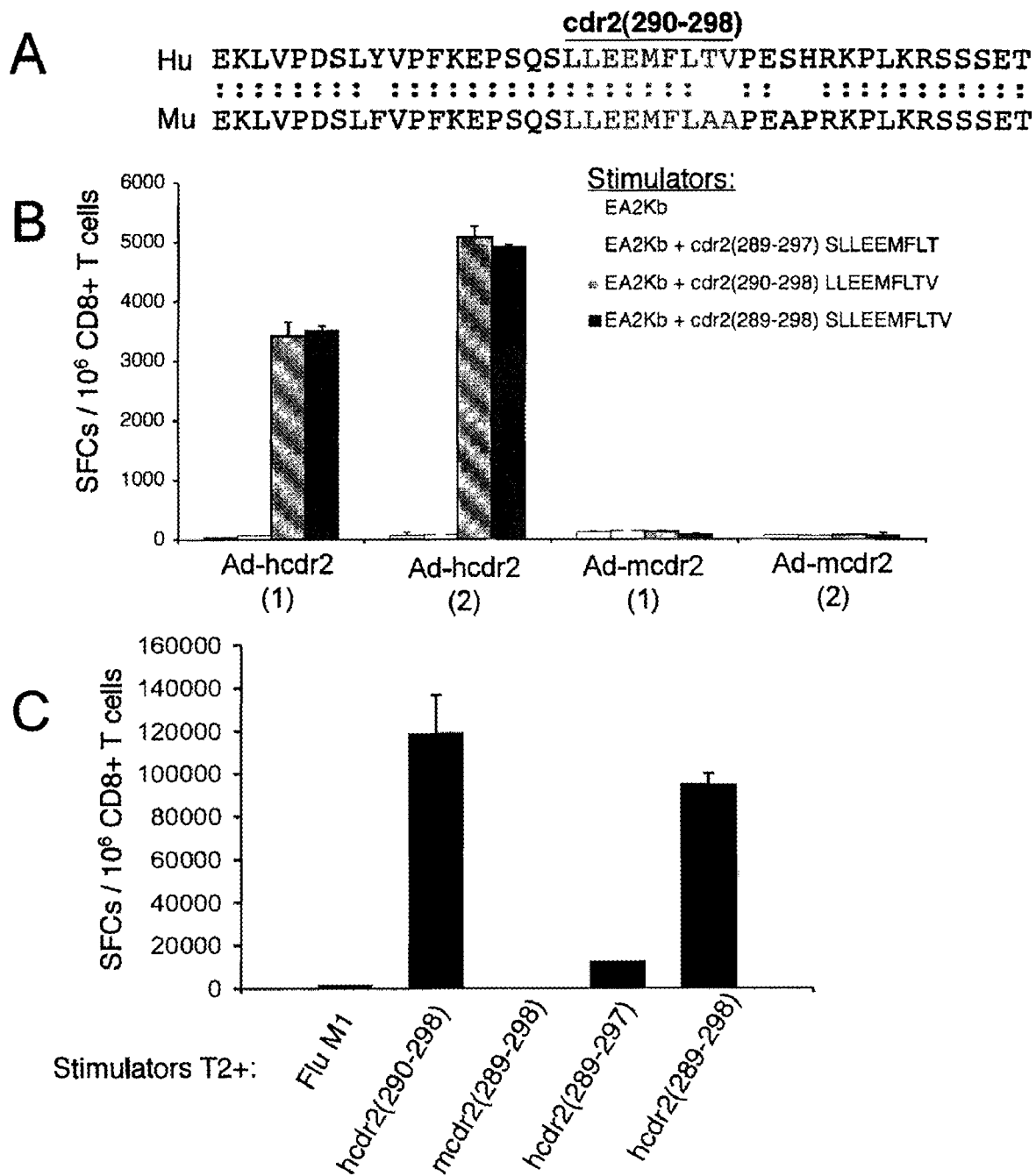
FIG. 1: Effect of characterization of cdr2 (290-298) specific CTLs from Ad-hcdr2 immunized A2.1 transgenic mice. (A) Sequence homology of murine (Mu) and human (Hu) cdr2 surrounding residues 290-298 (SEQ ID NO: 1 and SEQ ID NO: 41). (B) Direct ex vivo IFN-γ ELISPOT with Ad-hcdr2 immunized AAD mice. A2.1 transgenic mice were immunized with $10^9$ pfu of Ad-hcdr2 or Ad-mcdr2 (results from 2 different animals in each group are indicated). 12 d later, CD8$^+$ T cells were purified from splenocytes and co-cultured as indicated with human cdr2(289-297) (SEQ ID NO: 3), human cdr2(290-298) (SEQ ID NO: 1), human cdr2 (289-298) (SEQ ID NO: 39) peptide-pulsed ($10^{-5}$ M) EA2 Kb cells, or EA2 Kb alone in an 18 h IFN-γ ELISPOT assay. Values represent spot forming cells (SFC) per million CD8$^+$ T cells; the average of triplicate wells are shown with error bars indicating standard deviation. (C) Peptide-specific responses of AAD 290 CTL. Splenocytes from Ad-hcdr2 immunized AAD mice underwent 2 rounds of in vitro stimulation with human cdr2(290-298) (SEQ ID NO: 1). These cells, AAD 290 CTL, were tested for ability to recognize T2 cells pulsed with FluM1, human cdr2(290-298) (SEQ ID NO: 3), murine cdr2 (289-298) (SEQ ID NO: 40), human cdr2(289-297) (SEQ ID NO: 3), or human cdr2(289-298) (SEQ ID NO: 39) by ELISPOT as in (B). (D). CD8-independence of AAD 290 CTL. AAD 290 CTL were purified by CD8 negative selection and stained with tetrameric PE conjugates for A2.1/cdr2(290-298) (SEQ ID NO: 1), A2.1/cdr2(289-297) (SEQ ID NO: 3), and A2.1/FluM1(58-66).

For the purposes of promoting and understanding the principles of the invention, reference will now be made to numerous embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to compositions and accompanying methodologies for both stimulating an immunological response to a onconeural presenting tumor cell and detecting a PND. More specifically, in one embodiment the invention relates to compositions and methods of both promoting lymphocyte recognizition of either a cdr2 antigen or HuD antigen within a patient so as to elicit a therapeutically effective immunological response to an onconeural antigen-expressing carcinoma while limiting the risks of a PND. Such a method includes vaccinating a CTL population with an immunogenic composition comprised of one or more cdr2 epitopes or HuD epitopes rendering the CTL population competent to induce an immunological reaction to cdr2 or HuD expressing carcinomas, while reducing autoimmune responses associated with paraneoplastic neurologic disorders (PND). In another embodiment, the present invention relates to compositions and methods of detecting and treating PND, e.g. paraneoplastic cerebellar degeneration (PCD), within a subject. Such detection may be accomplished by isolating a lymphocyte population, e.g. from a patient suspected of having a PND, and evaluating the levels of lymphocytes within the population which are capable of inducing an immune reaction to a cdr2 antigen or HuD antigen of the present invention. The PND may be treated by administering to the patient a tolerizing composition in which the cdr2 peptide(s) or HuD peptide(s) of the present invention are used in an immunologically tolerizing manner, i.e. to treat the carcinoma while minimizing the immune response to the neurons.

In one embodiment, the present invention is comprised of an immunogenic composition. The immunogenic composition may be comprised of at least one, or any combination thereof, cdr2 antigen or HuD antigen and, optionally, an adjuvant. The cdr2 antigen may be comprised of any cdr2 peptide, polypeptide, protein, nucleotide, nucleotide construct, recombinant viral vector, recombinant bacterial plasmid or the like wherein the peptide and/or nucleotide encodes for at least one immunogenic antigen of the cdr2 protein. In one embodiment, the cdr2 antigen may be comprised of the peptide sequence or a nucleotide sequences encoding SEQ ID NO: 1 [LLEEMFLTV] wherein SEQ ID NO: 1 represents amino acid sequence 290-298 of the cdr2 protein, SEQ ID NO: 145. However, the cdr2 antigen of the immunogenic composition is not limited to this embodiment and may be comprised of at least one, or combination thereof, of the following peptide sequences or nucleotide sequences encoding the following peptide or protein sequences: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, ID No: 140, SEQ ID NO: 141, SEQ ID NO: 142, SEQ ID NO: 143, SEQ ID NO: 144 and SEQ ID NO: 145. Each of the above possibilities may represent a separate embodiment of the present invention.

The cdr2 antigens of the present invention may be further comprised of any peptide, or nucleotide sequence that is homologous to, a variant of, or a functional equivalent of the above sequences. The "homologous to" and "variant of" as used herein means the substitution of, variation of, modification of, replacement of, deletion of or addition of one (or more) amino acids from the peptide or nucleotides from the nucleic acid sequence wherein the substitution, variation, modification, replacement, deletion, or addition does not affect the overall charge, structure or binding ability of the peptide. A functionally equivalent sequence includes peptides with a sequence homology such as peptides having one or more specific conservative and/or non-conservative amino acid changes, peptide conjugates, chimeric proteins, fusion proteins and peptide nucleic acids wherein such amino acid changes do not significantly alter the overall charge and configuration of the peptide or the binding ability of the peptide. A functionally equivalent sequence may also include a nucleic acid sequence with partial sequence homology such as a nucleic acid sequence having one or more specific conservative and/or non-conservative nucleic acid changes wherein such change does not significantly alter the overall charge and configuration of the resulting peptide or the binding ability of the peptide.

The HuD antigen may be comprised of any HuD peptide, polypeptide, protein, nucleotide, nucleotide construct, recombinant viral vector, recombinant bacterial plasmid or the like wherein the peptide and/or nucleotide encodes for at least one immunogenic antigen of the HuD protein. In one embodiment, the HuD antigen may be comprised of the peptide sequence or a nucleotide sequences encoding SEQ ID NO: 146 [RIITSRILV]. In an alternative embodiment, however, the HuD antigen may be comprised of the peptide sequence or a nucleotide sequence encoding SEQ ID NO: 147 [NLYVSGLPK]. The HuD antigens of the present invention may be further comprised of any peptide, or nucleotide sequence that is homologous to, a variant of, or a functional equivalent of the above sequences. The "homologous to" and "variant of" as used herein means the substitution of, variation of, modification of, replacement of, deletion of or addition of one (or more) amino acids from the peptide or nucleotides from the nucleic acid sequence wherein the substitution, variation, modification, replacement, deletion, or addition does not affect the overall charge, structure or binding ability of the peptide. A functionally equivalent sequence includes peptides with a sequence homology such as peptides having one or more specific conservative and/or non-conservative amino acid changes, peptide conjugates, chimeric proteins, fusion proteins and peptide nucleic acids wherein such amino acid changes do not significantly alter the overall charge and configuration of the peptide or the binding ability of the peptide. A functionally equivalent sequence may also include a nucleic acid sequence with partial sequence homology such as a nucleic acid sequence having one or more specific conservative and/or non-conservative nucleic acid changes wherein such change does not significantly alter the overall charge and configuration of the resulting peptide or the binding ability of the peptide.

The immunogenic composition may be further comprised of an adjuvant and/or an immunostimulatory molecule. More specifically, the adjuvant may be comprised of at least one, or any combination thereof, pro-inflammatory, immunogenic, and/or tolerogenic chemical or molecule adjuvant such as, but not limited to, cytokines, chemokines, costimulatory molecules, or other immunomodulators that may amplify and direct the immune response to cancer cells or prevent neurologic disease.

In one embodiment, the adjuvant may be comprised of a compound or composition used to prevent neurologic disease wherein the adjuvant may be comprised of tacrolimus, FK-506, Fujimycin, rapamycin, and nataluzimab.

In another embodiment, the adjuvant may be comprised of a CpG-containing oligonucleotide sequence wherein adjacent guanine and a cytosine nucleosides are linked by a phosphate group. However, the CpG is not limited to this embodiment and may be comprised of a modified CpG-containing oligonucleotide. "Modified oligonucleotide" refers to an oligonucleotide in which at least two of its nucleotides are covalently linked via a synthetic internucleoside linkage (i.e., a linkage other than a phosphodiester linkage between the 5' end of one nucleotide and the 3' end of another nucleotide). For example, the synthetic internucleoside linkage may be a phosphorothioate linkage, an alkylphosphonate linkage, a phosphorodithioate linkage, a phosphate ester linkage, a alkylphosphonothioate linkage, a phosphoramidate linkage, a carbamate linkage, a carbonate linkage, a phosphate triester linkage, an acetamidate linkage, a carboxymethyl ester linkage, or any peptide linkage. "Modified oligonucleotide" may also refer to oligonucleotides with a covalently modified base and/or sugar. For example, such oligonucleotides may include oligonucleotides having backbone sugars covalently attached to low molecular weight organic groups other than a hydroxyl group at the 3' position and other than a phosphate group at the 5' position.

In another embodiment the adjuvant may be comprised of a cytokine. The cytokine may be comprised of, but not limited to, GM-CSF, CD40L, TNF-α, IFN-β, IL-1 through IL-15, RANTES, G-CSF, M-CSF, CTAP III, ENA-78, GRO, I-309, PF-4, IP-10, LD-78, MGSA, MIP-1.alpha., MIP-1.beta., or combination thereof, or any other immunostimulatory cytokine understood in the art to induce an immunological reaction.

The adjuvant is not limited to any of the above embodiments and may further comprise any other immunostimulator molecules including, but not limited to B7.1, B7.2, ICAM-1, ICAM-2, LFA-1, LFA-3, CD72, aluminum salt, Montanide ISA, a trimer of complement component C3d, MF59, saponin, monophosphoryl lipid A (MPL), SBAS2, a quill glycoside, a bacterial mitogen, a bacterial toxin, Freund's Complete Adjuvant (CFA), Freund's Incomplete Adjuvant (ISA), Hunter's Titermax®, Gerbu Adjuvant, Ribi's Adjuvant, and Nitrocellulose adsorbed protein or any other molecule understood in the art to stimulate an immunological reaction.

In another embodiment, the present invention also provides a method of both vaccinating for and/or inducing an immunological response to a onconeural-expressing tumor cell. More specifically, the method of this embodiment comprises the step of contacting a lymphocyte-containing cell population, preferably autologous, with an immunogenic composition of the present invention, either in vivo or ex vivo such that CTLs within the population are rendered competent to promote a tumor cell specific cell-mediated immune response within the subject. The CTLs may be rendered competent by any immunological mechanism understood in the art. For example, any of the cdr2 or HuD peptides of the foregoing immunogenic composition are exposed to a peripheral blood lymphocyte (PBL) population, either in vivo or ex vivo, wherein the exogenous peptide(s) are taken-up into antigen presenting cells, e.g. dendritic cells, monocytes/macrophages, B lymphocytes or the like, and displayed on the APC cell surface in conjunction with an MHC, preferably a class I, molecule. The antigen/MHC complex is then be recognized by a cdr2-specific or HuD-specific CTL within the lymphocyte population, in turn, leading to the stimulation and proliferation of the CTL population so as to facilitate a therapeutic immunological response while minimizing the effects of a PND. This response may be may be amplified by the optional adjuvant which may be contained within the immunogenic composition.

Embodiments of such cdr2-specific cancer cells may include, but are not limited to, a breast carcinoma, a cervical carcinoma, an ovarian carcinoma, a prostatic adenocarcinoma, a gastric adenocarcinoma, a fallopian tube adenocarcinoma, an esophageal adenocarcinoma, an addometrial carcinoma, a transitional cell carcinoma of the bladder or any other type of cdr2 expressing carcinoma known in the art. Embodiments of such HuD-expressing carcinomas include form of a small cell lung cancer or oat cell carcinoma known in the art.

While the cdr2 immunogenic peptide is preferably comprised of cdr2 peptide 290-298, SEQ ID. No: 1, the present inventions not limited to this embodiment. Rather, as noted in Tables 1-8 below, each of the listed cdr2 antigens are capable of binding to a MHC complex wherein the iscore indicates a ranking of the binding affinities of each antigen to the HLA allele. As such, one skilled in the art may easily substitute the cdr2 290-298 peptide with any of the peptides disclosed in Tables 1-8 to achieve the same or a similar immunostimulatory result.

In any of the above embodiments, the peptides of the present invention may, optionally, be linked to a helper peptide, lipid or liposome wherein the helper peptide, lipid, or liposome facilitates the ability of the antigen presenting cell to uptake the cdr2 or HuD peptide(s).

The above embodiment of the immunogenic composition is not limited to exogenous cdr2 or HuD peptides. In an alternative embodiment, the antigens of the immunogenic composition may be comprised of a nucleic acid sequence encoding a cdr2 or HuD peptide. Any of the nucleic acid sequences encoding the antigens may be inserted within a nucleotide vector, e.g. a recombinant viral vector, retroviral vector, bacterial plasmid vector, bacterial DNA or the like, so as to express any one or more of the antigen sequences of the present invention. To this end, the APC may be contacted or "loaded" with the immunogenic composition such that the nucleic acid is absorbed, expressed/processed, and presented on the cell surface of the antigen presenting cell. In a separate embodiment, any of the nucleotide vectors listed above may also be adapted to encode for at least one adjuvant wherein the adjuvant is expressed within the antigen presenting cell.

The methods of contacting the APC with the antigens of the present invention are not limited to the above embodiments. Rather, the cdr2 or HuD peptides may contact the APC using any method understood in the art to introduce an nucleic acid sequence and/or peptide into an APC such as, but not limited to, liposomal attachment, direct injection into an APC cell such as microinjection, culturing the lymphocytes in a cdr2 or HuD based culture medium, transfection, transduction, transformation, conjugation, endocytosis, phagocytosis, or direct administration to a subject. A detailed discussion of different methods of introducing an antigenic peptide/nucleotide to a lymphocyte population for induction of an immunological response is reviewed in Berzofsky, et. al *J. Clin. Invest.* 113 1515-1525 (2004); Rosenberg et. al. *Nat Med* 10 909-915 (2004); Dudley, et. al. *Nat Rev Cancer* 3 666-675 (2003); Rosenberg, S. A. *Nature*. 411 380-384 (2001); Boczkowski D. et al. *J. Exp. Med.* 184 465-472 (1996); Rouse et al. *J. Virol.* 68 5685-5689 (1994); and Nair et al. *J. Exp. Med.* 175 609-612 (1992) the contents of which are incorporated herein by reference.

In another embodiment, the method of contacting a lymphocyte population with the immunogenic composition may occur in vivo wherein the immunogenic composition is administered to the subject and contacts the antigen presenting cell within the subject. The immunogenic composition may be administered in one of several routes including, but not limited to, intravenous, intramuscular, subcutaneous, intradermal, intraperitoneal, intrathecal, intrapleural, intrauterine, rectal, vaginal, topical, intratumor, transmucosal, transdermal, oral, or any other method understood in the art to introduce an immunogenic composition into a subject. Additionally, the immunogenic composition may contact the APC using any of the pharmaceutical compositions discussed below.

In another embodiment, the method of contacting an APC with an immunogenic composition may occur ex vivo wherein an APC within a lymphocyte population, which may be autologous, is contacted with the immunogenic composition outside of the subject, and reintroduced into the subject. For example, the APC may be contacted with the immunogenic composition by culturing the lymphocytes in a medium containing any of the immunogenic compositions discussed above such that the cdr2 or HuD protein/peptide(s) are absorbed and presented on the surface of an antigen presenting cell ex vivo. The cdr2 or HuD displaying APCs may then be reintroduced into the subject. However, the present invention is not limited to autologous lymphocytes populations as disclosed above and may be comprised of any lymphocyte population immunologically compatible with the subject. Methods for ex vivo immunotherapy are well known in the art and are described, for example, in Davis I D et al. *J Immunother.* 2006 September-October; 29(5):499-511 and Mitchell M S et al., *Cancer Immunol Immunother.* 2006 July 28, the contents of which are incorporated herein by reference.

In a further embodiment, the immunogenic composition may further include an antibody that is able to specifically recognize and bind to at least one of the cdr2 or HuD peptides. The antibody may be produced by any well-known method for antibody production. For example, the antibody may be obtained by administration of any of the above embodiments of a cdr2 antigen or HuD antigen into an animal and harvesting the antibodies produced as a result. The antibodies may be harvested through any technique understood in the art such as, but not limited to, immunoaffinity chromatography. To this end, a lymphocyte population may be contacted with the immunogenic composition such that an antibody binds to the appropriate cdr2 or HuD antigen when displayed in conjunction with an MHC molecule on the cell surface of an APC so as to facilitate a therapeutic immunological response.

As noted above, the cdr2 antigen is associated with an HLA allele of an MHC complex and presented on the surface of an antigen presenting cell. In one embodiment, the HLA allele of the MHC complex may be comprised of HLA-A*0201 wherein the cdr2 peptide(s) of the immunogenic composition which binds to this allele may be comprised of any of the sequences disclosed in Table 1 below. As exemplified in Example 1, each of the cdr2 peptides below exhibited a greater than 30% binding affinity to the HLA-A*0201 molecule. Each allele is ranked according to its binding affinity (iscore) wherein the rank utilizes a multi-parametric calculation of the length of time each peptide remains bound to the MHC complex ($t_{1/2}$) and the dose dependant affinity of the peptide (ED).

TABLE 1

HLA-A*0201 Allele

| Position | Sequence | SID No. | ED50 | $t_{1/2}$ | iScore |
|---|---|---|---|---|---|
| 290-298 | LLEEMFLTV | 1 | 6.0E-07 | 5.9 | 0.815 |
| 203-211 | TMLQAQLSL | 2 | 8.0E-07 | 9.8 | 0.811 |
| 289-297 | SLLEEMFLT | 3 | 6.0E-06 | 13.9 | 0.803 |
| 341-349 | RGISLLHEV | 4 | 1.0E-06 | 7 | 0.752 |
| 65-73 | YLTKQVELL | 5 | 2.0E-06 | 8.1 | 0.645 |
| 260-268 | MLQSEHPFV | 6 | 2.0E-06 | 5.4 | 0.584 |
| 424-432 | ALFKEIFSC | 7 | 3.0E-05 | 18.7 | 0.546 |
| 217-225 | VTMEEEYGL | 8 | 2.0E-06 | 6.5 | 0.528 |
| 114-122 | SLTETIECL | 9 | 4.0E-06 | 9.3 | 0.518 |
| 111-119 | KILSLTETI | 10 | 7.0E-06 | 10.5 | 0.512 |
| 273-281 | KLVPDSLYV | 11 | 3.0E-06 | 6.1 | 0.499 |
| 384-392 | AAAKDLTGV | 12 | 3.0E-05 | 6.5 | 0.469 |
| 246-254 | RALELEAV | 13 | 1.0E-06 | 2.7 | 0.352 |
| 128-136 | HLQSQVEEL | 14 | 1.0E-05 | 7.7 | 0.323 |
| 168-176 | RQHFVYDHV | 15 | 6.0E-06 | 3.7 | 0.304 |
| 391-399 | GVNAQSEPV | 16 | 1.0E-05 | 6.4 | 0.292 |
| 372-380 | DSLSHKAVQ | 17 | 9.0E-06 | 6.3 | 0.262 |
| 171-179 | FVYDHVFAE | 18 | 1.0E-05 | 5.5 | 0.282 |
| 405-413 | LASVNPEPV | 19 | 4.0E-06 | 1.9 | 0.244 |
| 313-221 | TILSSLAGS | 20 | 2.0E-06 | 1.1 | 0.238 |
| 204-212 | MLQAQLSLE | 21 | 5.0E-06 | 5.1 | 0.235 |
| 345-353 | LLHEVDTQY | 22 | 7.0E-06 | 3.5 | 0.204 |
| 197-205 | HLKKTVTML | 23 | 1.0E-05 | 2.5 | 0.199 |
| 164-172 | LYDLRQHFV | 24 | 5.0E-07 | 0.4 | 0.199 |
| 400-408 | ASGWELASV | 25 | 1.0E-06 | 0.5 | 0.187 |
| 120-128 | ECLQTNIDH | 26 | 3.0E-05 | 5.4 | 0.178 |
| 121-129 | CLQTNIDHL | 27 | 2.0E-05 | 2.4 | 0.176 |
| 107-113 | ASQQKILSL | 28 | 8.0E-06 | 3.4 | 0.174 |
| 125-133 | NIDHLQSQV | 29 | 6.0E-06 | 1.3 | 0.166 |
| 29-37 | QLAAELGKT | 30 | 2.0E-05 | 1.4 | 0.150 |
| 274-282 | LVPDSLYVP | 31 | 1.0E-05 | 2.4 | 0.154 |
| 82-90 | KVYEQLDVT | 32 | 8.0E-06 | 1.3 | 0.139 |
| 201-209 | TVTMLQAQL | 33 | 3.0E-06 | 0.6 | 0.132 |
| 237-245 | LGATGAYRA | 34 | 1.0E-05 | 1.2 | 0.130 |
| 373-381 | SLSHKAVQT | 35 | 4.0E-06 | 0.8 | 0.129 |
| 225-233 | LVLKENSEL | 36 | 7.0E-06 | 0.8 | 0.119 |
| 355-363 | ALKVKYEEL | 37 | 7.0E-06 | 0.8 | 0.107 |
| 176-184 | VFAEKITSL | 38 | 5.0E-06 | 0.4 | 0.106 |
| 113-121 | LSLTETIEC | 58 | 9.5E-07 | 0.51 | 0.187 |
| 288-296 | QSLLEEMFL | 59 | 3.0E-05 | 5.44 | 0.178 |
| 136-144 | LKSSGQGRR | 60 | 1.6E-05 | 2.38 | 0.176 |
| 206-214 | QAQLSLERQ | 61 | 8.1E-06 | 3.42 | 0.174 |
| 218-226 | TMEEEYGLV | 62 | 6.3E-06 | 1.27 | 0.166 |
| 131-139 | SQVEELKSS | 63 | 1.1E-05 | 2.42 | 0.154 |
| 293-301 | EMFLTVPES | 64 | 1.7E-05 | 1.38 | 0.150 |
| 209-217 | LSLERQKRV | 65 | 8.4E-06 | 1.25 | 0.139 |
| 163-171 | ELYDLRQHF | 66 | 2.7E-06 | 0.55 | 0.132 |

The HLA allele of the MHC complex may also be comprised of HLA-A*0101 wherein the cdr2 peptide(s) of the immunogenic composition which binds to this allele may be comprised of any of the sequences disclosed in Table 2 below. As noted above, Example 1 exemplifies the binding affinities of the cdr2 peptides to the HLA-A*0201 HLA allele based on the ED, $t_{1/2}$ and iscores of Table 1. However, the present invention is not limited to the Example 1. Rather, one skilled in the art, utilizing an ED, $t_{1/2}$ and iscore of other cdr2 peptides to the HLA-A*0101 allele, as disclosed in Table 2, can easily determine which cdr2 peptides sufficiently binding to the MHC molecule such that the stimulation of the immunological reaction above occurs.

TABLE 1

HLA-A*0101 Allele

| Position | Sequence | SID No. | ED50 | $t_{1/2}$ | iScore |
|---|---|---|---|---|---|
| 290-298 | LLEEMFLTV | 1 | 2.1E-05 | 0.27 | 0.063 |
| 157-165 | SFACLKELY | 54 | 6.9E-06 | 0.97 | 0.137 |
| 439-447 | EIDEQRTKY | 55 | 3.1E-05 | 1.26 | 0.107 |
| 414-422 | SSPTTPPEY | 56 | 1.3E-04 | 0.96 | 0.050 |
| 350-358 | DTQYSALKV | 57 | 4.9E-05 | 0.40 | 0.040 |

The HLA allele of the MHC complex may also be comprised of HLA-A*0301 wherein the cdr2 peptide(s) of the immunogenic composition which binds to this allele may be comprised of any of the sequences disclosed in Table 3 below. As noted above, Example 1 exemplifies the binding affinities of the cdr2 peptides to the HLA-A*0201 HLA allele based on the ED, $t_{1/2}$ and iscores of Table 1. However, the present invention is not limited to the Example 1. Rather, one skilled in the art, utilizing an ED, $t_{1/2}$ and iscore of other cdr2 peptides to the HLA-A*0301 allele, as disclosed in Table 3, can easily determine which cdr2 peptides sufficiently binding to the MHC molecule such that the stimulation of the immunological reaction above occurs.

TABLE 3

HLA-A*0301 Allele

| Position | Sequence | SID No. | ED50 | $t_{1/2}$ | iScore |
|---|---|---|---|---|---|
| 331-339 | CIRRAKAVK | 67 | 1.4E-05 | 6.47 | 0.436 |
| 379-387 | VQTSRAAAK | 68 | 1.8E-05 | 2.55 | 0.279 |
| 351-359 | TQYSALKVK | 69 | 7.5E-06 | 1.48 | 0.270 |
| 140-148 | GQGRRSPGK | 70 | 7.8E-06 | 1.64 | 0.258 |
| 427-435 | KEIFSCIKK | 71 | 1.3E-05 | 5.82 | 0.231 |
| 300-308 | ESHRKPLKR | 72 | 1.9E-05 | 1.49 | 0.147 |
| 74-82 | RQMNEQHAK | 73 | 5.8E-05 | 3.69 | 0.147 |
| 317-325 | SLAGSDIVK | 74 | 1.1E-05 | 0.88 | 0.140 |
| 296-304 | LTVPESHRK | 75 | 2.6E-05 | 1.53 | 0.128 |
| 236-244 | QLGATGAYR | 76 | 1.5E-05 | 0.92 | 0.122 |
| 154-162 | PAPSFACLK | 77 | 1.1E-05 | 2.19 | 0.122 |
| 205-213 | LQAQLSLER | 78 | 1.9E-05 | 0.99 | 0.087 |
| 28-36 | LQLAAELGK | 79 | 1.5E-05 | 1.12 | 0.086 |
| 207-215 | AQLSLERQK | 80 | 2.5E-05 | 0.97 | 0.075 |
| 265-273 | HPFVNGVEK | 81 | 3.4E-05 | 0.61 | 0.050 |
| 172-180 | VYDHVFAEK | 82 | 2.5E-05 | 0.36 | 0.048 |

The HLA allele of the MHC complex may also be comprised of HLA-A*1101 wherein the cdr2 peptide(s) of the immunogenic composition which binds to this allele may be comprised of any of the sequences disclosed in Table 4 below. As noted above, Example 1 exemplifies the binding affinities of the cdr2 peptides to the HLA-A*0201 HLA allele based on the ED, $t_{1/2}$ and iscores of Table 1. However, the present invention is not limited to the Example 1. Rather, one skilled in the art, utilizing an ED, $t_{1/2}$ and iscore of other cdr2 peptides to the HLA-A*1101 allele, as disclosed in Table 4, can easily determine which cdr2 peptides sufficiently binding to the MHC molecule such that the stimulation of the immunological reaction above occurs.

TABLE 4

HLA-A*1101 Allele

| Position | Sequence | SID No. | ED50 | $t_{1/2}$ | iScore |
|---|---|---|---|---|---|
| 107-113 | ASQQKILSL | 28 | 2.0E-05 | 2.45 | 0.190 |
| 379-387 | VQTSRAAAK | 68 | 4.6E-06 | 1.50 | 0.343 |
| 351-359 | TQYSALKVK | 69 | 2.8E-06 | 0.76 | 0.276 |
| 140-148 | GQGRRSPGK | 70 | 2.0E-06 | 2.80 | 0.633 |
| 427-435 | KEIFSCIKK | 71 | 7.0E-06 | 3.74 | 0.392 |
| 300-308 | ESHRKPLKR | 72 | 2.6E-05 | 0.35 | 0.063 |
| 74-82 | RQMNEQHAK | 73 | 1.1E-05 | 3.85 | 0.396 |
| 317-325 | SLAGSDIVK | 74 | 2.1E-06 | 0.74 | 0.283 |
| 296-304 | LTVPESHRK | 75 | 4.8E-06 | 4.59 | 0.558 |
| 236-244 | QLGATGAYR | 76 | 2.7E-05 | 0.20 | 0.038 |
| 205-213 | LQAQLSLER | 78 | 1.1E-05 | 0.56 | 0.118 |
| 28-36 | LQLAAELGK | 79 | 7.9E-06 | 1.00 | 0.194 |
| 207-215 | AQLSLERQK | 80 | 5.7E-06 | 1.40 | 0.271 |
| 172-180 | VYDHVFAEK | 82 | 8.8E-06 | 0.70 | 0.146 |
| 357-365 | KVKYEELLK | 83 | 1.2E-06 | 2.26 | 0.220 |
| 415-423 | SPTTPPEYK | 84 | 2.0E-05 | 1.78 | 0.136 |
| 129-137 | LQSQVEELK | 85 | 2.4E-05 | 1.10 | 0.103 |
| 339-347 | KQRGISLLH | 86 | 2.2E-05 | 0.44 | 0.089 |
| 429-437 | IFSCIKKTK | 87 | 1.2E-05 | 0.92 | 0.088 |
| 276-284 | PDSLYVPFK | 88 | 2.5E-05 | 0.41 | 0.063 |
| 401-409 | SGWELASVN | 89 | 3.1E-05 | 0.80 | 0.059 |
| 419-427 | PPEYKALFK | 90 | 2.6E-05 | 0.31 | 0.058 |
| 238-246 | GATGAYRAR | 91 | 1.9E-05 | 0.30 | 0.056 |
| 103-111 | ADSKASQQK | 92 | 5.6E-05 | 0.51 | 0.054 |
| 60-68 | LQEIEYLTK | 93 | 6.2E-05 | 0.68 | 0.048 |
| 66-74 | LTKQVELLR | 144 | 7.9E-06 | 1.56 | 0.238 |

The HLA allele of the MHC complex may also be comprised of HLA-A*2402 wherein the cdr2 peptide(s) of the immunogenic composition which binds to this allele may be comprised of any of the sequences disclosed in Table 5 below. As noted above, Example 1 exemplifies the binding affinities of the cdr2 peptides to the HLA-A*0201 HLA allele based on the ED, $t_{1/2}$ and iscores of Table 1. However, the present invention is not limited to the Example 1. Rather, one skilled in the art, utilizing an ED, $t_{1/2}$ and iscore of other cdr2 peptides to the HLA-A*2402 allele, as disclosed in Table 5, can easily determine which cdr2 peptides sufficiently binding to the MHC molecule such that the stimulation of the immunological reaction above occurs.

TABLE 5

HLA-A*2402 Allele

| Position | Sequence | SID No. | ED50 | $t_{1/2}$ | iScore |
|---|---|---|---|---|---|
| 203-211 | TMLQAQLSL | 2 | 7.0E-07 | 0.25 | 0.117 |
| 65-73 | YLTKQVELL | 5 | 1.9E-06 | 0.22 | 0.107 |
| 111-119 | KILSLTETI | 10 | 1.5E-06 | 0.82 | 0.261 |
| 197-205 | HLKKTVTML | 23 | 8.9E-05 | 0.80 | 0.075 |
| 164-172 | LYDLRQHFV | 24 | 1.6E-06 | 0.27 | 0.157 |
| 120-128 | ECLQTNIDH | 26 | 1.8E-05 | 0.72 | 0.095 |
| 355-363 | ALKVKYEEL | 37 | 1.0E-05 | 0.38 | 0.076 |
| 176-184 | VFAEKITSL | 38 | 2.6E-07 | 0.78 | 0.446 |
| 172-180 | VYDHVFAEK | 82 | 6.2E-06 | 1.65 | 0.165 |
| 429-437 | IFSCIKKTK | 87 | 8.6E-06 | 1.16 | 0.108 |
| 242-250 | AYRARALEL | 94 | 1.6E-07 | 1.11 | 0.611 |
| 425-433 | LFKEIFSCI | 95 | 7.5E-08 | 1.11 | 0.529 |
| 421-429 | EYKALFKEI | 96 | 4.4E-07 | 1.63 | 0.505 |
| 282-290 | PFKEPSQSL | 97 | 4.9E-07 | 1.25 | 0.496 |
| 64-72 | EYLTKQVEL | 98 | 6.5E-07 | 1.72 | 0.444 |
| 52-60 | MYTTNQEQL | 99 | 5.4E-07 | 1.46 | 0.441 |
| 422-430 | YKALFKEIF | 100 | 1.5E-06 | 1.60 | 0.357 |
| 266-274 | PFVNGVEKL | 101 | 1.4E-06 | 0.49 | 0.218 |
| 339-347 | KQRGISLLH | 102 | 6.9E-06 | 1.52 | 0.184 |
| 338-346 | VKQRGISLL | 103 | 1.0E-05 | 1.15 | 0.172 |
| 157-165 | SFACLKELY | 104 | 1.4E-06 | 0.50 | 0.157 |
| 58-66 | EQLQEIEYL | 105 | 3.4E-06 | 1.47 | 0.142 |
| 337-345 | AVKQRGISL | 106 | 2.0E-05 | 1.60 | 0.130 |
| 275-283 | VPDSLYVPF | 107 | 9.2E-06 | 1.26 | 0.116 |
| 352-360 | QYSALKVKY | 108 | 3.1E-06 | 0.35 | 0.098 |
| 169-177 | QHFVYDHVF | 109 | 3.1E-06 | 0.21 | 0.097 |
| 163-171 | ELYDLRQHF | 110 | 3.3E-06 | 0.23 | 0.095 |
| 271-279 | VEKLVPDSL | 111 | 8.8E-06 | 1.02 | 0.092 |
| 173-181 | YDHVFAEKI | 112 | 1.8E-05 | 0.75 | 0.089 |
| 418-426 | TPPEYKALF | 113 | 1.1E-05 | 0.46 | 0.084 |
| 259-267 | QMLQSEHPF | 114 | 5.3E-06 | 0.25 | 0.082 |
| 316-324 | SSLAGSDIV | 115 | 4.3E-05 | 1.32 | 0.081 |
| 37-45 | TLLDRNTEL | 116 | 5.6E-05 | 1.39 | 0.080 |

TABLE 5-continued

HLA-A*2402 Allele

| Position | Sequence | SID No. | ED50 | $t_{1/2}$ | iScore |
|---|---|---|---|---|---|
| 201-209 | TVTMLQAQL | 117 | 4.3E-05 | 0.59 | 0.062 |
| 79-87 | QHAKVYEQL | 118 | 1.0E-05 | 0.25 | 0.058 |
| 287-295 | SQSLLEEMF | 119 | 1.4E-05 | 0.24 | 0.048 |

The HLA allele of the MHC complex may also be comprised of HLA-B*0702 wherein the cdr2 peptide(s) of the immunogenic composition which binds to this allele may be comprised of any of the sequences disclosed in Table 6 below. As noted above, Example 1 exemplifies the binding affinities of the cdr2 peptides to the HLA-A*0201 HLA allele based on the ED, $t_{1/2}$ and iscores of Table 1. However, the present invention is not limited to the Example 1. Rather, one skilled in the art, utilizing an ED, $t_{1/2}$ and iscore of other cdr2 peptides to the HLA-B*0702 allele, as disclosed in Table 6, can easily determine which cdr2 peptides sufficiently binding to the MHC molecule such that the stimulation of the immunological reaction above occurs.

TABLE 6

HLA-B*0702 Allele

| Position | Sequence | SID No. | ED50 | $t_{1/2}$ | iScore |
|---|---|---|---|---|---|
| 197-205 | HLKKTVTML | 23 | 9.9E-05 | 0.11 | 0.022 |
| 225-233 | LVLKENSEL | 36 | 3.4E-05 | 0.49 | 0.054 |
| 242-250 | AYRARALEL | 94 | 2.3E-05 | 0.15 | 0.033 |
| 337-345 | AVKQRGISL | 106 | 2.4E-06 | 1.18 | 0.293 |
| 275-283 | VPDSLYVPF | 107 | 4.7E-05 | 0.58 | 0.068 |
| 418-426 | TPPEYKALF | 113 | 1.0E-04 | 1.26 | 0.027 |
| 298-306 | VPESHRKPL | 120 | 9.9E-06 | 1.33 | 0.220 |
| 153-161 | KPAPSFACL | 121 | 5.5E-06 | 1.29 | 0.205 |
| 378-386 | AVQTSRAAA | 122 | 1.1E-05 | 0.90 | 0.153 |
| 240-248 | TGAYRARAL | 123 | 5.7E-06 | 0.22 | 0.082 |
| 244-252 | RARALELEA | 124 | 1.4E-05 | 0.47 | 0.080 |
| 253-261 | EVAEMRQML | 125 | 1.8E-05 | 0.74 | 0.077 |
| 381-389 | TSRAAAKDL | 126 | 1.8E-05 | 1.19 | 0.067 |
| 68-76 | KQVELLRQM | 127 | 1.8E-04 | 1.15 | 0.055 |
| 30-38 | LAAELGKTL | 128 | 3.3E-05 | 0.50 | 0.052 |
| 229-237 | ENSELEQQL | 129 | 9.3E-05 | 1.13 | 0.050 |
| 444-452 | RTKYRSLSS | 130 | 7.3E-05 | 1.83 | 0.031 |
| 442-450 | EQRTKYRSL | 131 | 1.0E-04 | 1.59 | 0.031 |

The HLA allele of the MHC complex may also be comprised of HLA-B*0801 wherein the cdr2 peptide(s) of the immunogenic composition which binds to this allele may be comprised of any of the sequences disclosed in Table 7 below. As noted above, Example 1 exemplifies the binding affinities of the cdr2 peptides to the HLA-A*0201 HLA allele based on the ED, $t_{1/2}$ and iscores of Table 1. However, the present invention is not limited to the Example 1. Rather, one skilled in the art, utilizing an ED, $t_{1/2}$ and iscore of other cdr2 peptides to the HLA-B*0801 allele, as disclosed in Table 7 can easily determine which cdr2 peptides sufficiently binding to the MHC molecule such that the stimulation of the immunological reaction above occurs.

TABLE 7

HLA-B*0801 Allele

| Position | Sequence | SID No. | ED50 | $t_{1/2}$ | iScore |
|---|---|---|---|---|---|
| 197-205 | HLKKTVTML | 23 | 3.7E-05 | 1.03 | 0.123 |
| 355-363 | ALKVKYEEL | 37 | 8.4E-05 | 1.05 | 0.099 |
| 209-217 | LSLERQKRV | 65 | 2.8E-04 | 0.77 | 0.046 |
| 163-171 | ELYDLRQHF | 66 | 3.4E-04 | 0.76 | 0.037 |
| 242-250 | AYRARALEL | 94 | 2.6E-05 | 0.34 | 0.066 |
| 337-345 | AVKQRGISL | 106 | 2.2E-05 | 1.04 | 0.139 |
| 37-45 | TLLDRNTEL | 116 | 3.6E-04 | 0.81 | 0.045 |
| 442-450 | EQRTKYRSL | 131 | 1.5E-05 | 1.11 | 0.160 |
| 240-248 | TGAYRARAL | 132 | 1.8E-05 | 0.45 | 0.085 |
| 196-204 | EHLKKTVTM | 133 | 1.3E-04 | 0.76 | 0.065 |
| 432-440 | CIKKTKQEI | 134 | 2.4E-04 | 0.69 | 0.054 |
| 211-219 | LERQKRVTM | 135 | 1.4E-04 | 0.33 | 0.037 |

The HLA allele of the MHC complex may also be comprised of HLA-A*1501 wherein the cdr2 peptide(s) of the immunogenic composition which binds to this allele may be comprised of any of the sequences disclosed in Table 8 below. As noted above, Example 1 exemplifies the binding affinities of the cdr2 peptides to the HLA-A*0201 HLA allele based on the ED, $t_{1/2}$ and iscores of Table 1. However, the present invention is not limited to the Example 1. Rather, one skilled in the art, utilizing an ED, $t_{1/2}$ and iscore of other cdr2 peptides to the HLA-A*1501 allele, as disclosed in Table 8, can easily determine which cdr2 peptides sufficiently binding to the MHC molecule such that the stimulation of the immunological reaction above occurs.

TABLE 8

HLA-A*1501 Allele

| Position | Sequence | SID No. | ED50 | $t_{1/2}$ | iScore |
|---|---|---|---|---|---|
| 424-432 | ALFKEIFSC | 7 | 8.3E-06 | 2.11 | 0.053 |
| 168-176 | RQHFVYDHV | 15 | 3.9E-05 | 0.79 | 0.088 |
| 345-353 | LLHEVDTQY | 22 | 3.9E-05 | 1.98 | 0.121 |
| 107-113 | ASQQKILSL | 28 | 2.4E-05 | 0.72 | 0.092 |
| 351-359 | TQYSALKVK | 69 | 7.6E-06 | 1.31 | 0.181 |
| 339-347 | KQRGISLLH | 102 | 2.2E-05 | 1.88 | 0.163 |
| 157-165 | SFACLKELY | 104 | 5.3E-06 | 0.67 | 0.132 |
| 337-345 | AVKQRGISL | 106 | 1.5E-05 | 1.47 | 0.160 |
| 259-267 | QMLQSEHPF | 114 | 8.3E-06 | 2.03 | 0.257 |
| 287-295 | SQSLLEEMF | 119 | 2.9E-05 | 0.47 | 0.062 |

TABLE 8-continued

HLA-A*1501 Allele

| Position | Sequence | SID No. | ED50 | $t_{1/2}$ | iScore |
|---|---|---|---|---|---|
| 378-386 | AVQTSRAAA | 122 | 5.1E-05 | 0.78 | 0.062 |
| 235-243 | QQLGATGAY | 136 | 8.6E-06 | 2.23 | 0.255 |
| 244-252 | RARALELEA | 137 | 4.8E-05 | 1.67 | 0.118 |
| 72-80 | LLRQMNEQH | 138 | 6.8E-05 | 1.62 | 0.106 |
| 165-173 | YDLRQHFVY | 139 | 4.5E-05 | 1.18 | 0.098 |
| 24-32 | LQQDLQLAA | 140 | 4.2E-05 | 1.37 | 0.090 |
| 257-265 | MRQMLQSEH | 141 | 1.7E-04 | 1.85 | 0.075 |
| 156-164 | PSFACLKEL | 142 | 4.5E-05 | 0.73 | 0.072 |
| 213-221 | RQKRVTMEE | 143 | 1.1E-04 | 1.21 | 0.065 |

The present invention is not limited to the above embodiments, rather, the cdr2 antigen may be any immunodominant epitope within the cdr2 protein that may bind to any of the following alleles and be displayed on the surface of an antigen presenting cell: HLA-A*0101, HLA-A*0201, HLA-A*0301, HLA-A*1101, HLA-A*2402, HLA-B*0702, HLA-B*0801, and HLA-A*1501. Moreover, the MHC molecule may be any allele within the following loci: HLA-A*01, HLA-A*02, HLA-A*03, HLA-A*11, HLA-A*24, HLA-B*7, HLA-B*8, HLA-B*27, HLA-A, HLA-B, or HLA-C. Each possibility of the above represent separate embodiments of the present invention.

As further noted above, the HuD antigen is associated with an HLA allele of an MHC complex and presented on the surface of an antigen presenting cell. In one embodiment, the HLA allele of the MHC complex may be comprised of HLA-A*0201 wherein the HuD peptide of the immunogenic composition which binds to this allele may be comprised of RIITSRILV (SEQ ID NO: 146).

In an alternative embodiment, the HLA allele of the MHC complex may be comprised of HLA-A*0301 wherein the HuD peptide of the immunogenic composition which binds to this allele may be comprised of NLYVSGLPK (SEQ ID NO: 147).

In another embodiment, the present invention also relates to an isolated murine T Cell Receptor (TCR) wherein the TCR recognizes an MHC molecule associated with a cdr2 peptide. The TCR may be comprised of, but is not limited to, an alpha chain with a cdr3 region, variable region and a constant region, a beta chain with a cdr3 region, variable region and a constant region, and a transmembrane region. The nucleotide sequence of the alpha chain may be comprised of SEQ ID NO: 44:

(SEQ ID NO: 44)
atggacaagattctgacagcatcattttactcctaggccttcaccta gctggggtgaatggccagcagaaggagaaacatgaccagcagcaggtg agacaaagtcccccaatctctgacagtctgggaaggaggaaccacagtt

```
ctgacctgcagttatgaggacagcacttttaactacttcccatggtac caacagttcctggggaaggccctgcacttctgatatccatactttca gtgtccgataaaaaggaagatggacgattcacaaccttcttcaataaa agggagaaaaagctctccttgcacatcatagactctcagcctggagac tcagccacctacttctgtgcagcaagtggggcttctggaggaagcaat gcaaagctaaccttcgggaaaggcactaaactctctgttaaatcaaac atccagaacccagaacctgctgtgtaccagttaaaagatcctcggtct caggacagcaccctctgcctgttcaccgactttgactcccaaatcaat gtgccgaaaaccatggaatctggaacgttcatcactgacaaaactgtg ctggacatgaaagctatggattccaagagcaatgggccattgcctgg agcaaccagacaagcttcacctgccaagatatcttcaaagagaccaac gccacctaccccagttcagacgttccctgtgatgccacgttgactgag aaaagctttgaaacagatatgaacctaaactttcaaaacctgtcagtt atgggactccgaatcctcctgctgaaagtagccggatttaacctgctc atgacgctgaggctgtggtccagt.
```

The amino acid sequence of the alpha chain of the TCR may be comprised of SEQ ID NO: 47:

```
                                         (SEQ ID NO: 47)
MDKILTASFLLLGLHLAGVNGQQKEKHDQQQVRQSPQSLTVWEGGTTV

LTCSYEDSTFNYFPWYQQFPGEGPALLISILSVSDKKEDGRFTTFFNK

REKKLSLHIIDSQPGDSATYFCAASGASGGSNAKLTFGKGTKLSVKSN

IQNPEPAVYQLKDPRSQDSTLCLFTDFDSQINVPKTMESGTFITDKTV

LDMKAMDSKSNGAIAWSNQTSFTCQDIFKETNATYPSSDVPCDATLTE

KSFETDMNLNFQNLSVMGLRILLLKVAGFNLLMTLRLWSS.
```

The nucleotide sequence of the variable region of the alpha chain may be comprised of SEQ ID NO: 43:

```
                                         (SEQ ID NO: 43)
atggacaagattctgacagcatcattttactcctaggccttcaccta gctggggtgaatggccagcagaaggagaaacatgaccagcagcaggtg agacaaagtccccaatctctgacagtctgggaaggaggaaccacagtt ctgacctgcagttatgaggacagcacttttaactacttcccatggtac caacagttcctggggaaggccctgcacttctgatatccatactttca gtgtccgataaaaaggaagatggacgattcacaaccttcttcaataaa agggagaaaaagctctccttgcacatcatagactctcagcctggagac tcagccacctacttctgtgcagcaagtggggcttctggaggaagcaat gcaaagctaaccttcgggaaaggcactaaactctctgttaaatcaaac atccagaacccagaacctgctgtgtac.
```

The amino acid sequence of the variable region of the alpha chain may be comprised of SEQ ID NO: 46.

```
                                         (SEQ ID NO: 46)
MDKILTASFLLLGLHLAGVNGQQKEKHDQQQVRQSPQSLTVWEGGTTV

LTCSYEDSTFNYFPWYQQFPGEGPALLISILSVSDKKEDGRFTTFFNK

REKKLSLHIIDSQPGDSATYFCAASGASGGSNAKLTFGKGTKLSVKSN

IQNPEPAVY.
```

However, one skilled in the art will appreciate that regions of the TCR outside the variable region can be modified without changing the specificity of the TCR.

The nucleotide sequence of the cdr3 region of the alpha chain may be comprised of SEQ ID NO: 42:

```
                                         (SEQ ID NO: 42)
tgtgcagcaagtggggcttctggaggaagcaatgcaaagctaaccttc ggg.
```

The amino acid sequence of the cdr3 of the alpha chain may be comprised of SEQ ID NO: 45:

```
       CAASGASGGSNAKLTFG.            (SEQ ID NO: 45)
```

However, one skilled in the art will appreciate that regions of the TCR outside cdr3 can be modified without changing the specificity of the TCR.

The alpha chain sequence, variable region and cdr3 region are not limited to the above embodiments. Rather, they may be comprised of any embodiment that is homologous to or a variant of the above sequences. In other words, the alpha chain may be comprised of any sequence that is either homologous to or a variant of SEQ ID NO: 44 and/or SEQ ID NO: 47. The variable region on the alpha chain may be comprised of any sequence that is either homologous to or a variant of SEQ ID NO: 43 and/or SEQ ID NO: 46. Finally, the cdr3 region on the alpha chain may be comprised of any sequence that is either homologous to or a variant of SEQ ID NO: 42 and/or SEQ ID NO: 45.

The nucleotide sequence of the beta chain may be comprised of SEQ ID NO: 50:

```
                                         (SEQ ID NO: 50)
atgtctaacactgtcctcgctgattctgcctggggcatcaccctgcta tctttgggttactgtctttctcttgggaacaagttcagcagattctggg gttgtccagtctccaagacacataatcaaagaaaagggaggaaggtcc gttctgacgtgtattcccatctctggacatagcaatgtggtctggtac cagcagactctggggaaggaattaaagttccttattcagcattatgaa aaggtggagagagacaaaggattcctacccagcagattctcagtccaa cagtttgatgactatcactctgaaatgaacatgagtgccttggaactg gaggactctgctatgtacttctgtgccagctctctcggaggatgggct gagcagttcttcggaccagggacacgactcaccgtcctagaggatctg agaaatgtgactccacccaaggtctccttgtttgagccatcaaaagca gagattgcaaacaaacaaaaggctaccctcgtgtgcttggccagggcc ttcttccctgaccacgtggagctgagctggtgggtgaatggcaaggag gtccacagtggggtcagcacggacctcaggcctacaaggagagcaat tatagctactgcctgagcagccgcctgagggtctctgctaccttctgg
```

-continued

```
cacaatcctcgaaaccacttccgctgccaagtgcagttccatgggctt tcagaggaggacaagtggccagagggctcacccaaacctgtcacacag aacatcagtgcagaggcctggggccgagcagactgtggaatcacttca gcatcctatcatcaggggttctgtctgcaaccatcctctatgagatc ctactggggaaggccaccctatatgctgtgctggtcagtggcctggtg ctgatggccatggtcaagaaaaaaaattcctga
```

The amino acid sequence of beta chain of the TCR may be comprised of SEQ ID NO: 53:

```
                                    (SEQ ID NO: 53)
MSNTVLADSAWGITLLSWVTVFLLGTSSADSGVVQSPRHIIKEKGGRS

VLTCIPISGHSNVVWYQQTLGKELKFLIQHYEKVERDKGFLPSRFSVQ

QFDDYHSEMNMSALELEDSAMYFCASSLGGWAEQFFGPGTRLTVLEDL

RNVTPPKVSLFEPSKAEIANKQKATLVCLARGFFPDHVELSWWVNGKE

VHSGVSTDPQAYKESNYSYCLSSRLRVSATFWHNPRNHFRCQVQFHGL

SEEDKWPEGSPKPVTQNISAEAWGRADCGITSASYHQGVLSATILYEI

LLGKATLYAVLVSGLVLMAMVKKKNS.
```

The nucleotide sequence of the variable region of the beta chain may be comprised of SEQ ID NO: 49:

```
                                    (SEQ ID NO: 49)
atgtctaacactgtcctcgctgattctgcctggggcatcaccctgcta tctttgggttactgtctttctcttgggaacaagttcagcagattctggg gttgtccagtctccaagacacataatcaaagaaaagggaggaaggtcc gttctgacgtgtattcccatctctggacatagcaatgtggtctggtac cagcagactctggggaaggaattaaagttccttattcagcattatgaa aaggtggagagagacaaaggattcctacccagcagattctcagtccaa cagtttgatgactatcactctgaaatgaacatgagtgccttggaactg gaggactctgctatgtacttctgtgccagctctctcggaggatgggct gagcagttcttcggacca
```

The amino acid sequence of the variable region of the beta chain may be comprised of SEQ ID NO: 52:

```
                                    (SEQ ID NO: 52)
MSNTVLADSAWGITLLSWVTVFLLGTSSADSGVVQSPRHIIKEKGGRS

VLTCIPISGHSNVVWYQQTLGKELKFLIQHYEKVERDKGFLPSRFSVQ

QFDDYHSEMNMSALELEDSAMYFCASSLGGWAEQFFGPGT.
```

However, one skilled in the art will appreciate that regions of the TCR outside the variable region can be modified without changing the specificity of the TCR.

The nucleotide sequence of the cd3 region of the beta chain may be comprised of SEQ ID NO: 48:

```
                                    (SEQ ID NO: 48)
tgtgccagctctctcggaggatgggctgagcagttcttc
```

The amino acid sequence of the cd3 of the beta chain may be comprised of SEQ ID NO: 51:

```
    CASSLGGWAEQFF.             (SEQ ID NO: 51)
```

However, one skilled in the art will appreciate that regions of the TCR outside the cdr3 region can be modified without changing the specificity of the TCR.

The beta chain sequence, variable region and cdr3 region are not limited to the above embodiments. Rather, they may be comprised of any embodiment that is homologous to or a variant of the above sequences. In other words, the beta chain may be comprised of any sequence that is either homologous to or a variant of SEQ ID NO: 50 and/or SEQ ID NO: 53. The variable region on the beta chain may be comprised of any sequence that is either homologous to or a variant of SEQ ID NO: 49 and/or SEQ ID NO: 52. Finally, the cdr3 region on the beta chain may be comprised of any sequence that is either homologous to or a variant of SEQ ID NO: 48 and/or SEQ ID NO 51. Each of the above possibilities may represent separate embodiments of the present invention.

In a further embodiment, the present invention relates to a method of adoptive T cell therapy for treating a onconeural-expressing carcinoma. Various adoptive T cell therapeutic strategies are contemplated in light of the present invention. In one embodiment, CTL populations may be acquired from a subject, such as from an autologous human lymphocyte population, and tested for its structural and/or functional avidity to any one of the immunodominant cdr2 or HuD peptides of the present invention. The structural and/or functional avidity of a CTL may be tested using any immunological assay understood in the art to detect an antigen specific TCR. For example, the immunological assay may test for immunostimulating cytokines, such as IFN-γ, produced when the TCR is stimulated in response to detecting a cdr2 or HuD peptide. Additionally, the immunological assay may be comprised of tetramer staining as discussed in the Examples below.

Once isolated, the CTL line may be stimulated to elicit an immune response by in vitro exposure to a cell population of APCs displaying the appropriate cdr2 or HuD peptide/MHC complex. These stimulated CTL may then be reintroduced into the subject so as to elicit an effective cell mediated immune response against the targeted onconeural tumor cells, while being tolerogenic and reducing the risk of a secondary PND.

In an alternative embodiment, the CTL that recognizes any one of the cdr2 or HuD peptides may be isolated in accordance with the foregoing and the alpha and beta chains of the CTL's TCR isolated and sequenced according to any protein/nucleic acid isolation and sequence methods understood in the art. Once isolated, the nucleic acid sequence or protein sequence encoding both chains of the TCR may be transfected into a CTL cell, such as an autologous cell line, so as to engineer the CTL to bind to and elicit a cell mediated response to onconeural antigen expressing tumor cells. These engineered CTLs may then be stimulated to proliferate and elicit and immune response in accordance with the foregoing and administered into the subject so as to promote regression of the onconeural antigen expressing tumor cells, while being tolerogenic and reducing the risk of a secondary PND.

As illustrated in Examples section below, the TCR alpha and beta chains may be transfected into the CTL as an mRNA molecule. More specifically, the isolated TCR nucleic acid sequence may be transcribed into an mRNA molecule which may be transfected into the CTL. To this end, the mRNA is translated and presented on the cell surface of the CTL. The CTL is, thereby, competent to recognize and facilitate an immunological response, upon reintroduction into the subject, to a onconeural antigen expressing cancer cell.

The present invention is not limited to transfecting a mRNA molecule. Rather, any nucleic acid sequence or TCR proteins encoding a onconeural antigen specific TCR may be transfected such as, but not limited to, a single stranded DNA molecule, a double stranded DNA molecule, a cDNA molecule, mRNA, or any other nucleotide understood in the art to encode for a antigen specific TCR. Moreover, the present invention is not limited to transfecting a naked nucleic acid sequence molecule into the lymphocyte. Rather, any nucleic acid sequence encoding a onconeural specific TCR may be inserted into a viral vector, such as a retroviral vector, lentiviral vector, a DNA viral vector, a bacterial plasmid vector, or any other vector understood in the art to express a TCR protein within a lymphocyte such as a CTL.

The method of "contacting" a TCR with a CTL is not limited to transfection. Rather, the TCR may be inserted into the CTL by any method understood in the art to introduce a nucleotide and/or peptide into a lymphocyte such as, but not limited to, liposomal attachment, direct injection into a CTL such as microinjection, culturing the lymphocytes in a cdr2 or HuD based culture medium, transfection, transduction, transformation, conjugation, electroporation, endocytosis, phagocytosis, direct administration to a subject, or any other method understood in the art to introduce a nucleotide and/or peptide into a cell.

In a further embodiment, the engineered CTL may tested for efficacy using any technique known in the art. In one embodiment, the engineered CTL may be tested using and immunological assay, such as ELISPOT, wherein the assay measures for the immunological reactivity of the TCR toward the targeted antigen. The present invention is not limited to an ELISPOT assay and alternative methods for testing the efficacy of transfected CTL are well known in the art, and include, but are not limited to, FACS analysis, ELISPOT assays (e.g. IFN-γ), Cr-release assays, tumor regression assays, and detection of tumor-infiltrating lymphocytes. Such methods are described in Zhao et al. *Mol. Ther.* 13 151-159 (2006) and Zhao et al. *J. Immunol.* 174 4415-4423 (2005) the contents of which are incorporated by reference.

In a further embodiment, the engineered CTL of present invention is administered to a subject using standard means known in the art. The CTL may be administered to the subject in any one of several routes including, but not limited to, intravenous, intramuscular, subcutaneous, intradermal, intraperitoneal, intrathecal, intrapleural, intrauterine, rectal, vaginal, topical, intratumor, transmucosal, transdermal, oral, or any other method understood in the art to introduce an immunogenic composition into a subject. Additionally, the CTL may be administered by any of the pharmaceutical compositions discussed below.

In a further embodiment of the present other embodiment, the present invention provides a method of diagnosing an onconeural antigen expressing carcinoma and/or a PND in a subject. More specifically the present embodiment of the invention comprises the steps of detecting within a lymphocyte population of a subject a cdr2-specific T cell receptor (TCR) or a HuD-specific T cell receptor. To this end, a lymphocyte population may be isolated from a subject displaying neurological symptoms consistent with an onconeural antigen carcinoma or PND, and the lymphocyte population may be tested for structural and functional avidity toward any one of the cdr2 antigen/MHC tetramers or HuD antigen/MHC tetramers disclosed above using any immunological assay which tests for immunological responsiveness to an antigen. A positive reaction of the CTL to any of these antigens provides an indication that the subject has previously mounted an immunological response to a onconeural expressing tumor cell and, therefore, is an indicated that such a cell population was present within the subject. Moreover, because of the known correlation of PNDs with onconeural expressing carcinomas tumors, a positive result is an indication of a PND.

In another embodiment, the present invention provides a method of treating an onconeural antigen expressing carcinoma and/or a PND within a subject. More specifically, the method of this embodiment comprises the step of contacting a lymphocyte-containing cell population of the subject, utilizing any of the methods described herein, with a composition of any of the cdr2 or HuD antigens of the present invention and, optionally, a neurological disease preventing adjuvant. The cdr2 or HuD peptide(s) may be processed within the antigen presenting cell and presented on the surface of the antigen presenting cell for recognition a cdr2-specific or HuD-specific CTL. Most preferably, the CTL population recognizes a specific epitope of the onconeural protein that facilitates regression of the carcinoma while minimizing, if not eliminating, the autoimmune PND effect. Accordingly, the present method, in turn, leads to the autoregulation of the stimulated lymphocyte population and, ultimately, promotes regression of the carcinoma and a reduction of the immune response causing damage to the neurons.

The method of contacting a lymphocyte population with the immunogenic composition may occur in vivo wherein the immunogenic compositions of any of the above embodiments may be administered to a subject in one of several routes including, but not limited to, intravenous, intramuscular, subcutaneous, intradermal, intraperitoneal, intrathecal, intrapleural, intrauterine, rectal, vaginal, topical, intratumor, transmucosal, transdermal, oral, or any other method understood in the art to introduce an immunogenic composition into a subject. Additionally, the immunogenic composition may contact a lymphocyte population using any of the pharmaceutical compositions discussed below.

The method of contacting a lymphocyte population with an immunogenic composition may also occur ex vivo wherein a lymphocyte population, which may be autologous, is contacted with the immunogenic composition outside of the subject, and reintroduced into the subject. For example, the lymphocyte population may be contacted with the immunogenic composition by culturing the lymphocytes in a medium containing any of the immunogenic compositions discussed above. The present invention is not limited to autologous lympocytes populations as disclosed above and may be comprised of any lymphocyte population immunologically compatible with the subject. Methods for ex vivo immunotherapy are well known in the art and are described, for example, in Davis I D et al. *J Immunother.* 2006 September-October; 29(5):499-511 and Mitchell M S et al., *Cancer Immunol Immunother.* Jul. 28, 2006, the contents of which are incorporated herein by reference.

In another embodiment, the present invention provides a kit comprising, in any combination a peptide comprised of a cdr2 antigen or a HuD antigen, a cdr2 or HuD antigen nucleic acid sequence, a cdr2 or HuD specific TCR, a cdr2 or HuD antigen specific TCR nucleic acid sequence, and/or a cdr2/HuD antigen expressing antigen presenting cell utilized in performing a method of the present invention.

EXPERIMENTAL DETAILS SECTION

Cdr2 Materials And Experimental Methods

Clinical Case Histories

Patient 1: A 74 year old woman (patient NA-06-03) with a distant history of breast cancer in 1977 (30 years previously) treated with modified radical mastectomy and chemotherapy (CMF, tamoxifen and BCG) developed ascending numbness in all 4 extremities in February 2005. By September 2005 the patient had developed a partial left foot drop, malaise with weakness, and falls, and was found to be Yo antibody positive (Athena Diagnostics, confirmed by Western blot against cdr2 fusion protein). Further workup revealed a CA125 level of >2000 and CT of the abdomen/pelvis showing a 5×2.7 cm mass and retroperitoneal lymphadenopathy, found by needle biopsy to be a poorly differentiated papillary serous carcinoma. Neurologic examination in March 2006 revealed some distal leg weakness with trace knee jerks, absent ankle jerks, decreased pinprick and vibratory sensation in all 4 extremities, and a flat-footed proprioceptive gait in which she was able to walk only 3 or 4 steps independently. At this time, samples were obtained for this clinical study, and she was treated with tacrolimus, 0.3 mg/kg/d, and prednisone, 60 mg/d16, and showed significant improvement over the course of ten days, with improved subjective sensation, and an improved gait that was independent, including the ability to turn independently. She also underwent chemotherapy with carboplatin and taxol. On July 2006 the patient underwent a TAH/BSO; no tumor cells were found on careful pathologic examination, and follow-up PET scan on August 2006 was negative. At last follow-up in December 2006 the patient remained without evidence of tumor, and with continued improvement in symptoms; she was not dysarthric, had trace nystagmus on lateral gaze, 2/5 left dorsiflexor weakness but otherwise intact segmental motor exam, mild decrease in pinprick sensation in all 4 extremities with dropped reflexes, no evident appendicular dysmetria or dysdiadokokinesia, and was able to walk slowly independently with a slightly wide gait.

Patient 2: A 59 year old woman (NA-03-18) presented with sudden onset of falling forward, vertigo and vomiting on Aug. 17, 2003. This resolved after 3 days, but returned September 2003, worsening over 2 days, with difficulty ambulating. Workup revealed Yo antibodies, which prompted a cancer search, which showed a left adnexal mass, leading to a diagnosis of ovarian cancer, stage IIIc. The patient was seen at the hospital on November 2003, and found to have square wave jerks, moderate nystagmus; no dysarthria, normal sensation and reflexes except for absent ankle jerks, and mild dysdiadokokinesia, and a slow, wide-based gate, with imbalance on turns and the inability to tandem gait. On February 2004 the patient developed worsening appendicular and gait ataxia; at this time samples were obtained for this clinical study, and she was treated with tacrolimus, 0.25 mg/kg/d, and prednisone, 60 mg/d with subtle gait improvement and stabilization of symptoms. Her neurologic course was characterized by slow progression over the following 2 years, with symptomatic exacerbations in July 2004, December 2004 and September 2005, and she was treated with tacrolimus/prednisone on each occasion. She has been stable since September 2005; as of December 2006 she has moderate dysarthria, appendicular ataxia that is moderate on the left and mild on the right, and she is unable to walk without assistance; she remains free of evidence of tumor with a CA-125 of 14.

Cdr2 iTopia™ Peptide Screen

A complete peptide library (purchased from Jerini Peptide Technologies (Berlin, Germany) consisting of all possible cdr2 nine-mers was screened for HLA A2.1 binding using the iTopia® screening system (Beckman Coulter Immunomics, San Jose, Calif.). All peptides were at least 80% pure. Data were analyzed with the iTopia™ software using Prism (GraphPad, San Diego, Calif.). All other synthetic peptides were ordered from Invitrogen (Carlsbad, Calif.) or American Peptide Company (Sunnyvale, Calif.) and were determined to be greater than 90% pure. Sequences of the peptides are as follows: human cdr2 (289-297) SLLEEMFLT (SEQ ID NO: 1); murine cdr2 (289-297) SLLEEMFLA (SEQ ID NO: 2); human cdr2 (290-298) LLEEMFLTV (SEQ ID NO: 3); human cdr2 (289-298) SLLEEMFLTV (SEQ ID NO: 4); human cdr2 (273-281) KLVPDSLYV (SEQ ID NO: 5); and FluM1 (58-66) GILGFVFTL[1] (SEQ ID NO: 6).

Cell Lines and Transfectants

EL4-A2/K$^b$ (EA2K$^b$) (obtained from Dr. Linda Sherman, The Scripps Research Institute, La Jolla, Calif.) is a transfectant of the murine thymoma EL4 (H-2$^b$ haplotype) that expresses A2/K$^b$. T2 is a lymphoblastoid cell line (HLA-A2.1$^+$) deficient in TAP function, whose HLA proteins can easily be loaded with exogenous peptides. Other human cell lines used were the Adenovirus (Ad)-5 transformed cell line HEK293 (CRC 1573; American Type Cell Culture (ATCC); Rockville, Md.), the breast carcinoma cell line MCF7 (ATCC), the breast carcinoma cell line SKBR3 (HTB-30; ATTC), and the ovarian carcinoma cell line COV413 (provided by Dr. Victor Engelhard, University of Virginia, Charlottesville, Va.). Other murine cell lines used were the melanoma line B16-F10, and B16.AAD, an AAD stable transfectant of B16-F1 (provided by Dr. Victor Engelhard). The AAD plasmid (provided by Dr. Victor Engelhard) is a hybrid MHC class I molecule that contains the α1 and α2 domains from HLA-A2.1 and the α3 domain of the H-2D$^d$ molecule. The stable AAD-expressing cell lines HeLa.AAD and MCF7. AAD were generated by transfecting HeLa and MCF7 cells, respectively, with the AAD plasmid using Fugene6® (Roche, Indianapolis, Ind.) followed by selection with G418 (Gibco). The HeLa.A2.1 stable transfectant was generated by transfecting HeLa cells by the same method with pA2.1 plasmid (provided by Dr. Paul Robbins, NIH/NCI, Bethesda, Md.).

Culture Media

T2 and COV413 cell lines were maintained in "R10 medium", i.e., RPMI 1640 medium (Mediatech, Herndon, Va.) supplemented with 10% (v/v) FBS (Hyclone, Logan, Utah), 2 mM Glutamax® (Gibco), sodium pyruvate, non-essential amino acids, 15 mM Hepes buffer, 50 μM β-mercaptoethanol, and gentimycin. All other cell lines were maintained in "D10 medium", i.e., DMEM high glucose (Mediatech) containing all of the same supplements as R-10 except for β-mercaptoethanol. Stable transfectants were maintained in the complete medium of the parental cell type supplemented with G418 (Gibco Life Technologies, Grand Island, N.Y.). Cells were washed out of G418-containing media for the 48 hours prior to use in co-culture assays.

Mice

A2.1 transgenic HHD mice were provided by Dr. Francois Lemonnier (Pasteur Institute). They are derived from a strain deficient for mouse β-microglobulin and H-2D$^b$ molecules and transgenic for a chimeric MHC class I molecule, HLA-A0201/D$^b$, linked to human β-microglobulin. AAD mice, which express the α1 and α2 domains from the HLA-A2.1 molecule, and the α3 domain from the murine H-2D$^d$ molecule, and AAA mice, which have fully human A2.1 molecules, were obtained from Jackson Laboratories. AAD transgenic mice were monitored for expression of HLA-A2.1 on peripheral blood cells by flow cytometry using the BB7.2 antibody. Mice were maintained in specific pathogen-free facilities, and all protocols were approved by the Institutional Animal Care and Use Committee.

Recombinant Adenovirus

E1/E3-deleted recombinant adenovirus encoding full-length human cdr2 (Ad-hcdr2), full-length mouse cdr2 (Ad-mcdr2), or full-length influenza matrix protein (Ad-FluM1), were constructed using the AdEasy® vector system. Genes were inserted into the pShuttle-CMV vector multiple cloning site—or no transgene in the case of Ad-GFP—and the resulting plasmid was co-electroporated into BJ5183 E. coli along with the pAdEasy-1 vector to allow for recombination in bacteria. The resulting plasmid was then used to transfect HEK 293 cells. After incubation for 7 days, the cells were frozen and thawed to release the virus; the crude viral lysate was used for further purification following expansion on HEK 293 cells. Adenovirus was purified either by $CsCl_2$ density centrifugation, or using an Adenopure® kit (Puresyn) and frozen at −80° C. until use.

Western Blot Analysis

Tissue culture cells were lysed in Passive Lysis buffer (Promega). Cell proteins were separated by 10% SDS-PAGE and transferred to PVDF membrane (Millipore, Bedford, Mass.). Membranes were blocked for 1 hr at rt (room temperature) in 10% non-fat milk, and incubated with PCD patient antiserum overnight at 4° C. After washing with PBS+ 0.1% Tween, membranes were incubated with 1:10000 rabbit anti-human-HRP (Jackson Immunoresearch) at rt for 1 h. After washing, bound protein was detected by chemi-luminescence (NEN) on Biomax MR® film (Kodak).

Generation of Peptide-Specific HLA-A2.1 Restricted CTL 8-10 wk-old female mice were immunized intradermally in the flank with $10^{10}$ plaque-forming units (pfu) of recombinant adenovirus. As an adjuvant, 400 ng of pertussis toxin (Sigma) was administered intraperitoneally at 0 and 48 h. 12-18 d after immunization, spleens were removed and RBC were lysed with ACK buffer (Biofluids). Cells were plated at $3.5 \times 10^6$ cells/well in a 24 well plate in R-10 media with 0.5 µM free peptide. After 7 to 10 d of culture, and every 9-14 d thereafter, $10^5$ CTL were re-stimulated with $3.5 \times 10^6$ peptide-pulsed (0.5 µM) irradiated (3000 rad) RBC-depleted splenocytes in 24-well plates in R-10 media supplemented with 10 IU/ml IL-2 (Chiron).

Preparation of Primary Murine Kidney Epithelial Cell Cultures

Primary kidney cell cultures were generated by pulverizing mouse kidneys with the back of a syringe, pipetting until a single cell suspension was obtained, and passing the suspension over a 70 µM cell strainer. After washing, cells were cultured in D10 medium in 10 cm tissue culture dishes (Falcon). Cells were fed by replacing medium on days 4 and 7. Between d 7-9, 30 U/ml recombinant murine IFNγ (R&D Systems) was added to the cells to increase surface MHC class I expression. 24 h later, $10^9$ pfu of purified adenovirus was added to each plate. The next day, cells were washed 3 times with PBS and harvested with trypsin EDTA for use in the ELISPOT assay.

Cloning of Murine cdr2-Specific, HLA-A2.1-Restricted TCR-α and TCR-β cDNA

Total RNA was extracted with the RNeasy® kit (Qiagen, Valencia, Calif.) from $2 \times 10^5$ CD8-purified (MACS, Miltenyi Biotech) cdr2-290 clone T cells. Total RNA (1 µg) was used to clone the TCR cDNAs by RACE PCR (GeneRacer kit; Invitrogen Life Technologies, Carlsbad, Calif.). 5'-RACE was performed using the 5' Generacer® primer and 3' primer of gene-specific primer TCR for the TCR α constant region, or C1 or C2 β constant regions. Products were electrophoresed on a gel, and appropriately sized bands were excised and cloned into pCR®4-TOPO vector (Invitrogen Life Technologies). For each of the CTL clones, plasmid DNAs were prepared from 16 individual clones from TCR α-chain cDNA, and 16 clones from TCR β-chain cDNA. Presence of full-length insert of all 64 plasmids was confirmed by bidirectional sequencing. 2 independent 5' RACE PCR reactions were performed for each T cell clone.

Preparation of In Vitro Transcribed mRNA

Gene-specific oligonucleotide primers were generated for the production of in vitro transcribed RNA encoding GFP from pEGFP-N1 (Clontech) and TCR α and β chains. 5' primers included sequence for T7 RNA polymerase binding and transcription, followed immediately by a Kozak sequence, a start codon and the next 16-17 base pairs (bp) of Vα or Vβ region for each TCR gene or EGFP:

```
cdr2-TCRα fwd
                                        (SEQ ID NO: 7)
5'-TAA TAC GAC TCA CTA TAG GGA GAG CCA CCA TGG
ACA AGA TTC TGA CAG C-3';

cdr2-TCRβ fwd
                                        (SEQ ID NO: 8)
5'-TAA TAC GAC TCA CTA TAG GGA GAG CCA CCA TGT
CTA ACA CTG TCC TCG C-3';

EGFP fwd
                                        (SEQ ID NO: 9)
5'-TAA TAC GAC TCA CTA TAG GGA GAG CCA CCA TGG
TGA GCA AGG GCG AGG-3'.
```

3' primers included 64 T residues and 16-25 bp of the relevant β or β constant region sequence or EGFP sequence. Reverse primers were Cα: 5'-(64)T TTA ACT GGA CCA CAG CCT CAG CGT C-3' (SEQ ID NO: 10); C2β: 5'-(64)T TTA GGA ATT TTT TTT CTT GAC CAT GGC C-3' (SEQ ID NO: 11); and EGFP: 5'-(64)T TTA CTT GTA CAG CTC GTC C-3' (SEQ ID NO: 12). The subcloned cDNA in PCR®4-TOPO was used to generate PCR products for in vitro transcription using the above primer sets. Resulting bands were gel purified and used for a second round of PCR amplification, followed by purification on Zymogen DNA columns. T7 mMES SAGE mMACHINE® High Yield Capped RNA transcription Kit (Ambion) was utilized to generate in vitro-transcribed RNA, which was purified using an RNeasy® Mini Kit (Qiagen) and resuspended in RNase-free water at 1-3 mg/ml.

Electroporation of In Vitro-Transcribed RNA

In preparation for electroporation, donor PBMC obtained by leukopheresis were stimulated in vitro at a concentration of $10^6$ PBMC/ml with 50 ng/ml OKT-3 and IL-2 (300 IU/ml, Chiron) in Stemline T cell Expansion medium (CSM; Sigma; St Louis, Mo.) supplemented with 5% (v/v) FBS (Hyclone), Glutamax® (Invitrogen), and gentamycin for 3 days. Following stimulation, cells were enriched for CD8$^+$ T cells by MACS separation (Miltenyi Biotec). Purified CD8$^+$ T cells were cultured for an additional 10-17 days in IL-2 containing medium before electroporation. For TCR electroporation, 2.0 µg of RNA were used per $1 \times 10^6$ cells in Opti-MEM® serum-free medium (Invitrogen Life Technologies), using an ECM 830 Electro Square® Porator (BTX Instrument Division, Mass.). After electroporation, cells were rested for 6-8 h without IL-2 before use in FACS staining or co-culture experiments.

Electroporated T Cell Cytokine Release Assays $1\times10^5$ responder cells (CD4+ or CD8+ T cells) and $1\times10^5$ stimulator cells (peptide-pulsed T2 or Ad-transduced KECs) in were incubated for 18-20 h in a 0.2 ml culture volume in individual wells of 96-well plates. Cytokine secretion was measured in culture supernatants diluted so as to be in the linear range of the assay using an IFN-γ ELISA kit (Endogen) according to the manufacturer's recommendations.

IFN-γ Enzyme-Linked Immunospot (ELISPOT) Murine and Human

Nitrocellulose-bottomed 96-well plates (MultiScreen HA, Millipore) were coated overnight at 4° C. with anti-IFN-γ mAb (clone AN18 at 5 μg/ml for mouse, clone 1-DIK at 10 μg/ml for human; Mabtech). Wells were washed 3 times with PBS and blocked for 2 h with R-10 culture medium at 37° C. For direct ex vivo mouse ELISPOT, CD8+ T cells were isolated by positive selection from spleens using MACS purification and $2\times10^5$ CD8+ T cells were co-cultured with $5\times10^4$ stimulator cells. For ELISPOT with CTL lines or clones, $1\times10^4$ CD8+ T cells, purified by negative selection using a mouse CD8 isolation kit (Miltenyi Biotec), were co-cultured with $5\times10^4$ stimulator cells. For human ELISPOT with RNA-electroporated human PBL, $1\times10^5$ CD8+ T cells were co-cultured with $5\times10^4$ irradiated stimulator cells. After incubation for 18 h at 37° C., plates were washed 6 times with PBS+0.05% Tween-20. Biotinylated IFN-γ mAb (clone R4-6A2 for mouse, Pharmingen; clone 7-B6-1 for human, Mabtech), the conjugate (avidin-peroxidase complex; Vectastain avidin-biotin complex method Elite Kit; Vector Laboratories) and AEC substrate (Sigma) were then used for spot development. All conditions were performed in duplicate or triplicate wells, as indicated. Colored spots representing IFN-γ-releasing cells are depicted as spot-forming-cells (SFC) per $10^6$ cells. ELIPSOT plate evaluation was performed in a blinded fashion by an independent evaluation service (Zellnet Consulting) using an automated ELISPOT reader (Carl Zeiss) with KS Elispot 4.8 software.

Tetramer Staining

PE-labeled cdr2(290-298)/HLA-A2.1, cdr2(289-297)/HLA-A2.1, FluM1(58-66)/HLA-A2.1, PSMA(4-12)/HLA.A2.1 and negative tetramer/HLA-A2.1 were purchased from Beckman Coulter Immunomics. Human cells were stained in a FACS buffer (PBS, 1% (v/v) FBS (Hyclone), and 1% (v/v) PHS; supplemented where indicated with 0.02% $NaN_3$). For tetramer staining of human PBMC or electroporated CD8+ T cells, $1.0\times10^6$ cells were incubated with 1:20 dilution of tetramer for 20 minutes at room temperature. Antibody to CD8 was then added for an additional 10 minutes. For tetramer staining of murine CTL, CD8+ T cells were purified by negative selection (MACs; Miltenyi Biotec) and incubated for 20 minutes on ice in Fc block (BD Pharmingen) in a FACS buffer composed of PBS, 5% (v/v) FBS (Hyclone), 5% (v/v) normal goat serum, and 1% (v/v) PHS. For tetramer staining $2\times10^5$-$1.0\times10^6$ murine cells were incubated with tetramer for 20 minutes in FACS buffer at room temperature. Where indicated, antibody to CD8 was then added to the cells during the final 10 minutes. All human and murine cell samples were washed and analyzed immediately. Cells were gated on the CD8+ population. Data was collected on a FACScaliber (Becton Dickinson) and analyzed using Flowjo® software (Treestar).

CD107a Assay $10^5$ tumor cells were placed into 1 well of a 24-well plate along with $10^5$ TCR mRNA-electroporated or mock-electroporated CD8+ T cells in a total volume of 1 mL. 20 μL of FITC-conjugated CD107a antibody and 1 μl of GolgiStop® (Becton Dickinson) were added to the well. Cells were incubated for 4 h at 37° C., washed, and analyzed by flow cytometry.

Example 1

Identification of cdr2 Peptides that Bind to HLA-A2.1

A comprehensive unbiased screening approach was utilized to identify cdr2 peptides capable of binding with high affinity to HLA-A2.1. A complete library of 446 overlapping human cdr2 peptide nonamers was assayed for binding to HLA-A2.1 plate-bound monomers. Peptides binding at a level of greater than 30% of the positive control were further characterized by determining their affinity for HLA-A2.1 over a range of peptide concentrations ($10^{-4}$-$10^{-9}$M), and by an off-rate assay to determine the relative stability of the resulting MHC/peptide complex. Peptides were ranked by a net score that integrated the peptide binding score, the $ED_{50}$, and the half-life for the MHC/peptide complex for each peptide to plate bound HLA-A2 molecules (iTopia™ iScore). A peptide corresponding to residues 290-298 ("cdr2(290-298)"; LLEEMFLTV; SEQ ID NO: 1) was the best binding peptide (Table 1).

Thus, a previously uncharacterized cdr2 peptide was identified with high affinity for HLA-A2.1.

Example 2

Generation of High-Affinity Human cdr2(290-298)-Specific CTL In A2.1 Transgenic Mice HLA class I transgenic mice were utilized to identify a high affinity T cell receptor (TCR) specific for human cdr2. The immunogenicity of human cdr2 in mice was evaluated by immunizing AAD HLA-A2.1 transgenic mice with recombinant adenovirus expressing full-length human cdr2 (Ad-hcdr2). Robust ex vivo CD8+ T cell responses (frequency>0.3%) specific for cdr2(290-298) were obtained in all mice immunized with either Ad-hcdr2 (FIG. 1B) or human cdr2(290-298) peptide; less robust responses were seen to 6 other peptides A cdr2(290-298) peptide specific CTL line ("AAD 290") was generated from an Ad-hcdr2-immunized AAD mouse. AAD 290 CTL recognized with high avidity T2 cells pulsed with human cdr2(290-298), but not murine cdr2(289-298) or FluM1 peptide (derived from the influenza matrix protein) in IFN-γ ELISPOT assays (FIG. 1C). In addition, the human decapeptide cdr2(289-298), which overlaps cdr2(290-298) but is extended N-terminally by 1 residue, was recognized by AAD 290 CTL as efficiently as the nonamer (FIG. 1C). A small but reproducible cross-reactivity to human cdr2(289-297) was observed, but this response was 100-fold lower than the response to cdr2(290-298), and was absent at concentrations of peptide lower than $10^{-6}$M. Thus, the cdr2(290-298)-HLA-A2.1 complex is recognized with high avidity by T cells.

Figure 1D:
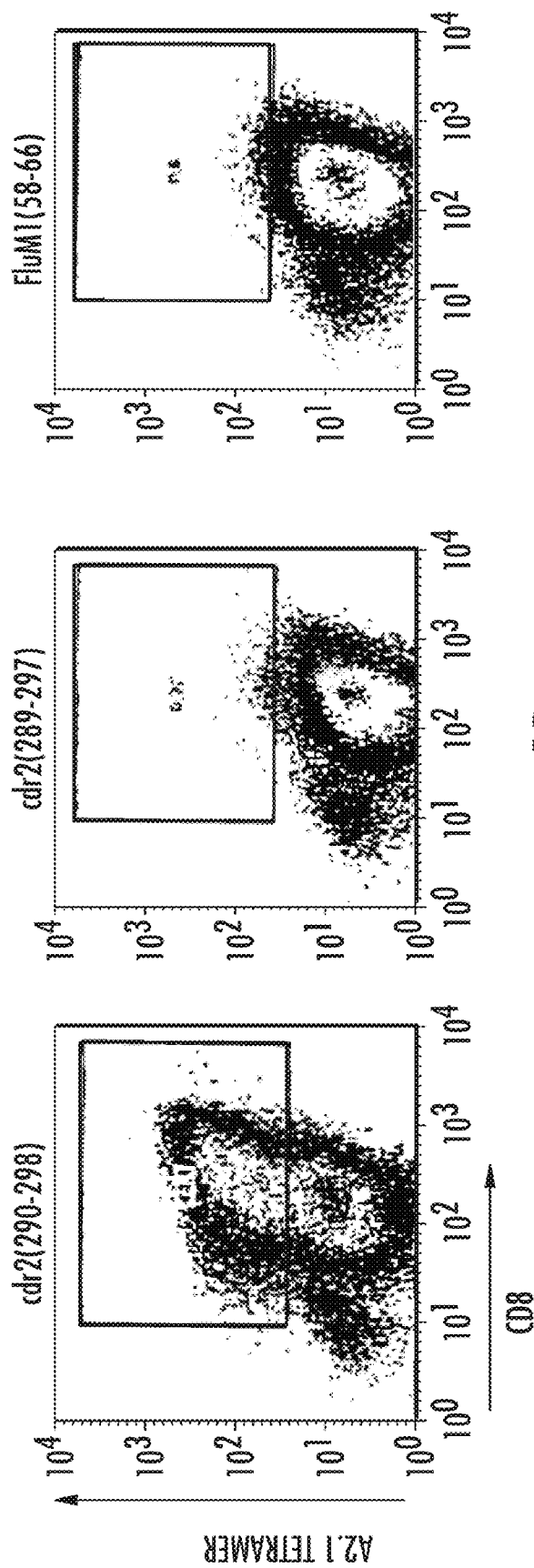

Binding to a cdr2(290-298) A2.1 tetramer was measured as another indication of the high avidity of these AAD 290. Since murine CD8 does not interact with the α3 domain of the A2.1 molecule, binding of murine CTL by A2.1 tetramers is generally CD8-independent; therefore high affinity TCR-MHC/peptide interactions are preferentially observed. A large proportion (~40%) of AAD 290 CTL were able to bind to A2.1/cdr2(290-298) tetramers; the specificity of these results was shown by lack of binding of AAD 290 CTL to cdr2(289-297) or FluM1 A2.1 tetramers (FIG. 1D). These results confirm the ELISPOT results.

Thus, cdr2(290-298) is capable of binding HLA-A2.1 and eliciting generation of high-affinity, antigen-specific, cytokine-secreting T cells.

Example 3 cdr2(290-298) Peptide is Naturally Processed and Recognized in Tumor Cells

Figure 2:
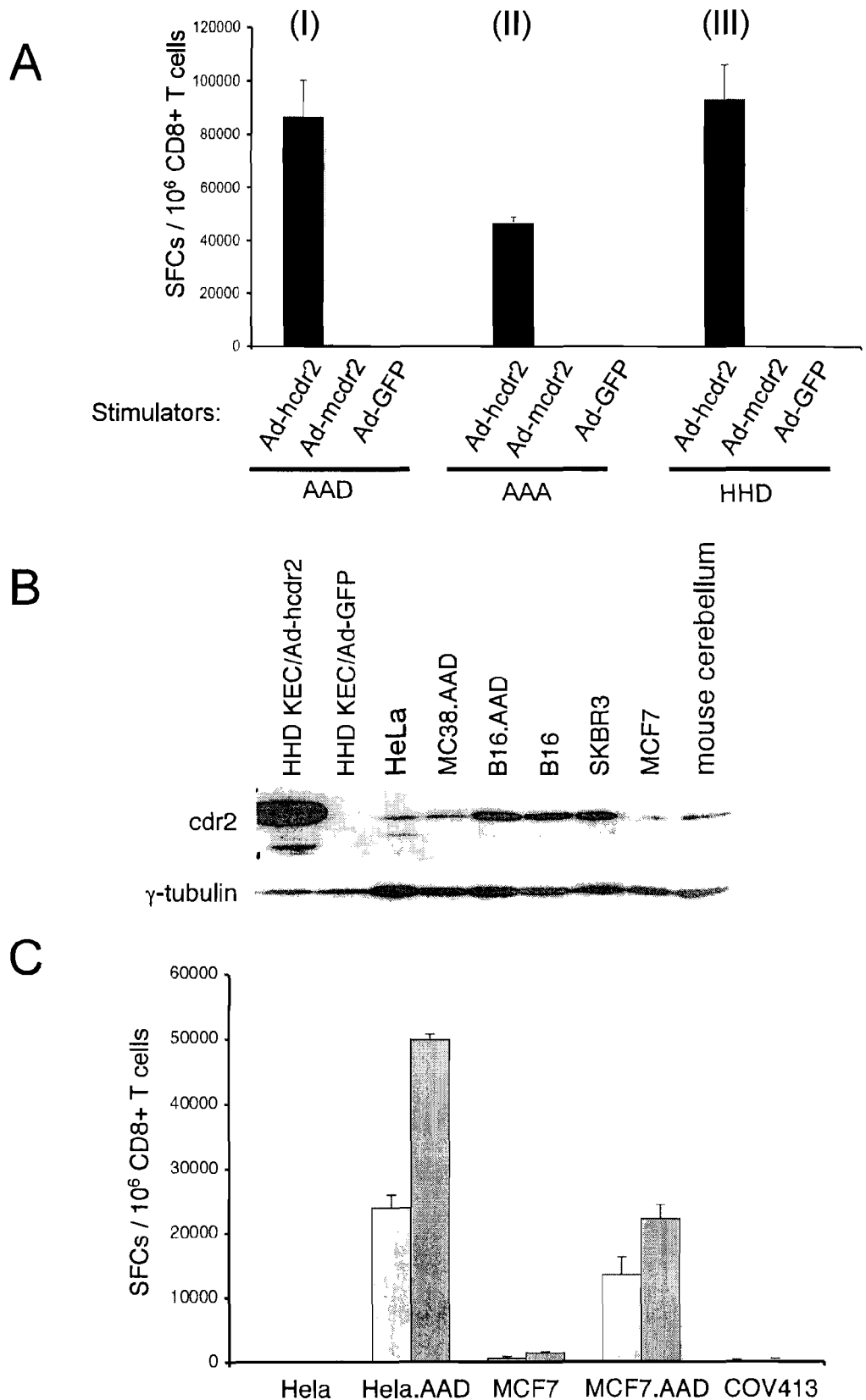
FIG. 2. AAD 290 CTL recognize endogenous cdr2. (A) AAD 290 CTL were co-cultured with KEC isolated from either AAD (I), AAA (II), or HHD (III) mice; KECS were infected with Ad-hcdr2, Ad-mcdr2, or Ad-GFP and used as stimulators in an 18 h IFN-γ ELISPOT assay as in FIG. 1. (B) Western blot analysis of cdr2 protein expression tumor cell lines and normal tissue. No cdr2 was detected in KEC mock transduced with Ad-GFP, but was seen in Ad-hcdr2 transduced KEC, mouse cerebellum, and all tumor cell lines tested. (C) AAD 290 CTL recognize endogenous cdr2 in tumors. AAD 290 CTL were co-cultured with HeLa, HeLa.AAD, MCF7, MCF7.AAD, or COV413 tumor cells plus (grey) or minus (blue) pretreatment with IFN-γ for 40 h in an 18 h IFN-γ ELISPOT assay.

To confirm that cdr2(290-298) is naturally processed, the next experiment examined the ability of the AAD 290 CTL line to respond to HLA A2.1 transgenic mouse kidney epithelial cells (KEC) transduced with Ad-hcdr2 in an IFN-γ ELISPOT assay. KEC do not produce endogenous cdr2 protein. AAD 290 CTL produced IFN-γ in response to co-culture with KEC transduced with Ad-hcdr2, but not with control KEC infected with Ad-mcdr2 or Ad-GFP (FIG. 2A). Recognition of Ad-hcdr2-infected HHD KEC, which have no mouse MHC molecules (FIG. 2A (III)), showed that this response was A2.1 restricted. Furthermore, AAD 290 CTL responded to Ad-hcdr2 infected KEC derived from AAA mice, which have a human α3 domain, showing that they were capable of CD8-independent recognition of endogenous human cdr2. Thus, AAD 290 CTL recognized naturally processed cdr2 protein presented on human HLA A2.1 molecules.

To confirm that the cdr2(290-298) peptide is also naturally processed and presented by human cells containing antigen processing machinery, AAD 290 CTL were tested for recognition of physiologic levels of endogenous cdr2 in human tumor cells. First, a number of tumor cell lines were evaluated for cdr2 expression, including the breast cancer cell lines MCF7 (A2.1 positive) and SKBR3; the cervical carcinoma cell line, HeLa (A2.1 negative); and an ovarian carcinoma cell line, COV413 (A2.1 positive). All cell lines tested showed cdr2 expression by Western blot analysis, as did mouse cerebellum and KEC cells transduced with Ad-hcdr2, while primary cultures of kidney epithelial cells did not (FIG. 2B).

Ability of human tumor cells to stimulate IFN-γ secretion by AAD 290 CTL was tested by ELISPOT assay. AAD 290 CTL exhibited small but consistent responses to MCF7 cells (1350+/−212) but not HeLa cells (150+/−212 SFCs) (FIG. 2C). To facilitate recognition of these human cells by the murine AAD 290 CTL, the murine α3 molecule was supplied to MCF7 and HeLa by stable transfection with the AAD molecule. The resulting cell lines, HeLa.AAD and MCF7.AAD, elicited larger responses in the ELISPOT assay with AAD 290 CTL (FIG. 2C), while there was no response to KEC expressing the AAD molecule in the absence of cdr2 antigen (FIG. 2A). Moreover, specific recognition of cdr2 in tumor cell targets was enhanced by pre-treating cells with IFN-γ, a cytokine known to facilitate target recognition by increasing MHC class I expression, antigen processing, and ICAM expression (FIG. 2C). Both treated and untreated A2.1 negative HeLa cells were not recognized, confirming that target recognition was A2.1 restricted.

Thus, AAD 290 CTL are capable of recognizing endogenous cdr2 expressed in tumor cells, demonstrating that the cdr2(290-298) peptide is processed and presented by human cells.

Example 4

Tetramer Analysis of Human CD8+ T Cells

Figure 3A:
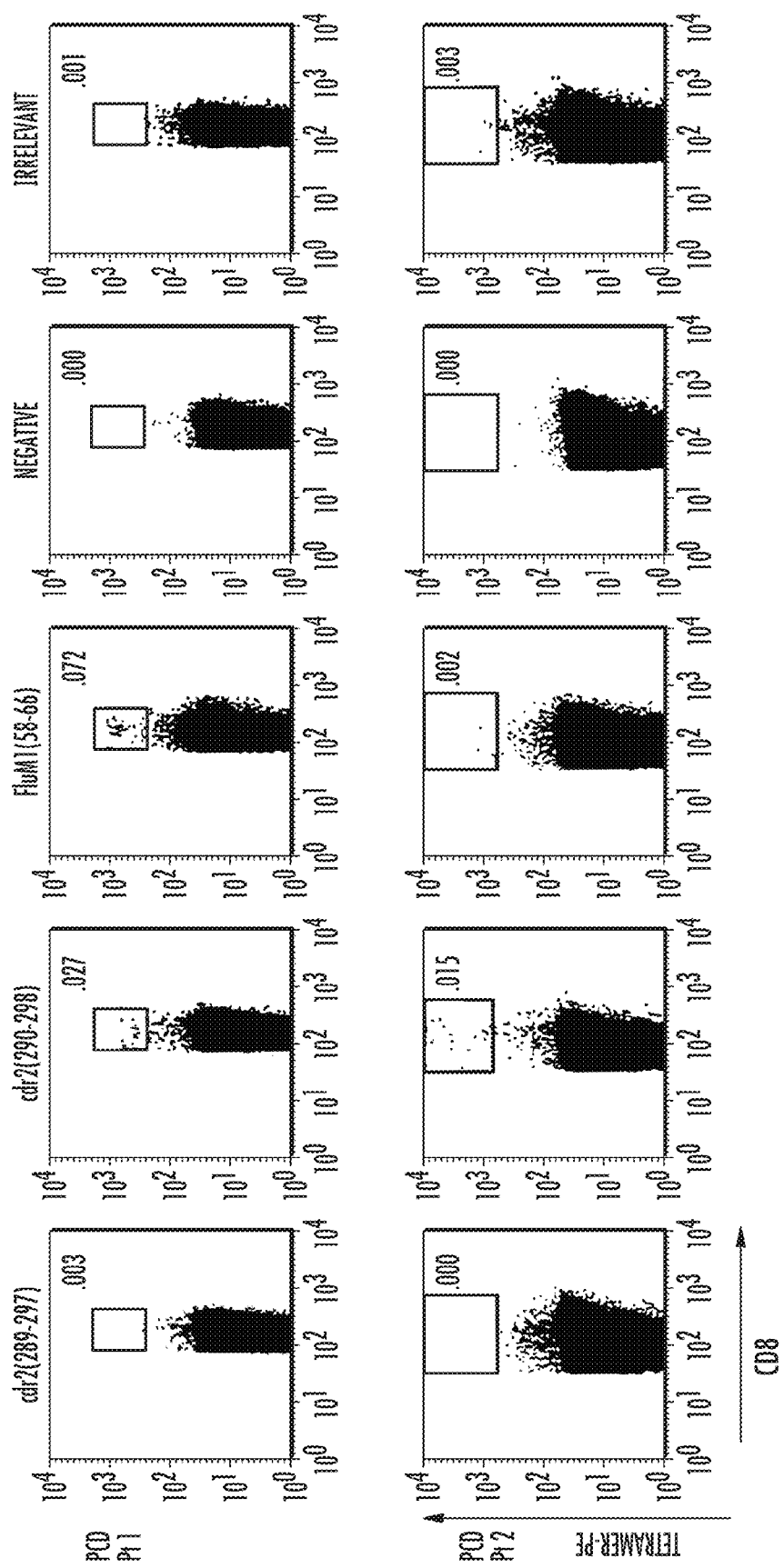
FIG. 3. Tetramer analysis of human CD8$^+$ T cells in HLA-A2.1$^+$ PCD patients. (A) Tetramer analysis of PBMC from 2 A2.1$^+$ PCD patients. PBMC were stained with cdr2(290-298) SEQ ID NO: 1, FluM1(58-66), irrelevant (PSMA(4-12) in PCD patient 1, or HuD(157-165) in PCD patient 2), or negative (as supplied by Beckman Coulter) A2.1 tetramers together CD8 antibody, and analyzed by flow cytometry. Results are gated on CD8$^+$ T cells. (B) Tetramer analysis of control patients (Ctl Pt I-IV). A2.1/cdr2(290-298) tetrameric complexes did not stain PBMC from a normal donor (I), 2 patients with the Hu syndrome (II and III), or 1 neurologically normal ovarian cancer patient (IV). For control and comparison PBMC were stained with FluM1(58-66), CMVpp65 (495-503), or negative A2.1 tetrameric complexes.
Figure 3B:
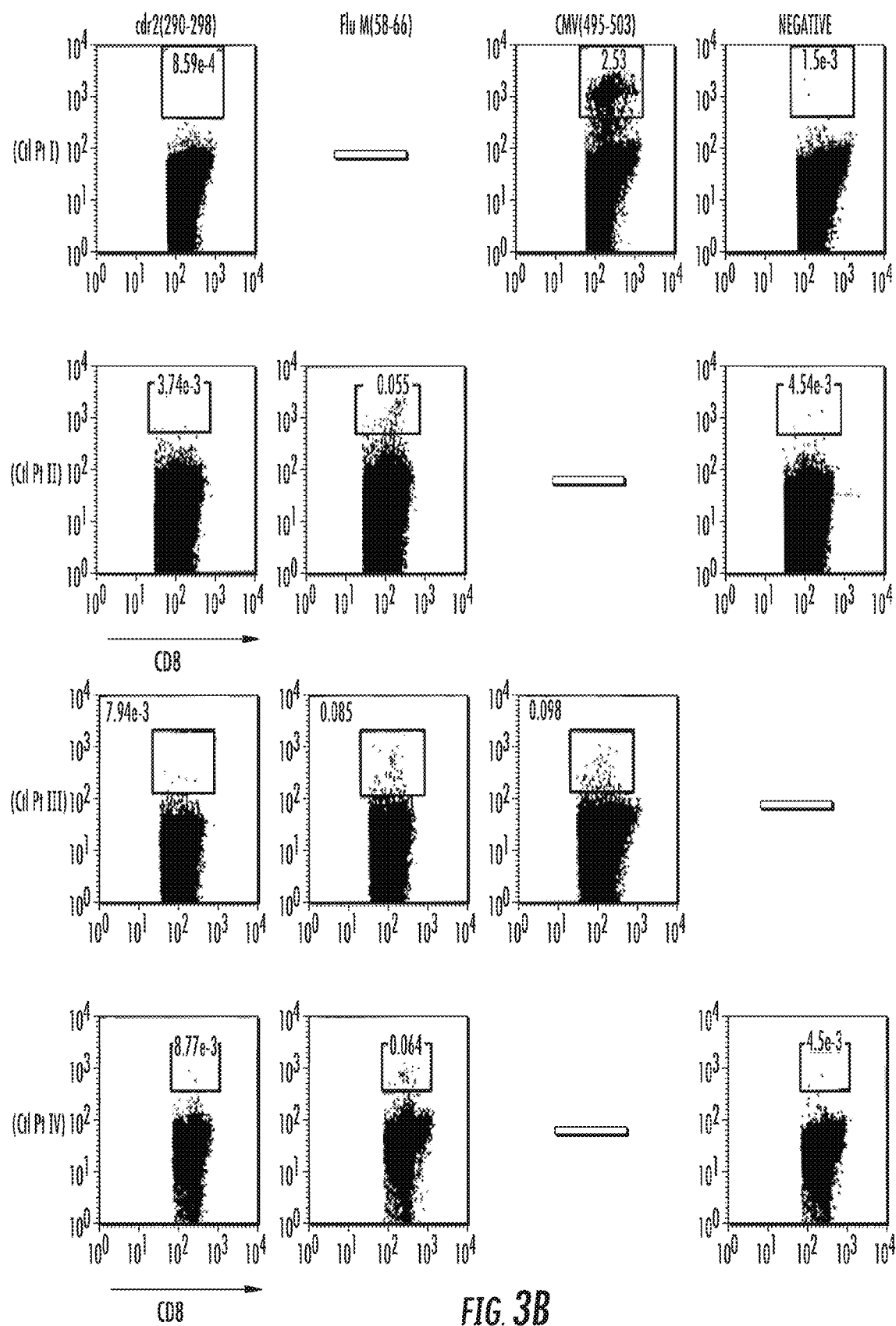

To test the relevance of the cdr2(290-298) epitope for patients with PCD, the A2.1/cdr2(290-298) tetramer was used to examine peripheral blood CD8+ T cells obtained from 2 A2.1+ PCD patients available for study from among 10 PCD patients. (A third patient in this group was A2.1+; this patient's PBMC were examined 4 months after neurologic deterioration and gave less robust tetramer staining results; data not shown). For control and comparison, additional tetramer analysis was performed using commercially available negative tetramers (Beckman Coulter), HLA-A2.1/FluM1 (58-66) tetramers, or irrelevant tetramers. Peripheral blood from A2.1+ PCD patients harbored significant populations of T cells able to bind the cdr2(290-298) tetramer (0.027 to 0.015% of CD8+ T cells; FIG. 3A), but not a negative tetramer (0% of CD8+ T cells) or irrelevant tetramers (0.001-0.003% of CD8+ T cells). For comparison, PCD patient 1 had a discreet population of FluM1 tetramer-staining peripheral blood CD8+ T cells (0.072%), which was correlated with a FluM1 (58-66) peptide-specific memory CD8+ T cell response as determined by direct IFN-γ ELISPOT assay (PCD patient 2 did not exhibit a flu response). The cdr2 tetramer staining was specific to PCD patients; as shown by lack of staining of several control A2.1+ patient T cell samples, including a normal donor (FIG. 3B, I); 2 patients with the paraneoplastic Hu syndrome (FIGS. 3B, II and III); and a neurologically normal ovarian cancer patient (FIG. 3B, IV).

Thus, cdr2(290-298) is a naturally processed and presented CTL epitope in humans, and plays a significant role in immunity to breast and ovarian cancer.

Example 5

Cloning and Characterization of cdr2(290-298) Specific T Cell Receptors

Figure 4A:
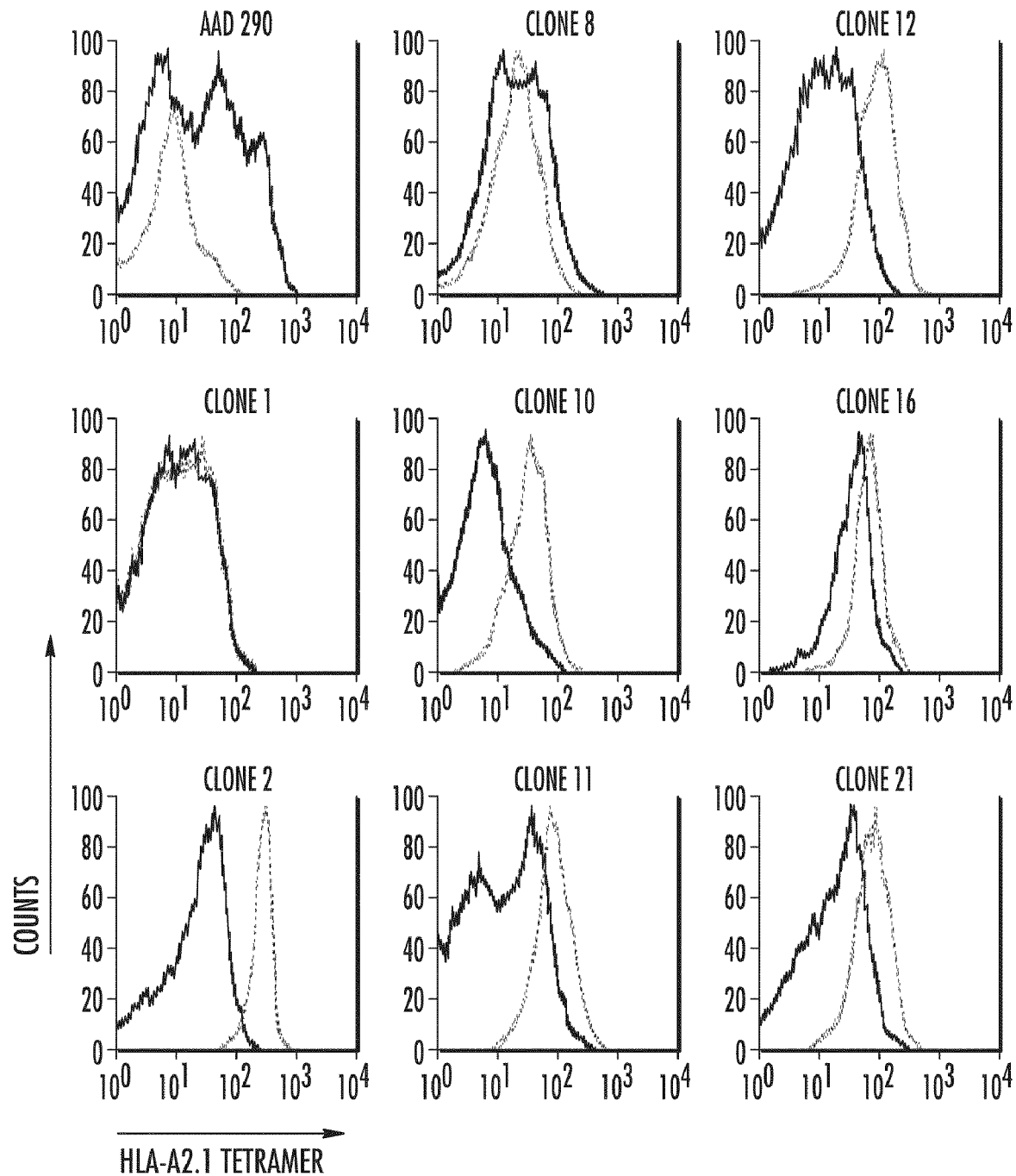
FIG. 4. Structural and functional avidity of the cdr2-specific T cell clones. (A) CD8$^+$ T cells from the AAD 290 CTL line (after the 6th in vitro restimulation) and 8 daughter CTL clones were stained with A2.1/cdr2(290-298) (SEQ ID NO: 1) tetramer (red line) or with the negative control tetramers A2.1/cdr2(289-297) (SEQ ID NO: 3) (blue line) and A2.1/FluM1(58-66) (green line) and analyzed by flow cytometry. (B) The ability of bulk AAD 290 CTL or the indicated clones to recognize human cdr2(289-297) (SEQ ID NO: 3) or cdr2 (290-298) (SEQ ID NO: 1) peptide-pulsed T2 cells ($10^{-6}$M) or the indicated cdr2-expressing tumor cells (pretreated with IFN-γ for 40 h) was evaluated in an 18 h IFN-γ ELIPSOT assay as in FIG. 1.
Figure 4B:
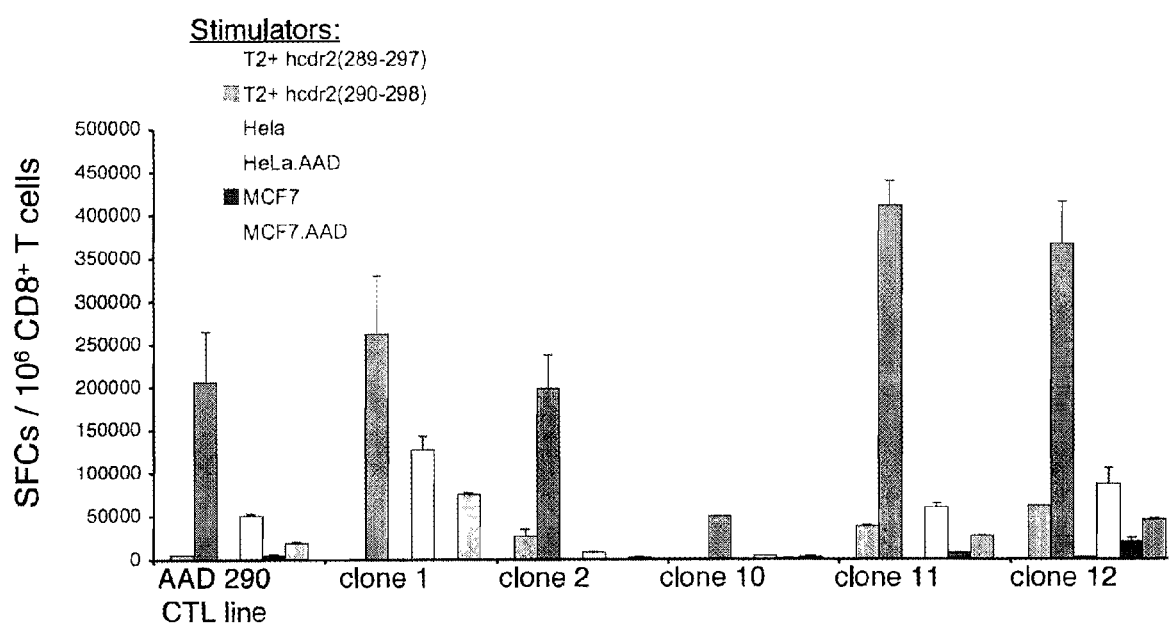

Genes encoding a cdr2-specific T cell receptor were then cloned and characterized. Individual clones from the AAD 290 CTL line were screened by measuring their structural and functional avidity. cdr2(290-298)-specific CTL clones were isolated by limiting dilution of the AAD 290 CTL line. Clones were analyzed for ability to bind cdr2(290-298) tetramer (FIG. 4A) and produce IFN-γ in response to cdr2(290-298) peptide-pulsed T2 cells or human cdr2-expressing tumor cell lines (HeLa or MCF-7 cells; FIG. 4B). A range of T cell receptors (TCR) were identified, with clones 11 and 12 exhibiting both high binding affinity and functional avidity. TCR from 4 clones were isolated by 5'RACE PCR and sequenced; clones 11 and 12 contained an identical TCR (FIG. 5A-B), which was analyzed in greater detail.

Figure 6A:
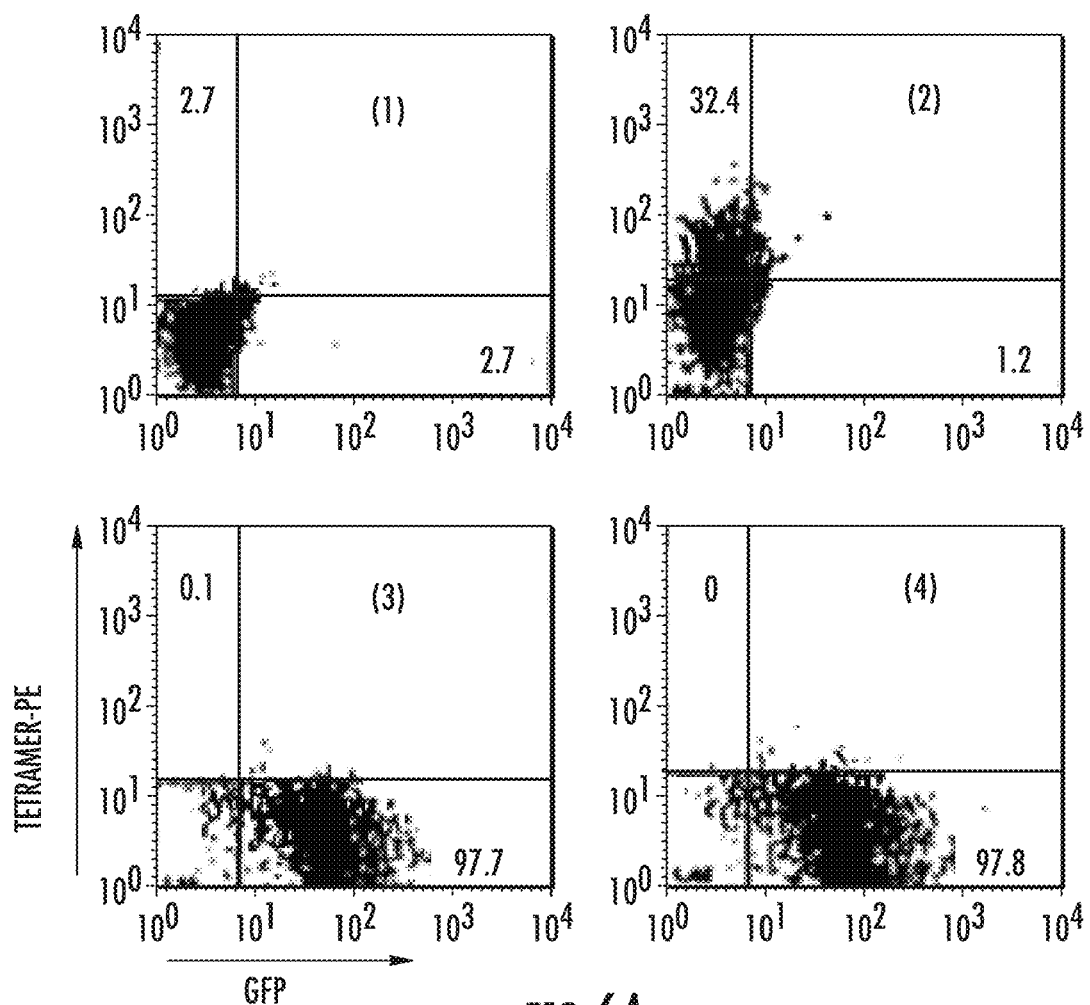
FIG. 6. Characterization of a clone encoding a cdr2-specific T cell receptor. (A) Tetramer analysis of CD8$^+$ PBL electroporated with cdr2-TCR mRNA. 2 μg cdr2 TCRα- and β-chain (1 and 2) and GFP RNAs (3 and 4)/1×10$^6$ cells were electroporated into OKT3 stimulated CD8+ PBMC, prepared as described in Methods. Cells were analyzed by flow cytometry after staining with (1 and 3) a non-specific negative tetramer, with HLA-A2.1/cdr2(290-298) (SEQ ID NO: 1) tetramer (2 and 4), and percentage of cells staining shown. (B-F) Functional analysis of cdr2 TCR. Human CD8$^+$ T cells were electroporated with cdr2 TCR as above were co-cultured for 18 h with target cells (T2 cells pulsed with the indicated concentrations of specific peptide (cdr2 290-298 (SEQ ID NO: 1); triangles; cdr2 289-298 (SEQ ID NO: 39); squares) or nonspecific peptide (cdr2(289-297) (SEQ ID NO: 3), crosses; FluM1, diamonds (B) or KECs transduced with the indicated Adenoviral constructs (C), and the concentration of IFN-γ secreted into the medium was measured by ELISA. Values are the average of duplicate wells. In (B), IFN-γ secretion in co-cultures with GFP electroporated CD8+ T cells was <15 pg/ml for all peptides. (D) The cells in (C) were assessed for cell lysis by fluorescence microscopy. (E) FACS analysis for surface expression of CD107a was performed after mock- or TCR-electroporated human CD8+ T cells were co-cultured with Ad-hcdr2 or Ad-GFP-transduced AAA (A2.1) KECs as indicated. (F) Recognition of cdr2-expressing gynecologic tumor cells by cdr2 TCR-electroporated CD8+ T cells. human CD8+ T cells were electroporated with in vitro transcribed cdr2 TCR α- and β-chain RNA (black bar) or GFP RNA (blue bar) and co-cultured ($10^5$) with the indicated tumor cells ($5 \times 10^4$) in an 18 h IFN-γ ELISPOT assay. Values, representing SPC per million CD8+ T cells, are the average of duplicate wells; error bars indicate standard deviation.

Ability of the α- and β-chains encoded by clone 11/12 to form functional TCR αβ heterodimers was tested by co-electroporation of in vitro transcribed α- and β-chain mRNA into CD8+ normal human donor peripheral blood lymphocytes (PBL). Over 32% of CD8+ PBL formed cell surface heterodimers capable of binding HLA-A2.1/cdr2(290-298) tetramers (FIG. 6A). T cells electroporated in parallel with a single mRNA encoding GFP did not exhibit tetramer staining, but demonstrated that electroporation was highly efficient (~98% cells were GFP positive; FIG. 6A). Negative control tetramer did not stain either α- and β-chain TCR or GFP mRNA-electroporated T cells (FIG. 6A).

Figure 6B:
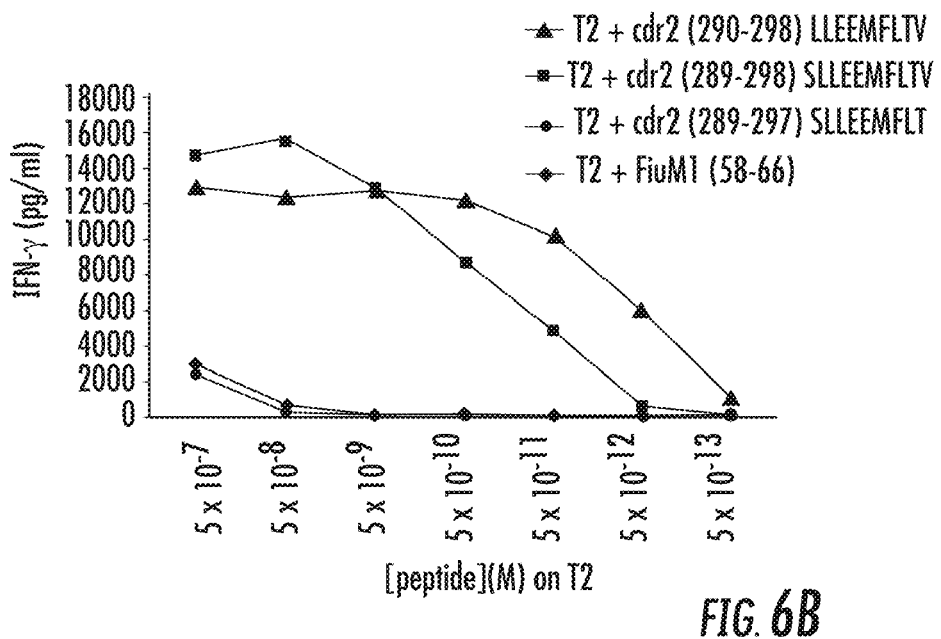

Functionality of cdr2-specific TCR mRNA-electroporated CD8+ PBL was determined by measuring IFN-γ release following co-culturing with T2 cells pulsed with different concentrations of specific [cdr2(290-298) and cdr2(289-298)] or control [FluM1 and cdr2(289-297)] peptides. IFN-γ release was elicited by T2 cells pulsed with the specific cdr2 epitopes, but not the control peptides or no peptide (FIG. 6B). The cdr2-specific TCR electroporated CD8+ PBL populations released IFN-γ 20-fold above background at cdr2(290-298) concentrations as low as 0.5 pM, with half maximal IFN-γ secretion occurring at peptide concentrations of 35 pM, representing a >3 orders of magnitude improvement in avidity from the original AAD 290 CTL line (6.8 nM, measured by ELISPOT). Ability of the cdr2 α- and β-chain to confer specific recognition for both cdr2(290-298) and cdr2(289-298) (FIG. 3B) shows that recognition of both of these epitopes by the parental AAD 290 CTL line is due to cross-reactivity by a single TCR.

Figure 6C:
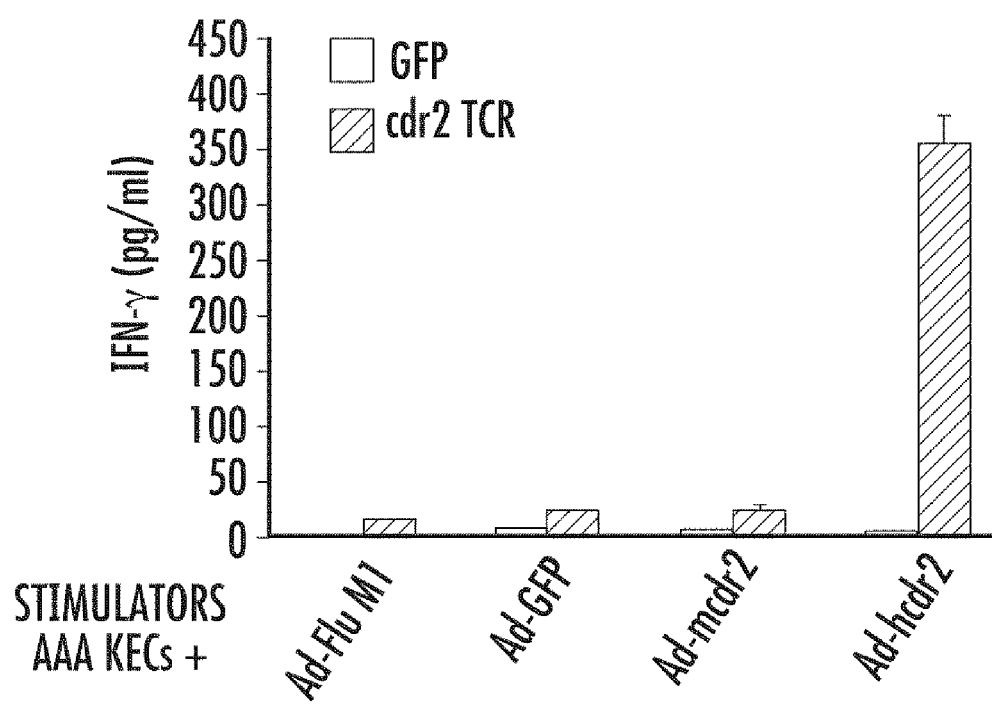

To determine whether human T cells expressing the cloned cdr2 TCR could recognize cells expressing endogenous cdr2, cdr2-specific TCR mRNA-electroporated CD8$^+$ PBL were co-cultured with KEC derived from AAA A2.1 transgenic mice (with a human α3 domain) transduced with Ad-hcdr2 or with control vectors (Ad-FluM1, Ad-GFP, or Ad-mcdr2). IFN-γ release was detected in the co-cultures with Ad-hcdr2 but not mock-transduced cells or GFP-transfected T cells (FIG. 6C).

Figure 6E:
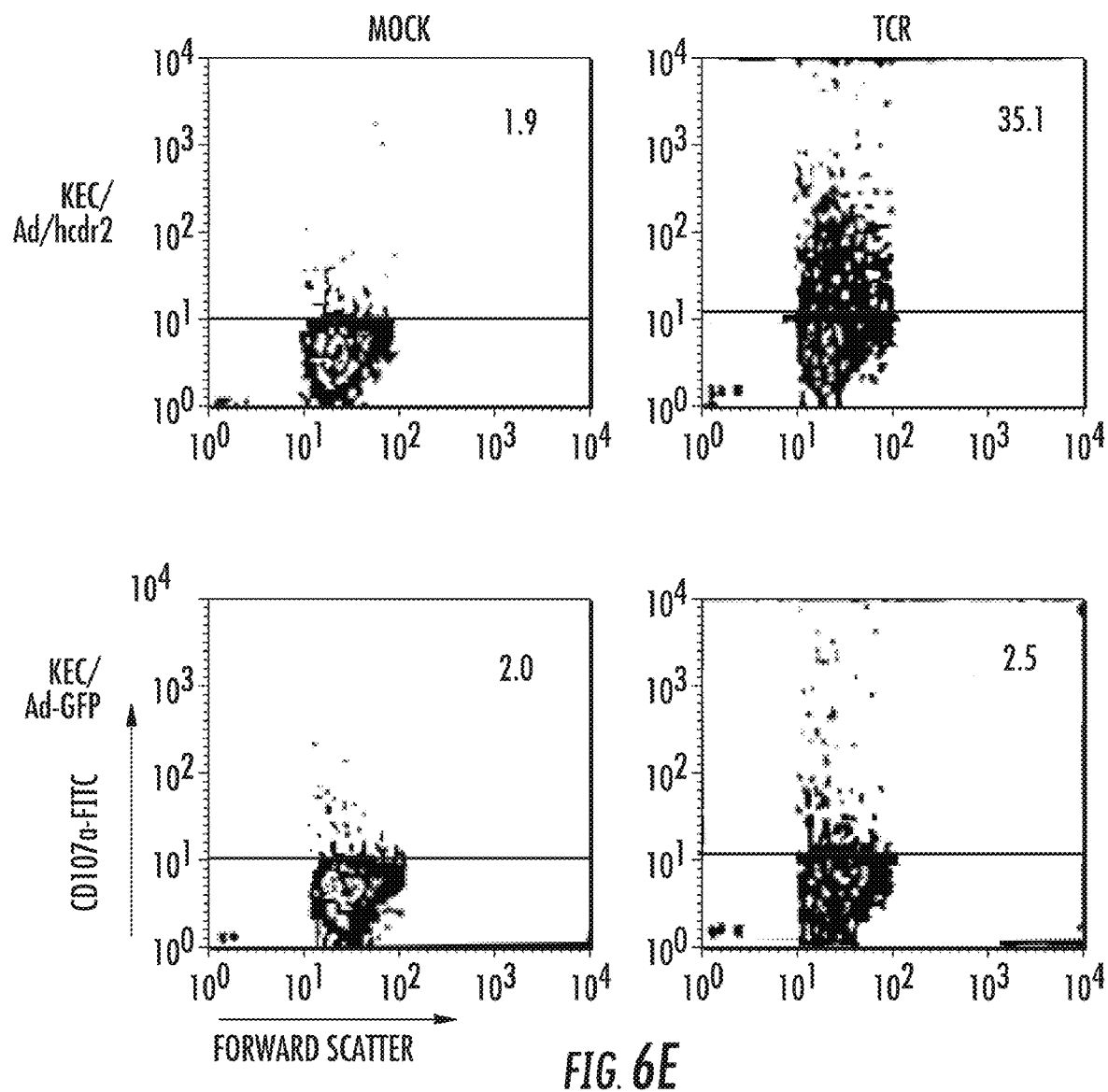

Functional lytic activity of the TCR mRNA-electroporated T cells was determined by 2 methods: by determining cell killing by fluorescence microscopy and by FACS analysis of surface CD107a (LAMP1) mobilization in CD8$^+$ T cells, a means of enumerating the number of activated lytic CD8$^+$ T cells. Fluorescence microscopy of co-cultures of cdr2-specific TCR mRNA-electroporated CD8$^+$ PBL and targets revealed that cdr2 TCR-PBL, but not control GFP-PBL, killed Ad-hcdr2 KECs but not control transduced KECs (FIG. 6D). Mobilization of CD107a was evaluated by co-culturing TCR- or mock electroporated human CD8$^+$ T cells with either Ad-hcdr2 or Ad-GFP transduced KECs. 35% of cdr2 TCR-PBL co-cultured with Ad-hcdr2-transduced KECs became positive for surface CD107a expression (FIG. 6E). In contrast, ~2% of cdr2 TCR-PBL co-cultured with KEC-GFP, or mock-electroporated CD8$^+$ T cells mobilized CD107a (FIG. 6E). The percentage of cdr2 TCR-PBL detected by tetramer analysis (32%; FIG. 6A) correlated well with the percentage that mobilized CD107a after detection of cdr2-expressing target cells (FIG. 6E), showing that the majority of cdr2-TCR-transfected T cells were functional.

Figure 6F:
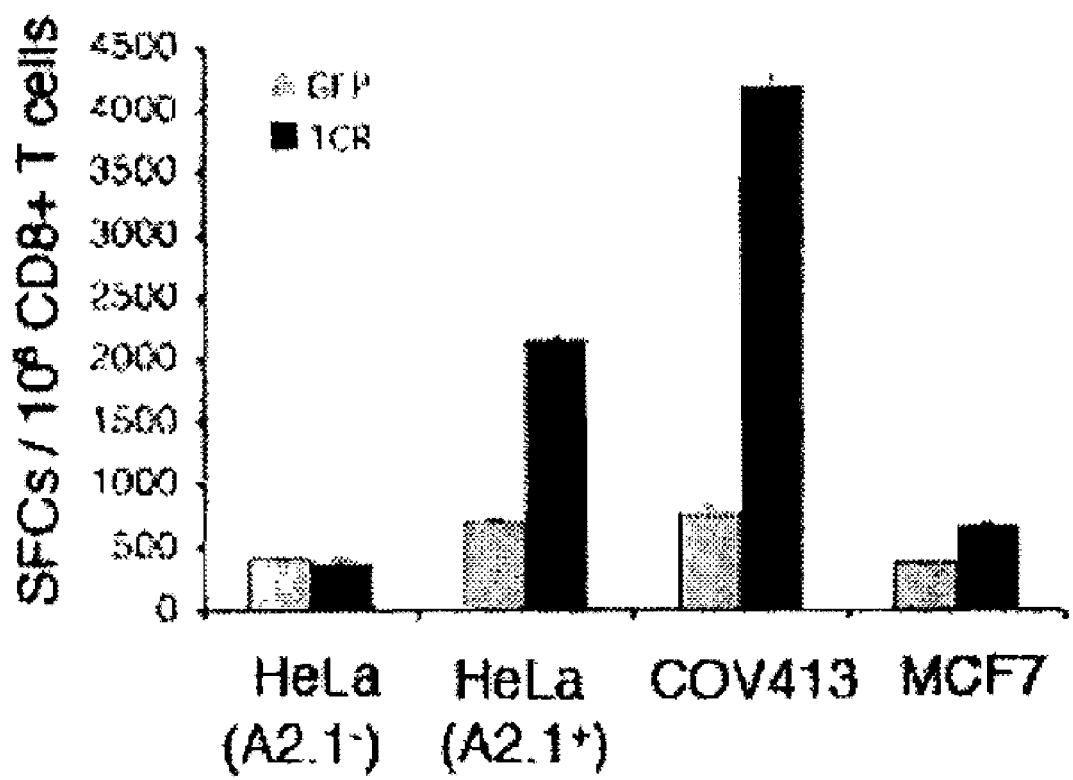

Example 6 cdr2 TCR-Expressing Human CD8$^+$ T Cells Recognize cdr2-Expressing Gynecologic Tumor Cells The next experiment evaluated whether cdr2(290-298)-specific TCR mRNA-electroporated CD8$^+$ PBL ("cdr2 TCR-PBL") can recognize physiologic levels of endogenous cdr2 antigen in human tumor cell lines, including cervical (HeLa), breast (MCF7) or ovarian (COV413) tumors. cdr2 TCR-PBL, but not control GFP-transfected PBL, were able to recognize A2.1-HeLa cells by IFN-γ ELISPOT after they had been stably transfected with A2.1 (HeLa.A2.1$^+$; FIG. 6F). In addition, a significant number of cdr2 TCR-PBL responded to the A2.1$^+$ breast cancer cell line MCF7, which expresses relatively low levels of A2.1 (FIG. 6F). Moreover, human cdr2 TCR-PBL, but not GFP-PBL controls, were capable of robust recognition of A2.1$^+$ COV413 ovarian tumor cells by IFN-γ ELISPOT (FIG. 6F).

Thus, the cdr2-specific TCR confers normal CD8$^+$ T cells with ability to mature into functional CTL able to recognize cdr2-expressing tumor cells. Accordingly, cdr2(290-298) peptide is efficacious for targeting cdr2-expressing human tumors.

HuD Materials and Experimental Methods

HuD Patient #1: A 59 year old male smoker was first seen at RUH in November 2006, 5 months after the onset of short-term memory loss, numbness and tingling in the fingertips of both hands, and worsening gait. Workup revealed an asymptomatic lung nodule, which was biopsied and found to be small cell lung cancer. When examined at RUH, the patient exhibited profound short-term memory loss, with no recall of events occurring 5 minutes prior, and pronounced emotional lability. Lumbar puncture revealed a CSF pleiocytosis of 6 WBCs/mm$^3$. One week later, the patient went into cardiac arrest on his way to RUH for treatment and expired. At time of patient's death, he was in the midst of completing chemotherapy (cisplatin and etoposide) for his cancer, and had completed radiation therapy the week prior.

HuD Patient #2: A 74 year old woman smoker was well until 2005 at which time she presented with progressive numbness in the feet and hands, as well as fatigue and weight loss. Work-up revealed the anti-Hu antibody in October 2005, and SCLC in June 2006, for which she underwent chemotherapy and radiation therapy. On examination at that time the patient had a moderate pansensory neuropathy, with dysesthesia in the distal hands and feet, and moderate gait imbalance requiring a cane. In subsequent follow-up visits, her cancer has remained in remission; however, her neurologic symptoms have progressively worsened to the point that she requires a walker to ambulate and has chronic painful neuropathy.

HuD Patient #3: A 65 year old woman developed numbness in her feet in spring of 2001. In April 2002 workup revealed small cell lung cancer for which she received chemotherapy and prophylactic brain irradiation. In March 2003 she developed difficulty walking and coordination problems, becoming wheelchair-bound over the ensuing months. She was diagnosed with anti-Hu antibody in July of that year. The patient was admitted to RUH April of 2004 when she had worsening dysarthria and increased tremors of left hand and shoulder. She exhibited a CSF pleiocytosis of 13 WBCs/mm$^3$ at that time. To date, patient remains relatively stable with her symptoms and her cancer remains in remission.

Cell Lines and Antibodies.

Antibodies for FACS staining were obtained from Becton-Dickinson (San Jose, Calif.), except CD8-FITC (Beckman Coulter). The EL4 cell line expressing HLA0201 was obtained from Alan Houghton. T2 cells were obtained from ATCC.

Peptides

The peptide library for iTopia screening was purchased from Jerini Peptide Technologies (Berlin, Germany). Peptides for mouse experiments and influenza matrix peptide GILGFVFTL were from American Peptide Company (Sunnyvale, Calif.). The CEF peptide mixture was purchased from MabTech (Mariemont, Ohio). Influenza nucleoprotein peptides for A0101 and A0301 were from Anaspec (San Jose, Calif.).

iTopia Screening

Peptides were dissolved in DMSO 10 mM and stored in aliquots at −20 C. All screening assays were performed according to the manufacturer's instructions using the provided reagents (Beckman Coulter Immunomics, San Jose, Calif.). For the initial binding assay each 0.1 mM peptide was added to plates with wells coated with recombinant HLA molecules, β2m and FITC-labeled anti-HLA class I. Incubation was performed for 18 hr at 21 C and plates were then washed and read in a fluorescence plate reader (Ex 490 nm, Em 520 nm) (Molecular Devices, Sunnyvale, Calif.). For affinity measurements, eight serial dilutions of the peptides were made and assayed as in the binding assay. For off-rate measurements, peptides were added as in the binding assay, incubated for 18 hr at 21 C, washed and then shifted to 37 C for the indicated time points. Data were analyzed with the iTopia software using Prism (GraphPad, San Diego, Calif.) and iScores were generated using a proprietary formula which takes into account all three parameters measured.

Mice and Immunizations

Wild type C57BL/6 mice were purchased from Jackson Labs (Bar Harbor, Me.). AAD mice are transgenic for the human HLA-A0201 molecule with a mouse α3 domain(25) on a C57BL/6 background and were purchased from Jackson Labs. HHD mice are transgenic for the human HLA-A0201 molecule with a mouse α3 domain on a $\beta 2m^{-/-}$ background and were obtained from F. Lemmonier. Transgenic mice were monitored for expression of HLA-A0201 on peripheral blood cells by flow cytometry using the BB7.2 antibody (BD Pharmingen). Mice were immunized intradermally with 100 ul purified virus. 400 ug of pertussis toxin (Sigma) was administered intraperitoneally on day 0 and day 2. Mice were used for experiments 13 days after adenovirus immunization. All mice were housed in an SPF facility and were used according to IUCAC regulations under an approved Rockefeller University animal protocol.

Adenovirus Production

Control adenovirus expressing GFP and adenovirus expressing GFP and the HuD protein were made by H. J. Okano using the pAdenoTrack vector and recombination in bacteria according as previously described. Adenovirus was produced for experiments by transduction of HEK293 cells (ATCC, Manassas, Va.) and virus in the supernatant was purified after 72 hours using the Adenopure kit (Puresyn) according to kit instructions. Viral titers were determined by serial dilution in 293 cell cultures and counting GFP positive cells after 24 hours. Virus was used at 1:10,000 titer.

Mouse Kidney Cell Culture

Primary kidney cell cultures were made by mashing kidneys with the back of a syringe, pipetting until a single cell suspension was obtained, and passing the suspension over a 70 um cell strainer. After washing, cells were cultured in D10 medium (DMEM supplemented with gentamicin, L-glutamine (Cellgro, Mediatech) and 10% fetal bovine serum (HyClone). Cells were fed by replacing medium on days 4 and 7. On day 7 10 U/ml recombinant mouse IFN-γ (R and D Systems) were added to the cells. On day 8, 10 ul of purified adenovirus was added to each plate. Cells were harvested the next day for use in the elispot assay.

Peripheral Blood Isolation

Blood cells were collected by leukapheresis under a Rockefeller University IRB-approved protocol with informed consent. PBMC were isolated by density gradient centrifugation over Ficoll-Hypaque (Pharmacia), and separated into T cell enriched (ER+) and T cell depleted (ER−) fractions by rosetting with neuraminidase-(Calbiochem, La Jolla, Calif.) treated sheep red blood cells (Colorado Serum Company, Denver, Colo.). These cell fractions were cryopreserved by freezing in 10% human serum albumin/10% DMSO/RPMI.

Dendritic Cell Culture

Human dendritic cells (DC) were generated from peripheral blood mononuclear cells (PBMC). Briefly, ER− cells were cultured in the presence of 100 U/ml IL-4 (R&D Systems) and 100 U/ml GM-CSF (Immunex) for 6 days to generate immature DC. DC were harvested on day 6 and plated with PGE2 and TNFa to induce maturation. After 2 days mature DC (mDC) were harvested and used for T cell stimulation.

CD8+ T Cell Isolation

ER+ PBMC fractions were thawed incubated with anti-CD8 MACS beads according to manufacturer's instructions (Miltenyi Biotech, Auburn, Calif.) For experiments with adenovirus-immunized mice, spleens were harvested on day 13 and CD8+ T cells were purified as in the human protocol using anti-mouse CD8a beads (Miltenyi).

In Vitro Stimulation of Human Peripheral Blood T Cells

Purified CD8+ T cells were incubated with autologous mDC at a 30:1 ratio in 24 well plates with 10 ug/ml peptide in AIM-V medium (Invitrogen) supplemented with 5% FBS. After one day of culture recombinant human IL-2 (Chiron, Calif.) was added at 10 IU/ml.

In Vitro Stimulation of Mouse Spleen Cells

Spleen cells from adenovirus-immunized mice were used for re-stimulation with indicated peptides. Cells were stimulated at $2\times10^6$/well of a 24 well plate with 0.5 uM peptide and 10 IU/ml recombinant human IL-2 (Chiron, Calif.) in RPMI with 10% FBS. After 10 days of culture, cells were harvested and CD8+ T cells were isolated by magnetic separation (Miltenyi). Subsequent stimulations were performed similarly with syngeneic irradiated, peptide pulsed splenocytes.

Tetramer Staining

All HLA-A0201 tetramers were obtained from Beckman Coulter Immunomics. $1.0\times10^6$ patient PBMC or $0.3\times10^6$ cultured CD8+ cells were incubated with a 1:20 dilution of tetramer for 20 minutes at room temperature. Antibody to CD8 was then added to the cells for an additional 10 minutes, washed and analyzed immediately using a BD FacsCaliber. Dead cells were excluded by gating on Topro-3 (Molecular Probes, Eugene, Oreg.) negative cells and on the CD8+ population.

Tetramer+ T Cell Sorting

CD8+ T cells were purified by positive selection (Miltenyi) from the frozen T cell fractions of patient leukapheresates. After 8-12 days of culture with mDC, the cells were harvested and incubated at $20\times10^6$/ml with a 1:20 dilution of tetramer. The tetramer-positive population was sorted on a FACS Aria instrument (BD BioSciences). After sorting, cells were placed into culture in 96-well plates with 10:1 autologous, peptide-pulsed PBMC and 50 U/ml IL-2. After a recovery period of 8 days in culture, T cells were used in assays as described.

Elispot

Nitrocellulose plates (Millipore Bedford, Mass.) coated overnight with 5 ug/ml anti-IFNγ or IL-13 antibody (MabTech, Sweden) were blocked for 2 hours with 10% FBS at 37 C. CD8+ T cells were plated with 25,000 peptide-pulsed target cells and incubated for 20 hrs at 37 C. Cytokine producing cells were detected using biotinylated secondary antibodies (MabTech) and spots developed by incubation with streptavidin-horseradish peroxidase (Vector Labs, Burlingame, Calif.) and AEC substrate (Sigma, St. Louis, Mo.). All conditions were performed in duplicate or triplicate and spots were enumerated by an outside consultant (Zellnet Consulting).

Multiplex Analysis of Cytokines

Supernatants were taken from sorted or unsorted T cells cultured with T2 cells pulsed with HIV (negative control), influenza M1 or Hu157 peptide for 24 hours. Samples were analyzed neat and diluted 1:10 using a Biosource human cytokine multiplex kit according to the manufacturer's instructions and Perkin-Elmer Luminex bead array reader.

Intracellular FACS Staining

Tetramer-sorted T cells were incubated at a 1:1 ratio with HIV (negative control), influenza M1 or Hu157 peptide-pulsed T2 stimulator cells in 96-well plates for either 6 hours (CD107a and cytokines) or 18 hours (IL-13 only staining) with CD107a antibody, 10 ug/ml brefeldin A and 6 ug/ml monensin in R10 medium. Cells were washed 3× with PBS and stained in FACS buffer with CD8 antibody for 20 min at 4 C, washed, followed by 30 min at 4 C with Fix/Perm (BD Pharmingen). After washing, cells were stained in Perm/Wash buffer with IFNγ, IL-13, and IL-4 antibodies for 30 min at 4 C, followed by washing and acquisition on a BD FACS-Caliber.

Microarray Analysis

Tetramer-sorted T cells specific for each antigen were incubated with mDC pulsed with relevant peptide, irrelevant peptide or in anti-CD28 and tetramer coated wells for 18 hours. Samples of culture supernatants were taken and the cells were lysed with buffer RLT (RNAeasy kit, Qiagen) containing RNAsin (Promega). Probes for genechips were synthesized by double amplification (Ambion) and hybridized onto Affymetrix HG133 Plus 2.0 chips. Data was normalized using Genespring software (Agilent) GC-RMA normalization, followed by filtering signal>100. Fold-change of relevant peptide response compared to irrelevant peptide response was determined for each T cell group.

Example 1

Screening for Candidate HuD Peptide Epitopes

To identify HuD peptides able to bind HLA class I molecules, we generated a library consisting of all 386 possible nonamer human HuD peptides, including previously described splice variants. (Okano and Darnell, (1997) *J. Neurosci.*; 17:3024-3037). We screened these peptides using an approach successfully applied to identify CD8+ T cell epitopes for survivin, cdr2 and *mycobacterium tuberculosis*. Peptides were screened for the ability to bind recombinant HLA molecules and further analyzed by determining off-rate and affinity, yielding a net score for each peptide. We initially focused our effort on the class I alleles most commonly found in the Western population. HLA-A0201 and HLA-A0301 yielded a total of 48 peptides with significant net scores. To refine this list, we reasoned that pathophysiologically relevant human HuD-specific T cells should fail to react with the HuA protein. HuA is closely related to HuD but is ubiquitously expressed, and should be a strongly tolerizing antigen; moreover, Hu PND patients do not develop systemic autoimmune reactions that might suggest HuA autoreactivity. 18 HuD HLA A0201 and 5 HLA-A0301 binding peptides with different sequences than HuA (Table 9) were identified for further evaluation.

TABLE 9

Microarray analysis of Hu157-specific Type 2 T cells

| Hu157 AND aCD28 NOT Flu | | Hu157 NOT Flu | |
| --- | --- | --- | --- |
| Fold Change | Gene | Fold Change | Gene |
| −46.51 | DPP4 | 45.14 | CXCL10 |
| 34.44 | MGC4677 | 39.07 | LOC200169 |
| 18.49 | MCM10 | 36.74 | GNG4 |
| 18.24 | IL13 | 35.76 | SHF |
| 12.29 | TNFRSF18 | 34.44 | MGC4677 |
| 11.44 | RRAS2 | 27.95 | GNG8 |
| −11.20 | TCF7L2 | 21.20 | KLRK1 |
| 10.71 | CENPH | 18.49 | MCM10 |
| −9.52 | CFH | 18.24 | IL13 |
| 8.99 | TRMT5 | 17.17 | CD80 |
| 8.96 | BCL2L11 | 14.63 | CTTN |
| 8.22 | RNF14 | −14.62 | LOC344405 |
| −8.20 | ALOX5 | −14.43 | TCF12 |
| 8.18 | PMAIP1 | 14.25 | DUSP2 |
| 7.82 | ARPC1A | 14.22 | GNG4 |
| 7.62 | TNFRSF8 | −14.06 | FAM13A1 |
| 7.52 | MPP6 | 13.78 | ASTN2 |
| 7.20 | LAIR2 | 12.96 | MGC42105 |
| | | 12.51 | SGPP2 |
| | | 12.51 | BACH2 |
| | | 12.29 | TNFRSF18 |
| | | 12.21 | GALC |
| | | 11.82 | KFBP4 |
| | | 11.75 | IL5 |

Genes found in supernatant and/or intracellular staining experiments and other genes of immunological interest are in bold text.

Example 2

Identification of Classical HuD-Specific CD8+ T Cells in a Hu Patient

Figure 7:
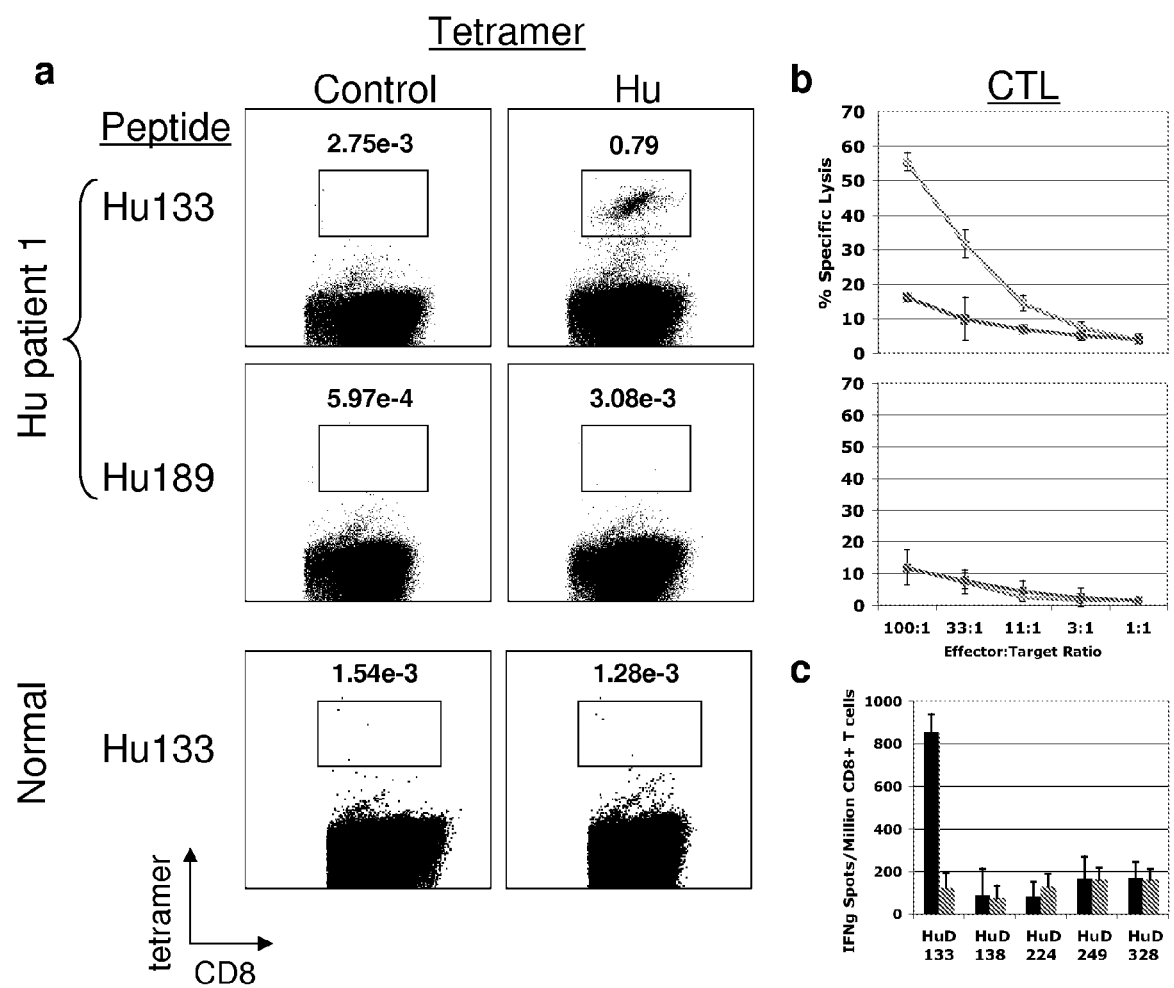
FIG. 7. Demonstration of Hu133-specific T cells that have lytic activity and secrete IFN-γ. (A) Tetramer staining of cells from patient 1 (HLA0301) after one round of in vitro expansion with A0301 predicted peptides. (B) The expanded T cells were also tested for functional activity in a CTL assay. Irrelevant peptide condition is designated by red squares, relevant peptide is blue circles (C) Similar results were obtained with IFN-γ Elispot, gray bars are irrelevant peptide condition and black bars are relevant peptide.
Figure 8:
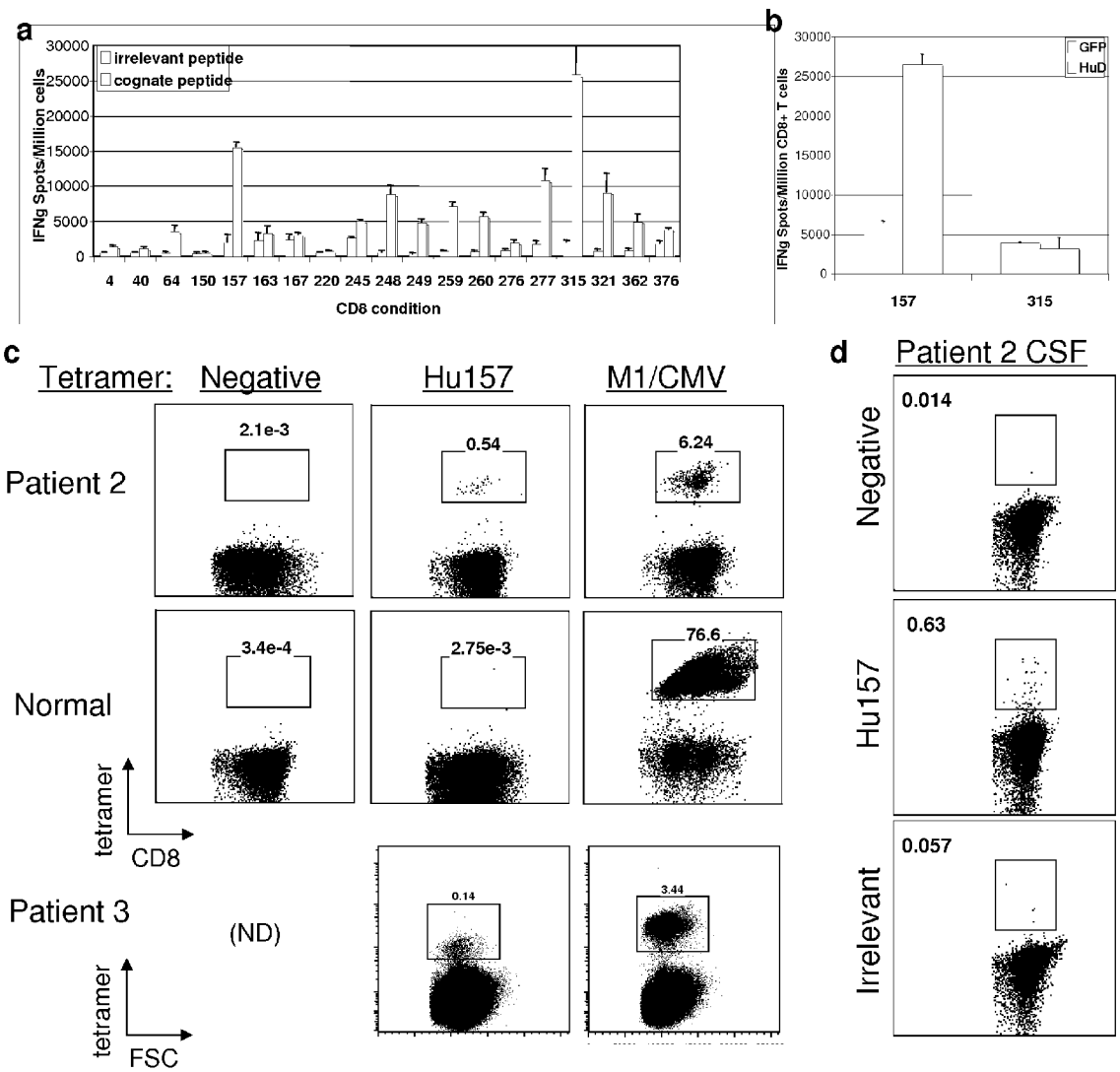
FIG. 8. Identification of Hu157 epitope and Hu157-specific T cells in patients. (A) Screening of Hu peptides in HLA-A0201 transgenic mice. CD8+ T cells purified from AAD mouse spleen cultures were cultured with stimulator cells pulsed with cognate or irrelevant peptide. A positive response was considered at least a two-fold increase in signal over an irrelevant A0201 binding control peptide. (B) CD8+ T cells were tested for their ability to recognize whole HuD protein processed and presented by primary HHD kidney cells. Wild-type kidney cells were not recognized (data not shown). Peptide 315 was positive in the first screen (a), but was not processed on HLA-A0201 in the kidney cell experiment (b), indicating possible in vitro priming of T cells to this epitope or a low affinity T cell response and was not selected for further experiments with patient T cells. (C) Tetramer staining of patient 2, normal donor and patient 3 peripheral blood T cells after one round of in vitro expansion with HuD157 peptide. Positive control expansions and tetramer staining were with either M1 or CMV, depending on the response of the donor to these viruses. (D) Tetramer staining for Hu157 T cells in CSF of Hu patient 2.

Cells from Hu patient 1, an acutely ill HLA-A0301 individual, were used to further screen the HLA-A0301 peptides. CD8+ T cells were cultured for 8 days with autologous peptide-pulsed dendritic cells (DC) to expand antigen specific T cells. CD8+ T cells recognized peptide Hu133 but none of the other candidate peptides, as demonstrated by binding to specific HLA-peptide tetramers (FIG. 7a and Supplementary FIG. 7). We found that these Hu133-specific CD8+ T cells were functional by chromium release cytotoxicity and IFNγ ELISPOT assays (FIGS. 7b and 7c). To determine whether Hu133-specific T cells could be detected in neurologically normal control patients, T cells were tested for tetramer staining after eight days of in vitro expansion. We also tested three chronically ill HLA-A0301 Hu patients, and did not find significant levels of Hu133-specific T cells. We note, however, that two of these three patients were also HLA A0201, and did have A0201-Hu-specific T cells (see FIG. 8), suggesting that their dominant Hu response may be HLA A0201 restricted. Zero of two A0301 control patients had detectable Hu133-specific T cells in this assay, while all patients and controls showed T cell expansion of influenza nucleoprotein (NP) specific T cells.

Example 3

Identification of Atypical HuD-Specific CD8+ T Cells In Hu Patients

Given the large number of candidate HuD HLA A0201 peptides, we screened the 18 high-scoring HuD HLA A0201 peptides for their ability to generate immune responses in vivo using transgenic mice expressing human HLA-A0201. (25)(14) These mice were immunized with replication-defective adenovirus expressing full-length mouse HuD protein (AdV-HuD). CD8+ splenocytes purified from immunized mice and re-stimulated with HuD peptides showed reactivity to 11 of the 18 candidate A0201-restricted HuD peptide pulsed targets by IFN-γ ELISPOT (FIG. 8a).

As a more stringent follow-up screen, we assayed reactivity of CD8+ T cells to more physiologic amounts of HuD peptides. Primary kidney epithelial cells (KECs) from HLA- A0201 transgenic or wild-type control mice were infected with AdV-HuD and used as targets in an IFN-γ ELISPOT. Of the 11 peptides tested in this secondary screen, only HuD157 T cells recognized KECs expressing the full HuD sequence. (FIG. 8b). This result indicates that peptide HuD157 can be naturally processed and presented on HLA-A0201.

We were able to detect Hu157-specific CD8+ T cells in the peripheral blood from 2/2 chronically ill A0201 Hu patients after restimulation (Hu patients 2 and 3; FIG. 8c). In contrast, none of four control patients harbored Hu157-specific CD8+ T cells, (FIG. 8c) demonstrating specificity of the tetramer and indicating that the patient Hu157 cell populations were not due to in vitro priming. Each control patient harbored T cells specific for at least one of two positive control tetramers specific to influenza M1 or CMV (FIG. 8c). We also detected a high percentage (~0.5%) of Hu157 tetramer positive cells directly from cerebrospinal fluid available from Hu patient 2 (FIG. 8d). Taken together, these results demonstrate that Hu patients have T cells capable of recognizing Hu157 as a naturally processed HLA-A0201 epitope.

Example 4

Function of Atypical Hu-Specific CD8+ T Cells

Figure 9:
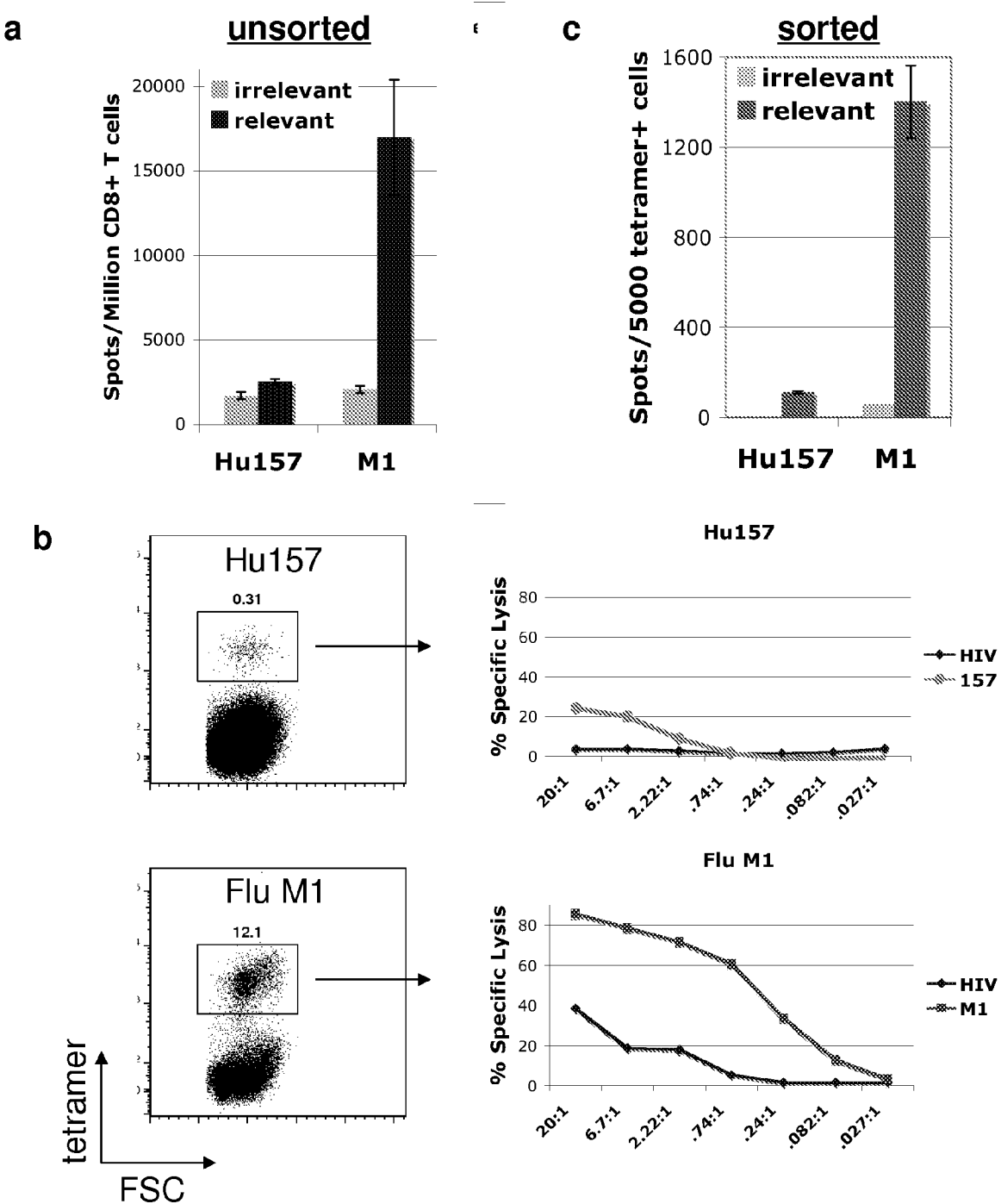
FIG. 9. Weak lytic activity and IFN-γ secretion by Hu157 patient T cells. (A) Hu157 and influenza M1 tetramer+ T cells from an Hu patient were expanded one time in vitro with peptide, followed by FACS sorting of the tetramer+ population. Tetramer+ cells were allowed to recover with irradiated, peptide-pulsed, autologous PBMC and IL-2. After recovery, the function of the T cells was tested in a CTL assay. (a) Elispot with bulk (pre-sort) CD8+ T cell cultures; (B) Tetramer staining showing sorting gate and CTL assay using sorted T cells (C) IFN-γ Elispot assay with sorted T cells.

We initially attempted to assess the function of the Hu157-specific CD8+ T cells in our two HLA-A0201 Hu patients using standard assays. We consistently found extremely low T cell responses to Hu157-pulsed targets in CTL (data not shown) and IFN-γ ELISPOT (FIG. 9a) assays in HuD patient 2, despite significant positive T cell responses to influenza or CMV peptides. To address the possibility that this might have resulted from a low number of Hu157 responding T cells yielding responses at or below our limits of detection, and based on our finding that one round of stimulation with Hu157 peptide led to expansion of Hu-specific T cells in patients but not control individuals by tetramer staining (FIG. 8c), we stimulated cells to obtain sufficient numbers for tetramer FACS sorting. The percentage of Hu157 tetramer-positive cells in the pre-sorted population was at least one log lower than influenza M1 tetramer specific cells, consistent with a low precursor number of Hu157-specific CD8+ T cells present in the unstimulated T cell population (FIG. 9). Sorting cells from both influenza- and Hu157-specific T cell populations allowed us to add equivalent numbers of each cell type to the assays.

CTL assays using sorted Hu157-specific T cells from Hu patient 2 showed a low but detectable amount of specific lysis, when compared with influenza-specific T cells (a maximum of ~20% specific lysis, compared to 85% with influenza, using equivalent numbers of sorted antigen-specific T cells, FIG. 9b). In addition, only relatively small numbers of IFN-γ producing cells were seen in ELISPOT assays using Hu157-specific T cells (100 spots compared with 1400 for influenza; FIG. 9c). Similarly, assays with Hu157 T cells from patient 3 showed 40% killing by CTL assay, compared to 85% with influenza T cells, and 40 vs. 540 IFNγ-secreting cells by ELISPOT assay. Taken together, these experiments demonstrate that Hu157-specific CD8+ T cells are indeed present in our HLA-A0201 patients, but are detectable in traditional assays for CD8+CTL function only if normalized for low precursor numbers. The low signals in both assays even with sorted Hu157 T cells suggests that this population is either relatively unresponsive or harbors cells with functions other than the typical CD8+ IFN-γ secretion and robust lytic activities, for which different assays are needed.

Accordingly, we searched for differences between Hu157-specific T cells and influenza-specific T cells. The two CD8+ populations were nearly identical with respect to eight standard cell-surface markers. Since cytokine production profiles have been used to discriminate T cell subtypes, we measured 25 cytokines in the supernatants of cultures of CD8+ T cells incubated with cognate peptide-pulsed target cells. Multiplex analysis of culture supernatants of Hu-specific CD8+ T cells from Hu patient 1 revealed a classic CTL profile with the secretion of IFN-γ in response to HuD peptide and influenza peptide (FIG. 10a). In stark contrast, the atypical Hu-specific T cells from Hu patients 2 and 3 exhibited robust production of IL-13 (5130 pg/ml and 389 pg/ml) and IL-5 (3857 pg/ml and 162 pg/ml) in response to Hu157 peptide, but no detectable IFN-γ production (FIGS. 10b and c). Similar IL-13 production in response to Hu peptide was obtained with unsorted bulk T cell cultures, indicating that tetramer binding and sorting itself did not result in the unusual T cell phenotype. We also found that Hu patient 2 harbored typical T cells specific for influenza, as the CD8+ T cells produced IFN-γ in response to influenza-specific peptide (2471 pg/ml; FIG. 10c).

We extended these observations by developing an Elispot assay to enumerate T cells producing IL-13 in response to antigen. We co-cultured stimulated CD8+ T cells from Hu patient 2 and Hu157 tetramer sorted T cells from Hu patient 3 with peptide-pulsed T2 cells for 20 hours, and counted IL-13 producing cells. Cells from Hu patient 2 showed robust antigen-specific production of IL-13, and in contrast demonstrated weak production of IFN-γ (FIG. 11a; 1937 IL-13 spots/million T cells compared to FIG. 8a; 833 IFN-γ spots/million T cells; total number of possible spots is 3100 based on 0.31% tetramer+ cells in FIG. 8b). Similarly, cells from Hu patient 3 showed an IL-13 response to antigen (159 spots/5000 sorted cells, FIG. 11b).

We next confirmed that IL-13 was produced from Hu-specific T cells in a cell autonomous manner by analysis of Hu157 tetramer positive T cells using intracellular FACS analysis for IL-13. Over 40% of the Hu157-specific T cells from patient 2 were producing IL-13 when assayed at a single 18 hour time point (FIG. 11c, top panels). These results demonstrate that IL-13 is specifically being produced by an atypical HuD-specific CD8+ T cell.

Example 5

Characterization of Hu157-Specific Type 2 (TC2) CD8+ T Cells

We characterized the responses of sorted CD8+ T cells to antigen stimulation by measuring production of Type 1 and Type 2 cytokines using intracellular FACS. Approximately 30% of the Hu157 specific T cells produced IL-4 specifically in response to antigen (FIG. 11c). A small subset (~10%) of either the IL-13 or IL-4 producing cells made IFN-γ in response to antigen (FIG. 11c). In contrast, influenza M1-specific T cells stimulated in parallel from the same patient produced almost exclusively IFN-γ and very little IL-4 (FIG. 11c). Taken together, our results indicate that Hu157-specific T cells are skewed toward the production of Th2 cytokines, including IL-13, IL-5 and IL-4, and henceforth consider them to be Type 2 CD8+ T cells.

Figure 11:
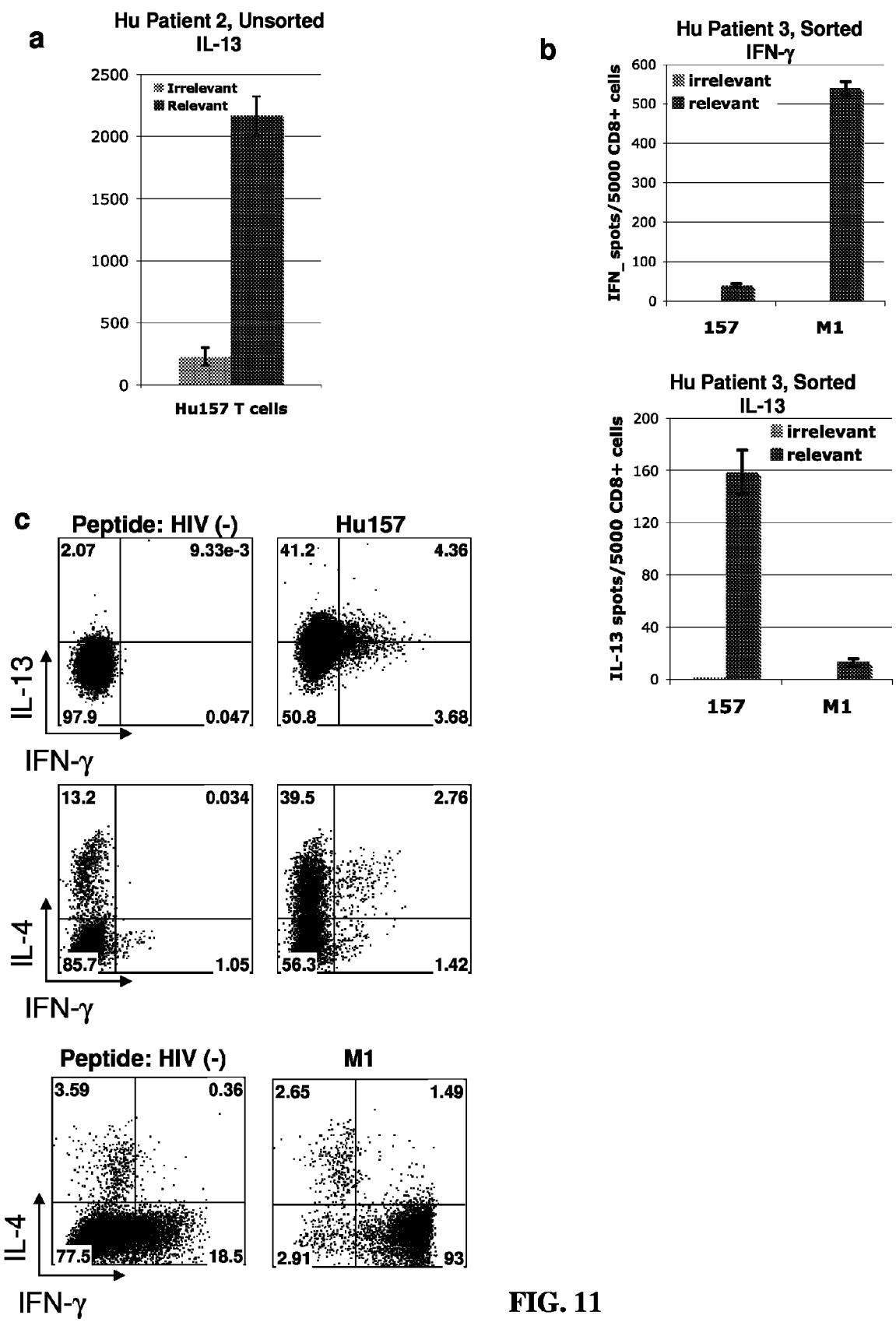
FIG. 11. Hu patient T cells are skewed toward production of IL-13 and IL-4, but not IFN-γ. (A) Elispot assay demonstrating the number of IL-13 producing, Hu-specific CD8+ cells in a bulk, unsorted Hu157 culture from patient 2 (same cells as in FIG. 3a). (B) Elispot results using sorted cells from patient 3, comparing IFN- and IL-13 responses. (C) Intracellular staining for IFN-γ, IL-13 and IL-4 using sorted T cells from Hu patient 2. The top two rows are Hu157 cells after irrelevant and Hu157 peptide stimulation. The bottom row shows staining of influenza M1 specific cells after irrelevant and M1 peptide stimulation (D) Staining for Hu157 and influenza M1-specific CD8+ T cells with lytic activity using CD107a antibody combined with intracellular cytokine staining.
Figure 11D:
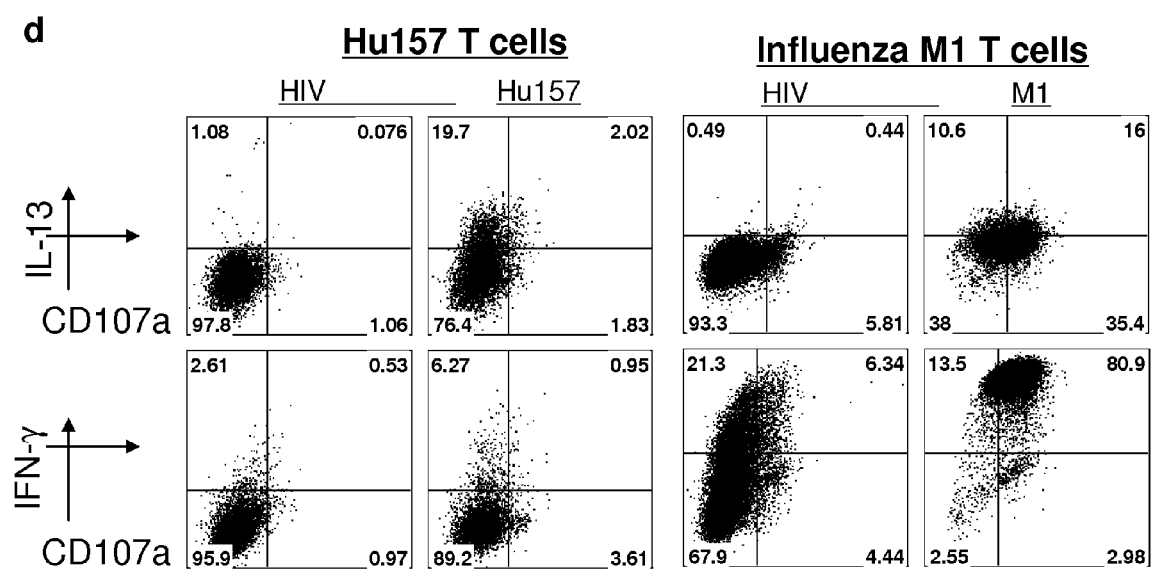

Given the modest lytic activity seen in FIG. 9, we asked whether the poor ability of IL-13 positive T cells to kill is a function of weak activity of the entire population or if it derives from a smaller subpopulation of cells. We assayed sorted Hu157 T cells by staining them for intracellular cytokines along with the lysosomal marker CD107a, a marker of lytic effectors. (27) Only a small number of cells were CD107a positive (~4%; FIG. 11d, left panels). Ten percent of the IL-13+ and twelve percent of the IFN γ+ population stained for CD107a. In contrast, influenza M1-specific T cells from the same patient produced almost exclusively IFN-γ (93% positive), with very little IL-4 and IL-13, and ~75% displayed lytic function (FIG. 11d, right panels). These results indicate that a small population of Hu157-specific T cells, perhaps IL-13+/IFN γ double positive cells, can act as lytic effectors.

Figure 10:
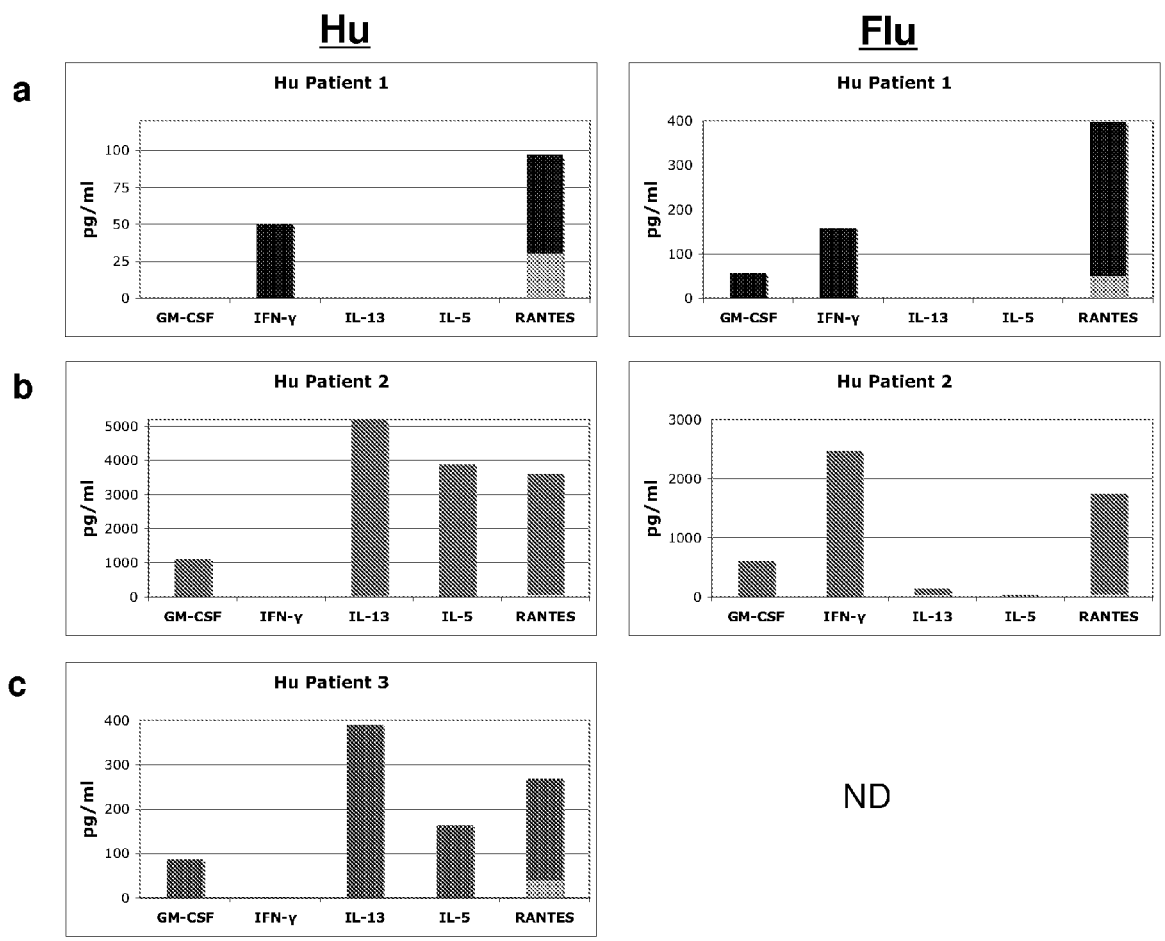
FIG. 10. Screening for cytokines secreted by Hu-specific T cells reveals a Th2-like phenotype in some patients. Supernatants from tetramer-sorted T cells cultured with target cells pulsed with irrelevant or relevant peptide were analyzed for the presence of 25 cytokines using a multiplex kit. All specific cytokine production present above the detection limit (10 pg/ml) is shown. (a) Supernatants from patient #1 (b) from patient #2 (c) from patient #3. Background cytokine signal (irrelevant peptide) is represented by the light shade in the columns.

We further characterized the Hu157-specific T cell phenotype by contrasting their gene expression profile with that of influenza-specific T cells. Expanded T cells were sorted with Hu157 or M1-specific tetramers, activated for 18 hours, and RNA expression profiled by Affymetrix microarray. Given limited clinical material available, we were restricted to analysis of a single patient, but were able to repeat experiments using different means of stimulation (autologous dendritic cells (DCs) pulsed with peptide or with anti-CD28 antibody). We found that the genes for IL-13 and IL-5 were expressed in Hu157 T cells, and those for IFN-γ and granzyme B were up-regulated in influenza-specific T cells in response to specific peptide (Table 9). These data suggest that the genechip provided an accurate reflection of the different proteins present in each T cell type (FIGS. 10 and 11). We also searched for robust changes in gene expression (≧5 fold) that were present in both peptide-stimulated and CD28 antibody-stimulated Hu157 T cells but not in influenza-specific T cells (Table 9). Taken together, the data provide evidence that activated Hu157-specific Type 2 T cells may specifically induce gene expression of IL-13 (18-fold), IL-5 (12-fold) and other immune genes such as CD25, CXCL10, CD30, and GITR; Table 9. These data illustrate that there may be a unique gene profile of Hu157-specific T cells, and support their classification as Type 2 CD8+ T cells.

What is claimed is:

1. An isolated peptide consisting of the amino acid sequence of SEQ ID NO: 146.

2. A composition comprising the isolated peptide of claim 1.

3. The composition of claim 2, further comprising a peptide consisting of the amino acid sequence of SEQ ID NO: 147.

* * * * *

```
                        SEQUENCE LISTING

<160> NUMBER OF SEQ ID NOS: 147

<210> SEQ ID NO 1
    <211> LENGTH: 9
    <212> TYPE: PRT
    <213> ORGANISM: Homo sapiens

<400> SEQUENCE: 1

Leu Leu Glu Glu Met Phe Leu Thr Val
    1               5

<210> SEQ ID NO 2
    <211> LENGTH: 9
    <212> TYPE: PRT
    <213> ORGANISM: Homo sapiens

<400> SEQUENCE: 2

Thr Met Leu Gln Ala Gln Leu Ser Leu
    1               5

<210> SEQ ID NO 3
    <211> LENGTH: 9
    <212> TYPE: PRT
    <213> ORGANISM: Homo sapiens

<400> SEQUENCE: 3

Ser Leu Leu Glu Glu Met Phe Leu Thr
    1               5

<210> SEQ ID NO 4
    <211> LENGTH: 9
    <212> TYPE: PRT
    <213> ORGANISM: Homo sapiens

<400> SEQUENCE: 4

Arg Gly Ile Ser Leu Leu His Glu Val
    1               5

<210> SEQ ID NO 5
    <211> LENGTH: 9
    <212> TYPE: PRT
    <213> ORGANISM: Homo sapiens

<400> SEQUENCE: 5

Tyr Leu Thr Lys Gln Val Glu Leu Leu
```

```
<210> SEQ ID NO 6
<211> LENGTH: 9
<212> TYPE: PRT
<213> ORGANISM: Homo sapiens

<400> SEQUENCE: 6

Met Leu Gln Ser Glu His Pro Phe Val
1               5

<210> SEQ ID NO 7
<211> LENGTH: 9
<212> TYPE: PRT
<213> ORGANISM: Homo sapiens

<400> SEQUENCE: 7

Ala Leu Phe Lys Glu Ile Phe Ser Cys
1               5

<210> SEQ ID NO 8
<211> LENGTH: 9
<212> TYPE: PRT
<213> ORGANISM: Homo sapiens

<400> SEQUENCE: 8

Val Thr Met Glu Glu Glu Tyr Gly Leu
1               5

<210> SEQ ID NO 9
<211> LENGTH: 9
<212> TYPE: PRT
<213> ORGANISM: Homo sapiens

<400> SEQUENCE: 9

Ser Leu Thr Glu Thr Ile Glu Cys Leu
1               5

<210> SEQ ID NO 10
<211> LENGTH: 9
<212> TYPE: PRT
<213> ORGANISM: Homo sapiens

<400> SEQUENCE: 10

Lys Ile Leu Ser Leu Thr Glu Thr Ile
1               5

<210> SEQ ID NO 11
<211> LENGTH: 9
<212> TYPE: PRT
<213> ORGANISM: Homo sapiens

<400> SEQUENCE: 11

Lys Leu Val Pro Asp Ser Leu Tyr Val
1               5

<210> SEQ ID NO 12
<211> LENGTH: 9
<212> TYPE: PRT
<213> ORGANISM: Homo sapiens

<400> SEQUENCE: 12

Ala Ala Ala Lys Asp Leu Thr Gly Val
1               5
```

```
<210> SEQ ID NO 13
<211> LENGTH: 8
<212> TYPE: PRT
<213> ORGANISM: Homo sapiens

<400> SEQUENCE: 13

Arg Ala Leu Glu Leu Glu Ala Val
1               5

<210> SEQ ID NO 14
<211> LENGTH: 9
<212> TYPE: PRT
<213> ORGANISM: Homo sapiens

<400> SEQUENCE: 14

His Leu Gln Ser Gln Val Glu Glu Leu
1               5

<210> SEQ ID NO 15
<211> LENGTH: 9
<212> TYPE: PRT
<213> ORGANISM: Homo sapiens

<400> SEQUENCE: 15

Arg Gln His Phe Val Tyr Asp His Val
1               5

<210> SEQ ID NO 16
<211> LENGTH: 9
<212> TYPE: PRT
<213> ORGANISM: Homo sapiens

<400> SEQUENCE: 16

Gly Val Asn Ala Gln Ser Glu Pro Val
1               5

<210> SEQ ID NO 17
<211> LENGTH: 9
<212> TYPE: PRT
<213> ORGANISM: Homo sapiens

<400> SEQUENCE: 17

Asp Ser Leu Ser His Lys Ala Val Gln
1               5

<210> SEQ ID NO 18
<211> LENGTH: 9
<212> TYPE: PRT
<213> ORGANISM: Homo sapiens

<400> SEQUENCE: 18

Phe Val Tyr Asp His Val Phe Ala Glu
1               5

<210> SEQ ID NO 19
<211> LENGTH: 9
<212> TYPE: PRT
<213> ORGANISM: Homo sapiens

<400> SEQUENCE: 19

Leu Ala Ser Val Asn Pro Glu Pro Val
1               5

<210> SEQ ID NO 20
<211> LENGTH: 9
<212> TYPE: PRT
```

<213> ORGANISM: Homo sapiens

<400> SEQUENCE: 20

Thr Ile Leu Ser Ser Leu Ala Gly Ser
1               5

<210> SEQ ID NO 21
<211> LENGTH: 9
<212> TYPE: PRT
<213> ORGANISM: Homo sapiens

<400> SEQUENCE: 21

Met Leu Gln Ala Gln Leu Ser Leu Glu
1               5

<210> SEQ ID NO 22
<211> LENGTH: 9
<212> TYPE: PRT
<213> ORGANISM: Homo sapiens

<400> SEQUENCE: 22

Leu Leu His Glu Val Asp Thr Gln Tyr
1               5

<210> SEQ ID NO 23
<211> LENGTH: 9
<212> TYPE: PRT
<213> ORGANISM: Homo sapiens

<400> SEQUENCE: 23

His Leu Lys Lys Thr Val Thr Met Leu
1               5

<210> SEQ ID NO 24
<211> LENGTH: 9
<212> TYPE: PRT
<213> ORGANISM: Homo sapiens

<400> SEQUENCE: 24

Leu Tyr Asp Leu Arg Gln His Phe Val
1               5

<210> SEQ ID NO 25
<211> LENGTH: 9
<212> TYPE: PRT
<213> ORGANISM: Homo sapiens

<400> SEQUENCE: 25

Ala Ser Gly Trp Glu Leu Ala Ser Val
1               5

<210> SEQ ID NO 26
<211> LENGTH: 9
<212> TYPE: PRT
<213> ORGANISM: Homo sapiens

<400> SEQUENCE: 26

Glu Cys Leu Gln Thr Asn Ile Asp His
1               5

<210> SEQ ID NO 27
<211> LENGTH: 9
<212> TYPE: PRT
<213> ORGANISM: Homo sapiens

<400> SEQUENCE: 27

```
Cys Leu Gln Thr Asn Ile Asp His Leu
1               5

<210> SEQ ID NO 28
<211> LENGTH: 9
<212> TYPE: PRT
<213> ORGANISM: Homo sapiens

<400> SEQUENCE: 28

Ala Ser Gln Gln Lys Ile Leu Ser Leu
1               5

<210> SEQ ID NO 29
<211> LENGTH: 9
<212> TYPE: PRT
<213> ORGANISM: Homo sapiens

<400> SEQUENCE: 29

Asn Ile Asp His Leu Gln Ser Gln Val
1               5

<210> SEQ ID NO 30
<211> LENGTH: 9
<212> TYPE: PRT
<213> ORGANISM: Homo sapiens

<400> SEQUENCE: 30

Gln Leu Ala Ala Glu Leu Gly Lys Thr
1               5

<210> SEQ ID NO 31
<211> LENGTH: 9
<212> TYPE: PRT
<213> ORGANISM: Homo sapiens

<400> SEQUENCE: 31

Leu Val Pro Asp Ser Leu Tyr Val Pro
1               5

<210> SEQ ID NO 32
<211> LENGTH: 9
<212> TYPE: PRT
<213> ORGANISM: Homo sapiens

<400> SEQUENCE: 32

Lys Val Tyr Glu Gln Leu Asp Val Thr
1               5

<210> SEQ ID NO 33
<211> LENGTH: 9
<212> TYPE: PRT
<213> ORGANISM: Homo sapiens

<400> SEQUENCE: 33

Thr Val Thr Met Leu Gln Ala Gln Leu
1               5

<210> SEQ ID NO 34
<211> LENGTH: 9
<212> TYPE: PRT
<213> ORGANISM: Homo sapiens

<400> SEQUENCE: 34

Leu Gly Ala Thr Gly Ala Tyr Arg Ala
1               5
```

-continued

```
<210> SEQ ID NO 35
<211> LENGTH: 9
<212> TYPE: PRT
<213> ORGANISM: Homo sapiens

<400> SEQUENCE: 35

Ser Leu Ser His Lys Ala Val Gln Thr
1               5

<210> SEQ ID NO 36
<211> LENGTH: 9
<212> TYPE: PRT
<213> ORGANISM: Homo sapiens

<400> SEQUENCE: 36

Leu Val Leu Lys Glu Asn Ser Glu Leu
1               5

<210> SEQ ID NO 37
<211> LENGTH: 9
<212> TYPE: PRT
<213> ORGANISM: Homo sapiens

<400> SEQUENCE: 37

Ala Leu Lys Val Lys Tyr Glu Glu Leu
1               5

<210> SEQ ID NO 38
<211> LENGTH: 9
<212> TYPE: PRT
<213> ORGANISM: Homo sapiens

<400> SEQUENCE: 38

Val Phe Ala Glu Lys Ile Thr Ser Leu
1               5

<210> SEQ ID NO 39
<211> LENGTH: 10
<212> TYPE: PRT
<213> ORGANISM: Homo sapiens

<400> SEQUENCE: 39

Ser Leu Leu Glu Glu Met Phe Leu Thr Val
1               5                   10

<210> SEQ ID NO 40
<211> LENGTH: 10
<212> TYPE: PRT
<213> ORGANISM: Mus musculus

<400> SEQUENCE: 40

Ser Leu Leu Glu Glu Met Phe Leu Ala Ala
1               5                   10

<210> SEQ ID NO 41
<211> LENGTH: 9
<212> TYPE: PRT
<213> ORGANISM: Mus musculus

<400> SEQUENCE: 41

Leu Leu Glu Glu Met Phe Leu Ala Ala
1               5

<210> SEQ ID NO 42
```

```
<211> LENGTH: 51
<212> TYPE: DNA
<213> ORGANISM: Mus musculus

<400> SEQUENCE: 42
tgtgcagcaa gtggggcttc tggaggaagc aatgcaaagc taaccttcgg g            51

<210> SEQ ID NO 43
<211> LENGTH: 459
<212> TYPE: DNA
<213> ORGANISM: Mus musculus

<400> SEQUENCE: 43
atggacaaga ttctgacagc atcatttta ctcctaggcc ttcacctagc tggggtgaat     60
ggccagcaga aggagaaaca tgaccagcag caggtgagac aaagtcccca atctctgaca    120
gtctgggaag gaggaaccac agttctgacc tgcagttatg aggacagcac tttaactac    180 ttcccatggt accaacagtt ccctggggaa ggccctgcac ttctgatatc catactttca    240
gtgtccgata aaaggaaga tggacgattc acaaccttct tcaataaaag ggagaaaaag     300
ctctccttgc acatcataga ctctcagcct ggagactcag ccacctactt ctgtgcagca    360
agtgggcttc tggaggaag caatgcaaag ctaaccttcg ggaaaggcac taaactctct     420
gttaaatcaa acatccagaa cccagaacct gctgtgtac                          459

<210> SEQ ID NO 44
<211> LENGTH: 840
<212> TYPE: DNA
<213> ORGANISM: Mus musculus

<400> SEQUENCE: 44
atggacaaga ttctgacagc atcatttta ctcctaggcc ttcacctagc tggggtgaat     60
ggccagcaga aggagaaaca tgaccagcag caggtgagac aaagtcccca atctctgaca    120
gtctgggaag gaggaaccac agttctgacc tgcagttatg aggacagcac tttaactac    180 ttcccatggt accaacagtt ccctggggaa ggccctgcac ttctgatatc catactttca    240
gtgtccgata aaaggaaga tggacgattc acaaccttct tcaataaaag ggagaaaaag     300
ctctccttgc acatcataga ctctcagcct ggagactcag ccacctactt ctgtgcagca    360
agtgggcttc tggaggaag caatgcaaag ctaaccttcg ggaaaggcac taaactctct     420
gttaaatcaa acatccagaa cccagaacct gctgtgtacc agttaaaaga tcctcggtct    480
caggacagca ccctctgcct gttcaccgac tttgactccc aaatcaatgt gccgaaaacc    540
atggaatctg gaacgttcat cactgacaaa actgtgctgg acatgaaagc tatggattcc    600
aagagcaatg gggccattgc ctggagcaac agacaagct tcacctgcca agatatcttc    660
aaagagacca cgccaccta ccccagttca gacgttccct gtgatgccac gttgactgag    720
aaaagctttg aaacagatat gaacctaaac tttcaaaacc tgtcagttat gggactccga    780
atcctcctgc tgaaagtagc cggatttaac ctgctcatga cgctgaggct gtggtccagt    840

<210> SEQ ID NO 45
<211> LENGTH: 17
<212> TYPE: PRT
<213> ORGANISM: Mus musculus

<400> SEQUENCE: 45

Cys Ala Ala Ser Gly Ala Ser Gly Gly Ser Asn Ala Lys Leu Thr Phe
1               5                   10                  15

Gly
```

```
<210> SEQ ID NO 46
<211> LENGTH: 153
<212> TYPE: PRT
<213> ORGANISM: Mus musculus

<400> SEQUENCE: 46

Met Asp Lys Ile Leu Thr Ala Ser Phe Leu Leu Leu Gly Leu His Leu
1               5                   10                  15

Ala Gly Val Asn Gly Gln Gln Lys Glu Lys His Asp Gln Gln Gln Val
            20                  25                  30

Arg Gln Ser Pro Gln Ser Leu Thr Val Trp Glu Gly Gly Thr Thr Val
        35                  40                  45

Leu Thr Cys Ser Tyr Glu Asp Ser Thr Phe Asn Tyr Phe Pro Trp Tyr
    50                  55                  60

Gln Gln Phe Pro Gly Glu Gly Pro Ala Leu Leu Ile Ser Ile Leu Ser
65                  70                  75                  80

Val Ser Asp Lys Lys Glu Asp Gly Arg Phe Thr Thr Phe Phe Asn Lys
                85                  90                  95

Arg Glu Lys Lys Leu Ser Leu His Ile Ile Asp Ser Gln Pro Gly Asp
            100                 105                 110

Ser Ala Thr Tyr Phe Cys Ala Ala Ser Gly Ala Ser Gly Gly Ser Asn
        115                 120                 125

Ala Lys Leu Thr Phe Gly Lys Gly Thr Lys Leu Ser Val Lys Ser Asn
    130                 135                 140

Ile Gln Asn Pro Glu Pro Ala Val Tyr
145                 150

<210> SEQ ID NO 47
<211> LENGTH: 280
<212> TYPE: PRT
<213> ORGANISM: Mus musculus

<400> SEQUENCE: 47

Met Asp Lys Ile Leu Thr Ala Ser Phe Leu Leu Leu Gly Leu His Leu
1               5                   10                  15

Ala Gly Val Asn Gly Gln Gln Lys Glu Lys His Asp Gln Gln Gln Val
            20                  25                  30

Arg Gln Ser Pro Gln Ser Leu Thr Val Trp Glu Gly Gly Thr Thr Val
        35                  40                  45

Leu Thr Cys Ser Tyr Glu Asp Ser Thr Phe Asn Tyr Phe Pro Trp Tyr
    50                  55                  60

Gln Gln Phe Pro Gly Glu Gly Pro Ala Leu Leu Ile Ser Ile Leu Ser
65                  70                  75                  80

Val Ser Asp Lys Lys Glu Asp Gly Arg Phe Thr Thr Phe Phe Asn Lys
                85                  90                  95

Arg Glu Lys Lys Leu Ser Leu His Ile Ile Asp Ser Gln Pro Gly Asp
            100                 105                 110

Ser Ala Thr Tyr Phe Cys Ala Ala Ser Gly Ala Ser Gly Gly Ser Asn
        115                 120                 125

Ala Lys Leu Thr Phe Gly Lys Gly Thr Lys Leu Ser Val Lys Ser Asn
    130                 135                 140

Ile Gln Asn Pro Glu Pro Ala Val Tyr Gln Leu Lys Asp Pro Arg Ser
145                 150                 155                 160

Gln Asp Ser Thr Leu Cys Leu Phe Thr Asp Phe Asp Ser Gln Ile Asn
                165                 170                 175
```

```
Val Pro Lys Thr Met Glu Ser Gly Thr Phe Ile Thr Asp Lys Thr Val
            180                 185                 190
Leu Asp Met Lys Ala Met Asp Ser Lys Ser Asn Gly Ala Ile Ala Trp
        195                 200                 205
Ser Asn Gln Thr Ser Phe Thr Cys Gln Asp Ile Phe Lys Glu Thr Asn
    210                 215                 220
Ala Thr Tyr Pro Ser Ser Asp Val Pro Cys Asp Ala Thr Leu Thr Glu
225                 230                 235                 240
Lys Ser Phe Glu Thr Asp Met Asn Leu Asn Phe Gln Asn Leu Ser Val
                245                 250                 255
Met Gly Leu Arg Ile Leu Leu Leu Lys Val Ala Gly Phe Asn Leu Leu
            260                 265                 270
Met Thr Leu Arg Leu Trp Ser Ser
        275                 280

<210> SEQ ID NO 48
<211> LENGTH: 39
<212> TYPE: DNA
<213> ORGANISM: Mus musculus

<400> SEQUENCE: 48
tgtgccagct ctctcggagg atgggctgag cagttcttc                              39

<210> SEQ ID NO 49
<211> LENGTH: 402
<212> TYPE: DNA
<213> ORGANISM: Mus musculus

<400> SEQUENCE: 49
atgtctaaca ctgtcctcgc tgattctgcc tggggcatca ccctgctatc ttgggttact       60
gtctttctct tgggaacaag ttcagcagat tctggggttg tccagtctcc aagacacata     120
atcaaagaaa agggaggaag gtccgttctg acgtgtattc ccatctctgg acatagcaat     180
gtggtctggt accagcagac tctggggaag gaattaaagt tccttattca gcattatgaa     240
aaggtggaga gagacaaagg attcctaccc agcagattct cagtccaaca gtttgatgac     300
tatcactctg aaatgaacat gagtgccttg gaactggagg actctgctat gtacttctgt     360
gccagctctc tcggaggatg ggctgagcag ttcttcggac ca                        402

<210> SEQ ID NO 50
<211> LENGTH: 945
<212> TYPE: DNA
<213> ORGANISM: Mus musculus

<400> SEQUENCE: 50
atgtctaaca ctgtcctcgc tgattctgcc tggggcatca ccctgctatc ttgggttact       60
gtctttctct tgggaacaag ttcagcagat tctggggttg tccagtctcc aagacacata     120
atcaaagaaa agggaggaag gtccgttctg acgtgtattc ccatctctgg acatagcaat     180
gtggtctggt accagcagac tctggggaag gaattaaagt tccttattca gcattatgaa     240
aaggtggaga gagacaaagg attcctaccc agcagattct cagtccaaca gtttgatgac     300
tatcactctg aaatgaacat gagtgccttg gaactggagg actctgctat gtacttctgt     360
gccagctctc tcggaggatg ggctgagcag ttcttcggac agggacacg actcaccgtc      420 ctagaggatc tgagaaatgt gactccaccc aaggtctcct tgtttgagcc atcaaaagca     480
gagattgcaa acaaacaaaa ggctaccctc gtgtgcttgg ccaggggctt cttccctgac     540
cacgtggagc tgagctggtg ggtgaatggc aaggaggtcc acagtggggt cagcacggac     600
```

-continued

```
cctcaggcct acaaggagag caattatagc tactgcctga gcagccgcct gagggtctct    660
gctaccttct ggcacaatcc tcgaaaccac ttccgctgcc aagtgcagtt ccatgggctt    720
tcagaggagg acaagtggcc agagggctca cccaaacctg tcacacagaa catcagtgca    780
gaggcctggg gccgagcaga ctgtggaatc acttcagcat cctatcatca ggggttctg    840 tctgcaacca tcctctatga gatcctactg gggaaggcca ccctatatgc tgtgctggtc    900
agtggcctgt tgctgatggc catggtcaag aaaaaaaatt cctga                    945
```

<210> SEQ ID NO 51
<211> LENGTH: 13
<212> TYPE: PRT
<213> ORGANISM: Mus musculus

<400> SEQUENCE: 51

Cys Ala Ser Ser Leu Gly Gly Trp Ala Glu Gln Phe Phe
1               5                   10

<210> SEQ ID NO 52
<211> LENGTH: 136
<212> TYPE: PRT
<213> ORGANISM: Mus musculus

<400> SEQUENCE: 52

Met Ser Asn Thr Val Leu Ala Asp Ser Ala Trp Gly Ile Thr Leu Leu
1               5                   10                  15

Ser Trp Val Thr Val Phe Leu Leu Gly Thr Ser Ser Ala Asp Ser Gly
                20                  25                  30

Val Val Gln Ser Pro Arg His Ile Ile Lys Glu Lys Gly Gly Arg Ser
            35                  40                  45

Val Leu Thr Cys Ile Pro Ile Ser Gly His Ser Asn Val Val Trp Tyr
        50                  55                  60

Gln Gln Thr Leu Gly Lys Glu Leu Lys Phe Leu Ile Gln His Tyr Glu
65                  70                  75                  80

Lys Val Glu Arg Asp Lys Gly Phe Leu Pro Ser Arg Phe Ser Val Gln
                85                  90                  95

Gln Phe Asp Asp Tyr His Ser Glu Met Asn Met Ser Ala Leu Glu Leu
            100                 105                 110

Glu Asp Ser Ala Met Tyr Phe Cys Ala Ser Ser Leu Gly Gly Trp Ala
        115                 120                 125

Glu Gln Phe Phe Gly Pro Gly Thr
    130                 135

<210> SEQ ID NO 53
<211> LENGTH: 314
<212> TYPE: PRT
<213> ORGANISM: Homo sapiens

<400> SEQUENCE: 53

Met Ser Asn Thr Val Leu Ala Asp Ser Ala Trp Gly Ile Thr Leu Leu
1               5                   10                  15

Ser Trp Val Thr Val Phe Leu Leu Gly Thr Ser Ser Ala Asp Ser Gly
                20                  25                  30

Val Val Gln Ser Pro Arg His Ile Ile Lys Glu Lys Gly Gly Arg Ser
            35                  40                  45

Val Leu Thr Cys Ile Pro Ile Ser Gly His Ser Asn Val Val Trp Tyr
        50                  55                  60

Gln Gln Thr Leu Gly Lys Glu Leu Lys Phe Leu Ile Gln His Tyr Glu

```
                65                  70                  75                  80
Lys Val Glu Arg Asp Lys Gly Phe Leu Pro Ser Arg Phe Ser Val Gln
                    85                  90                  95

Gln Phe Asp Asp Tyr His Ser Glu Met Asn Met Ser Ala Leu Glu Leu
                100                 105                 110

Glu Asp Ser Ala Met Tyr Phe Cys Ala Ser Ser Leu Gly Gly Trp Ala
                115                 120                 125

Glu Gln Phe Phe Gly Pro Gly Thr Arg Leu Thr Val Leu Glu Asp Leu
                130                 135                 140

Arg Asn Val Thr Pro Pro Lys Val Ser Leu Phe Glu Pro Ser Lys Ala
145                 150                 155                 160

Glu Ile Ala Asn Lys Gln Lys Ala Thr Leu Val Cys Leu Ala Arg Gly
                165                 170                 175

Phe Phe Pro Asp His Val Glu Leu Ser Trp Trp Val Asn Gly Lys Glu
                180                 185                 190

Val His Ser Gly Val Ser Thr Asp Pro Gln Ala Tyr Lys Glu Ser Asn
                195                 200                 205

Tyr Ser Tyr Cys Leu Ser Ser Arg Leu Arg Val Ser Ala Thr Phe Trp
210                 215                 220

His Asn Pro Arg Asn His Phe Arg Cys Gln Val Gln Phe His Gly Leu
225                 230                 235                 240

Ser Glu Glu Asp Lys Trp Pro Glu Gly Ser Pro Lys Pro Val Thr Gln
                245                 250                 255

Asn Ile Ser Ala Glu Ala Trp Gly Arg Ala Asp Cys Gly Ile Thr Ser
                260                 265                 270

Ala Ser Tyr His Gln Gly Val Leu Ser Ala Thr Ile Leu Tyr Glu Ile
                275                 280                 285

Leu Leu Gly Lys Ala Thr Leu Tyr Ala Val Leu Val Ser Gly Leu Val
                290                 295                 300

Leu Met Ala Met Val Lys Lys Lys Asn Ser
305                 310

<210> SEQ ID NO 54
<211> LENGTH: 9
<212> TYPE: PRT
<213> ORGANISM: Homo sapiens

<400> SEQUENCE: 54

Ser Phe Ala Cys Leu Lys Glu Leu Tyr
1               5

<210> SEQ ID NO 55
<211> LENGTH: 9
<212> TYPE: PRT
<213> ORGANISM: Homo sapiens

<400> SEQUENCE: 55

Glu Ile Asp Glu Gln Arg Thr Lys Tyr
1               5

<210> SEQ ID NO 56
<211> LENGTH: 9
<212> TYPE: PRT
<213> ORGANISM: Homo sapiens

<400> SEQUENCE: 56

Ser Ser Pro Thr Thr Pro Pro Glu Tyr
1               5
```

<210> SEQ ID NO 57
<211> LENGTH: 9
<212> TYPE: PRT
<213> ORGANISM: Homo sapiens

<400> SEQUENCE: 57

Asp Thr Gln Tyr Ser Ala Leu Lys Val
1               5

<210> SEQ ID NO 58
<211> LENGTH: 9
<212> TYPE: PRT
<213> ORGANISM: Homo sapiens

<400> SEQUENCE: 58

Leu Ser Leu Thr Glu Thr Ile Glu Cys
1               5

<210> SEQ ID NO 59
<211> LENGTH: 9
<212> TYPE: PRT
<213> ORGANISM: Homo sapiens

<400> SEQUENCE: 59

Gln Ser Leu Leu Glu Glu Met Phe Leu
1               5

<210> SEQ ID NO 60
<211> LENGTH: 9
<212> TYPE: PRT
<213> ORGANISM: Homo sapiens

<400> SEQUENCE: 60

Leu Lys Ser Ser Gly Gln Gly Arg Arg
1               5

<210> SEQ ID NO 61
<211> LENGTH: 9
<212> TYPE: PRT
<213> ORGANISM: Homo sapiens

<400> SEQUENCE: 61

Gln Ala Gln Leu Ser Leu Glu Arg Gln
1               5

<210> SEQ ID NO 62
<211> LENGTH: 9
<212> TYPE: PRT
<213> ORGANISM: Homo sapiens

<400> SEQUENCE: 62

Thr Met Glu Glu Glu Tyr Gly Leu Val
1               5

<210> SEQ ID NO 63
<211> LENGTH: 9
<212> TYPE: PRT
<213> ORGANISM: Homo sapiens

<400> SEQUENCE: 63

Ser Gln Val Glu Glu Leu Lys Ser Ser
1               5

<210> SEQ ID NO 64
<211> LENGTH: 9

```
<212> TYPE: PRT
<213> ORGANISM: Homo sapiens

<400> SEQUENCE: 64

Glu Met Phe Leu Thr Val Pro Glu Ser
1               5

<210> SEQ ID NO 65
<211> LENGTH: 9
<212> TYPE: PRT
<213> ORGANISM: Homo sapiens

<400> SEQUENCE: 65

Leu Ser Leu Glu Arg Gln Lys Arg Val
1               5

<210> SEQ ID NO 66
<211> LENGTH: 9
<212> TYPE: PRT
<213> ORGANISM: Homo sapiens

<400> SEQUENCE: 66

Glu Leu Tyr Asp Leu Arg Gln His Phe
1               5

<210> SEQ ID NO 67
<211> LENGTH: 9
<212> TYPE: PRT
<213> ORGANISM: Homo sapiens

<400> SEQUENCE: 67

Cys Ile Arg Arg Ala Lys Ala Val Lys
1               5

<210> SEQ ID NO 68
<211> LENGTH: 9
<212> TYPE: PRT
<213> ORGANISM: Homo sapiens

<400> SEQUENCE: 68

Val Gln Thr Ser Arg Ala Ala Ala Lys
1               5

<210> SEQ ID NO 69
<211> LENGTH: 9
<212> TYPE: PRT
<213> ORGANISM: Homo sapiens

<400> SEQUENCE: 69

Thr Gln Tyr Ser Ala Leu Lys Val Lys
1               5

<210> SEQ ID NO 70
<211> LENGTH: 9
<212> TYPE: PRT
<213> ORGANISM: Homo sapiens

<400> SEQUENCE: 70

Gly Gln Gly Arg Arg Ser Pro Gly Lys
1               5

<210> SEQ ID NO 71
<211> LENGTH: 9
<212> TYPE: PRT
<213> ORGANISM: Homo sapiens
```

```
<400> SEQUENCE: 71

Lys Glu Ile Phe Ser Cys Ile Lys Lys
1               5

<210> SEQ ID NO 72
<211> LENGTH: 9
<212> TYPE: PRT
<213> ORGANISM: Homo sapiens

<400> SEQUENCE: 72

Glu Ser His Arg Lys Pro Leu Lys Arg
1               5

<210> SEQ ID NO 73
<211> LENGTH: 9
<212> TYPE: PRT
<213> ORGANISM: Homo sapiens

<400> SEQUENCE: 73

Arg Gln Met Asn Glu Gln His Ala Lys
1               5

<210> SEQ ID NO 74
<211> LENGTH: 9
<212> TYPE: PRT
<213> ORGANISM: Homo sapiens

<400> SEQUENCE: 74

Ser Leu Ala Gly Ser Asp Ile Val Lys
1               5

<210> SEQ ID NO 75
<211> LENGTH: 9
<212> TYPE: PRT
<213> ORGANISM: Homo sapiens

<400> SEQUENCE: 75

Leu Thr Val Pro Glu Ser His Arg Lys
1               5

<210> SEQ ID NO 76
<211> LENGTH: 9
<212> TYPE: PRT
<213> ORGANISM: Homo sapiens

<400> SEQUENCE: 76

Gln Leu Gly Ala Thr Gly Ala Tyr Arg
1               5

<210> SEQ ID NO 77
<211> LENGTH: 9
<212> TYPE: PRT
<213> ORGANISM: Homo sapiens

<400> SEQUENCE: 77

Pro Ala Pro Ser Phe Ala Cys Leu Lys
1               5

<210> SEQ ID NO 78
<211> LENGTH: 9
<212> TYPE: PRT
<213> ORGANISM: Homo sapiens

<400> SEQUENCE: 78

Leu Gln Ala Gln Leu Ser Leu Glu Arg
```

1               5

<210> SEQ ID NO 79
<211> LENGTH: 9
<212> TYPE: PRT
<213> ORGANISM: Homo sapiens

<400> SEQUENCE: 79

Leu Gln Leu Ala Ala Glu Leu Gly Lys
1               5

<210> SEQ ID NO 80
<211> LENGTH: 9
<212> TYPE: PRT
<213> ORGANISM: Homo sapiens

<400> SEQUENCE: 80

Ala Gln Leu Ser Leu Glu Arg Gln Lys
1               5

<210> SEQ ID NO 81
<211> LENGTH: 9
<212> TYPE: PRT
<213> ORGANISM: Homo sapiens

<400> SEQUENCE: 81

His Pro Phe Val Asn Gly Val Glu Lys
1               5

<210> SEQ ID NO 82
<211> LENGTH: 9
<212> TYPE: PRT
<213> ORGANISM: Homo sapiens

<400> SEQUENCE: 82

Val Tyr Asp His Val Phe Ala Glu Lys
1               5

<210> SEQ ID NO 83
<211> LENGTH: 9
<212> TYPE: PRT
<213> ORGANISM: Homo sapiens

<400> SEQUENCE: 83

Lys Val Lys Tyr Glu Glu Leu Leu Lys
1               5

<210> SEQ ID NO 84
<211> LENGTH: 9
<212> TYPE: PRT
<213> ORGANISM: Homo sapiens

<400> SEQUENCE: 84

Ser Pro Thr Thr Pro Pro Glu Tyr Lys
1               5

<210> SEQ ID NO 85
<211> LENGTH: 9
<212> TYPE: PRT
<213> ORGANISM: Homo sapiens

<400> SEQUENCE: 85

Leu Gln Ser Gln Val Glu Glu Leu Lys
1               5

```
<210> SEQ ID NO 86
<211> LENGTH: 9
<212> TYPE: PRT
<213> ORGANISM: Homo sapiens

<400> SEQUENCE: 86

Lys Gln Arg Gly Ile Ser Leu Leu His
1               5

<210> SEQ ID NO 87
<211> LENGTH: 9
<212> TYPE: PRT
<213> ORGANISM: Homo sapiens

<400> SEQUENCE: 87

Ile Phe Ser Cys Ile Lys Lys Thr Lys
1               5

<210> SEQ ID NO 88
<211> LENGTH: 9
<212> TYPE: PRT
<213> ORGANISM: Homo sapiens

<400> SEQUENCE: 88

Pro Asp Ser Leu Tyr Val Pro Phe Lys
1               5

<210> SEQ ID NO 89
<211> LENGTH: 9
<212> TYPE: PRT
<213> ORGANISM: Homo sapiens

<400> SEQUENCE: 89

Ser Gly Trp Glu Leu Ala Ser Val Asn
1               5

<210> SEQ ID NO 90
<211> LENGTH: 9
<212> TYPE: PRT
<213> ORGANISM: Homo sapiens

<400> SEQUENCE: 90

Pro Pro Glu Tyr Lys Ala Leu Phe Lys
1               5

<210> SEQ ID NO 91
<211> LENGTH: 9
<212> TYPE: PRT
<213> ORGANISM: Homo sapiens

<400> SEQUENCE: 91

Gly Ala Thr Gly Ala Tyr Arg Ala Arg
1               5

<210> SEQ ID NO 92
<211> LENGTH: 9
<212> TYPE: PRT
<213> ORGANISM: Homo sapiens

<400> SEQUENCE: 92

Ala Asp Ser Lys Ala Ser Gln Gln Lys
1               5

<210> SEQ ID NO 93
<211> LENGTH: 9
<212> TYPE: PRT
```

<213> ORGANISM: Homo sapiens

<400> SEQUENCE: 93

Leu Gln Glu Ile Glu Tyr Leu Thr Lys
1               5

<210> SEQ ID NO 94
<211> LENGTH: 9
<212> TYPE: PRT
<213> ORGANISM: Homo sapiens

<400> SEQUENCE: 94

Ala Tyr Arg Ala Arg Ala Leu Glu Leu
1               5

<210> SEQ ID NO 95
<211> LENGTH: 9
<212> TYPE: PRT
<213> ORGANISM: Homo sapiens

<400> SEQUENCE: 95

Leu Phe Lys Glu Ile Phe Ser Cys Ile
1               5

<210> SEQ ID NO 96
<211> LENGTH: 9
<212> TYPE: PRT
<213> ORGANISM: Homo sapiens

<400> SEQUENCE: 96

Glu Tyr Lys Ala Leu Phe Lys Glu Ile
1               5

<210> SEQ ID NO 97
<211> LENGTH: 9
<212> TYPE: PRT
<213> ORGANISM: Homo sapiens

<400> SEQUENCE: 97

Pro Phe Lys Glu Pro Ser Gln Ser Leu
1               5

<210> SEQ ID NO 98
<211> LENGTH: 9
<212> TYPE: PRT
<213> ORGANISM: Homo sapiens

<400> SEQUENCE: 98

Glu Tyr Leu Thr Lys Gln Val Glu Leu
1               5

<210> SEQ ID NO 99
<211> LENGTH: 9
<212> TYPE: PRT
<213> ORGANISM: Homo sapiens

<400> SEQUENCE: 99

Met Tyr Thr Thr Asn Gln Glu Gln Leu
1               5

<210> SEQ ID NO 100
<211> LENGTH: 9
<212> TYPE: PRT
<213> ORGANISM: Homo sapiens

<400> SEQUENCE: 100

```
Tyr Lys Ala Leu Phe Lys Glu Ile Phe
1               5
```

<210> SEQ ID NO 101
<211> LENGTH: 9
<212> TYPE: PRT
<213> ORGANISM: Homo sapiens

<400> SEQUENCE: 101

```
Pro Phe Val Asn Gly Val Glu Lys Leu
1               5
```

<210> SEQ ID NO 102
<211> LENGTH: 9
<212> TYPE: PRT
<213> ORGANISM: Homo sapiens

<400> SEQUENCE: 102

```
Lys Gln Arg Gly Ile Ser Leu Leu His
1               5
```

<210> SEQ ID NO 103
<211> LENGTH: 9
<212> TYPE: PRT
<213> ORGANISM: Homo sapiens

<400> SEQUENCE: 103

```
Val Lys Gln Arg Gly Ile Ser Leu Leu
1               5
```

<210> SEQ ID NO 104
<211> LENGTH: 9
<212> TYPE: PRT
<213> ORGANISM: Homo sapiens

<400> SEQUENCE: 104

```
Ser Phe Ala Cys Leu Lys Glu Leu Tyr
1               5
```

<210> SEQ ID NO 105
<211> LENGTH: 9
<212> TYPE: PRT
<213> ORGANISM: Homo sapiens

<400> SEQUENCE: 105

```
Glu Gln Leu Gln Glu Ile Glu Tyr Leu
1               5
```

<210> SEQ ID NO 106
<211> LENGTH: 9
<212> TYPE: PRT
<213> ORGANISM: Homo sapiens

<400> SEQUENCE: 106

```
Ala Val Lys Gln Arg Gly Ile Ser Leu
1               5
```

<210> SEQ ID NO 107
<211> LENGTH: 9
<212> TYPE: PRT
<213> ORGANISM: Homo sapiens

<400> SEQUENCE: 107

```
Val Pro Asp Ser Leu Tyr Val Pro Phe
1               5
```

<210> SEQ ID NO 108
<211> LENGTH: 9
<212> TYPE: PRT
<213> ORGANISM: Homo sapiens

<400> SEQUENCE: 108

Gln Tyr Ser Ala Leu Lys Val Lys Tyr
1               5

<210> SEQ ID NO 109
<211> LENGTH: 9
<212> TYPE: PRT
<213> ORGANISM: Homo sapiens

<400> SEQUENCE: 109

Gln His Phe Val Tyr Asp His Val Phe
1               5

<210> SEQ ID NO 110
<211> LENGTH: 9
<212> TYPE: PRT
<213> ORGANISM: Homo sapiens

<400> SEQUENCE: 110

Glu Leu Tyr Asp Leu Arg Gln His Phe
1               5

<210> SEQ ID NO 111
<211> LENGTH: 9
<212> TYPE: PRT
<213> ORGANISM: Homo sapiens

<400> SEQUENCE: 111

Val Glu Lys Leu Val Pro Asp Ser Leu
1               5

<210> SEQ ID NO 112
<211> LENGTH: 9
<212> TYPE: PRT
<213> ORGANISM: Homo sapiens

<400> SEQUENCE: 112

Tyr Asp His Val Phe Ala Glu Lys Ile
1               5

<210> SEQ ID NO 113
<211> LENGTH: 9
<212> TYPE: PRT
<213> ORGANISM: Homo sapiens

<400> SEQUENCE: 113

Thr Pro Pro Glu Tyr Lys Ala Leu Phe
1               5

<210> SEQ ID NO 114
<211> LENGTH: 9
<212> TYPE: PRT
<213> ORGANISM: Homo sapiens

<400> SEQUENCE: 114

Gln Met Leu Gln Ser Glu His Pro Phe
1               5

<210> SEQ ID NO 115

```
<211> LENGTH: 9
<212> TYPE: PRT
<213> ORGANISM: Homo sapiens

<400> SEQUENCE: 115

Ser Ser Leu Ala Gly Ser Asp Ile Val
1               5

<210> SEQ ID NO 116
<211> LENGTH: 9
<212> TYPE: PRT
<213> ORGANISM: Homo sapiens

<400> SEQUENCE: 116

Thr Leu Leu Asp Arg Asn Thr Glu Leu
1               5

<210> SEQ ID NO 117
<211> LENGTH: 9
<212> TYPE: PRT
<213> ORGANISM: Homo sapiens

<400> SEQUENCE: 117

Thr Val Thr Met Leu Gln Ala Gln Leu
1               5

<210> SEQ ID NO 118
<211> LENGTH: 9
<212> TYPE: PRT
<213> ORGANISM: Homo sapiens

<400> SEQUENCE: 118

Gln His Ala Lys Val Tyr Glu Gln Leu
1               5

<210> SEQ ID NO 119
<211> LENGTH: 9
<212> TYPE: PRT
<213> ORGANISM: Homo sapiens

<400> SEQUENCE: 119

Ser Gln Ser Leu Leu Glu Glu Met Phe
1               5

<210> SEQ ID NO 120
<211> LENGTH: 9
<212> TYPE: PRT
<213> ORGANISM: Homo sapiens

<400> SEQUENCE: 120

Val Pro Glu Ser His Arg Lys Pro Leu
1               5

<210> SEQ ID NO 121
<211> LENGTH: 9
<212> TYPE: PRT
<213> ORGANISM: Homo sapiens

<400> SEQUENCE: 121

Lys Pro Ala Pro Ser Phe Ala Cys Leu
1               5

<210> SEQ ID NO 122
<211> LENGTH: 9
<212> TYPE: PRT
<213> ORGANISM: Homo sapiens
```

<400> SEQUENCE: 122

Ala Val Gln Thr Ser Arg Ala Ala Ala
1               5

<210> SEQ ID NO 123
<211> LENGTH: 9
<212> TYPE: PRT
<213> ORGANISM: Homo sapiens

<400> SEQUENCE: 123

Thr Gly Ala Tyr Arg Ala Arg Ala Leu
1               5

<210> SEQ ID NO 124
<211> LENGTH: 9
<212> TYPE: PRT
<213> ORGANISM: Homo sapiens

<400> SEQUENCE: 124

Arg Ala Arg Ala Leu Glu Leu Glu Ala
1               5

<210> SEQ ID NO 125
<211> LENGTH: 9
<212> TYPE: PRT
<213> ORGANISM: Homo sapiens

<400> SEQUENCE: 125

Glu Val Ala Glu Met Arg Gln Met Leu
1               5

<210> SEQ ID NO 126
<211> LENGTH: 9
<212> TYPE: PRT
<213> ORGANISM: Homo sapiens

<400> SEQUENCE: 126

Thr Ser Arg Ala Ala Ala Lys Asp Leu
1               5

<210> SEQ ID NO 127
<211> LENGTH: 9
<212> TYPE: PRT
<213> ORGANISM: Homo sapiens

<400> SEQUENCE: 127

Lys Gln Val Glu Leu Leu Arg Gln Met
1               5

<210> SEQ ID NO 128
<211> LENGTH: 9
<212> TYPE: PRT
<213> ORGANISM: Homo sapiens

<400> SEQUENCE: 128

Leu Ala Ala Glu Leu Gly Lys Thr Leu
1               5

<210> SEQ ID NO 129
<211> LENGTH: 9
<212> TYPE: PRT
<213> ORGANISM: Homo sapiens

<400> SEQUENCE: 129

```
Glu Asn Ser Glu Leu Glu Gln Gln Leu
1               5

<210> SEQ ID NO 130
<211> LENGTH: 9
<212> TYPE: PRT
<213> ORGANISM: Homo sapiens

<400> SEQUENCE: 130

Arg Thr Lys Tyr Arg Ser Leu Ser Ser
1               5

<210> SEQ ID NO 131
<211> LENGTH: 9
<212> TYPE: PRT
<213> ORGANISM: Homo sapiens

<400> SEQUENCE: 131

Glu Gln Arg Thr Lys Tyr Arg Ser Leu
1               5

<210> SEQ ID NO 132
<211> LENGTH: 9
<212> TYPE: PRT
<213> ORGANISM: Homo sapiens

<400> SEQUENCE: 132

Thr Gly Ala Tyr Arg Ala Arg Ala Leu
1               5

<210> SEQ ID NO 133
<211> LENGTH: 9
<212> TYPE: PRT
<213> ORGANISM: Homo sapiens

<400> SEQUENCE: 133

Glu His Leu Lys Lys Thr Val Thr Met
1               5

<210> SEQ ID NO 134
<211> LENGTH: 9
<212> TYPE: PRT
<213> ORGANISM: Homo sapiens

<400> SEQUENCE: 134

Cys Ile Lys Lys Thr Lys Gln Glu Ile
1               5

<210> SEQ ID NO 135
<211> LENGTH: 9
<212> TYPE: PRT
<213> ORGANISM: Homo sapiens

<400> SEQUENCE: 135

Leu Glu Arg Gln Lys Arg Val Thr Met
1               5

<210> SEQ ID NO 136
<211> LENGTH: 9
<212> TYPE: PRT
<213> ORGANISM: Homo sapiens

<400> SEQUENCE: 136

Gln Gln Leu Gly Ala Thr Gly Ala Tyr
1               5
```

<210> SEQ ID NO 137
<211> LENGTH: 9
<212> TYPE: PRT
<213> ORGANISM: Homo sapiens

<400> SEQUENCE: 137

Arg Ala Arg Ala Leu Glu Leu Glu Ala
1               5

<210> SEQ ID NO 138
<211> LENGTH: 9
<212> TYPE: PRT
<213> ORGANISM: Homo sapiens

<400> SEQUENCE: 138

Leu Leu Arg Gln Met Asn Glu Gln His
1               5

<210> SEQ ID NO 139
<211> LENGTH: 9
<212> TYPE: PRT
<213> ORGANISM: Homo sapiens

<400> SEQUENCE: 139

Tyr Asp Leu Arg Gln His Phe Val Tyr
1               5

<210> SEQ ID NO 140
<211> LENGTH: 9
<212> TYPE: PRT
<213> ORGANISM: Homo sapiens

<400> SEQUENCE: 140

Leu Gln Gln Asp Leu Gln Leu Ala Ala
1               5

<210> SEQ ID NO 141
<211> LENGTH: 9
<212> TYPE: PRT
<213> ORGANISM: Homo sapiens

<400> SEQUENCE: 141

Met Arg Gln Met Leu Gln Ser Glu His
1               5

<210> SEQ ID NO 142
<211> LENGTH: 9
<212> TYPE: PRT
<213> ORGANISM: Homo sapiens

<400> SEQUENCE: 142

Pro Ser Phe Ala Cys Leu Lys Glu Leu
1               5

<210> SEQ ID NO 143
<211> LENGTH: 9
<212> TYPE: PRT
<213> ORGANISM: Homo sapiens

<400> SEQUENCE: 143

Arg Gln Lys Arg Val Thr Met Glu Glu
1               5

<210> SEQ ID NO 144
<211> LENGTH: 9

```
<212> TYPE: PRT
<213> ORGANISM: Homo sapiens

<400> SEQUENCE: 144

Leu Thr Lys Gln Val Glu Leu Leu Arg
1               5

<210> SEQ ID NO 145
<211> LENGTH: 454
<212> TYPE: PRT
<213> ORGANISM: Homo sapiens

<400> SEQUENCE: 145

Met Leu Ala Glu Asn Leu Val Glu Glu Phe Glu Met Lys Glu Asp Glu
1               5                   10                  15

Pro Trp Tyr Asp His Gln Asp Leu Gln Gln Asp Leu Gln Leu Ala Ala
            20                  25                  30

Glu Leu Gly Lys Thr Leu Leu Asp Arg Asn Thr Glu Leu Glu Asp Ser
        35                  40                  45

Val Gln Gln Met Tyr Thr Thr Asn Gln Glu Gln Leu Gln Glu Ile Glu
    50                  55                  60

Tyr Leu Thr Lys Gln Val Glu Leu Leu Arg Gln Met Asn Glu Gln His
65                  70                  75                  80

Ala Lys Val Tyr Glu Gln Leu Asp Val Thr Ala Arg Glu Leu Glu Glu
                85                  90                  95

Thr Asn Gln Lys Leu Val Ala Asp Ser Lys Ala Ser Gln Gln Lys Ile
            100                 105                 110

Leu Ser Leu Thr Glu Thr Ile Glu Cys Leu Gln Thr Asn Ile Asp His
        115                 120                 125

Leu Gln Ser Gln Val Glu Leu Lys Ser Ser Gly Gln Gly Arg Arg
    130                 135                 140

Ser Pro Gly Lys Cys Asp Gln Glu Lys Pro Ala Pro Ser Phe Ala Cys
145                 150                 155                 160

Leu Lys Glu Leu Tyr Asp Leu Arg Gln His Phe Val Tyr Asp His Val
                165                 170                 175

Phe Ala Glu Lys Ile Thr Ser Leu Gln Gly Gln Pro Ser Pro Asp Glu
            180                 185                 190

Glu Glu Asn Glu His Leu Lys Lys Thr Val Thr Met Leu Gln Ala Gln
        195                 200                 205

Leu Ser Leu Glu Arg Gln Lys Arg Val Thr Met Glu Glu Tyr Gly
    210                 215                 220

Leu Val Leu Lys Glu Asn Ser Glu Leu Glu Gln Gln Leu Gly Ala Thr
225                 230                 235                 240

Gly Ala Tyr Arg Ala Arg Ala Leu Glu Leu Glu Ala Glu Val Ala Glu
                245                 250                 255

Met Arg Gln Met Leu Gln Ser Glu His Pro Phe Val Asn Gly Val Glu
            260                 265                 270

Lys Leu Val Pro Asp Ser Leu Tyr Val Pro Phe Lys Glu Pro Ser Gln
        275                 280                 285

Ser Leu Leu Glu Glu Met Phe Leu Thr Val Pro Glu Ser His Arg Lys
    290                 295                 300

Pro Leu Lys Arg Ser Ser Ser Thr Ile Leu Ser Leu Ala Gly
305                 310                 315                 320

Ser Asp Ile Val Lys Gly His Glu Glu Thr Cys Ile Arg Arg Ala Lys
                325                 330                 335

Ala Val Lys Gln Arg Gly Ile Ser Leu Leu His Glu Val Asp Thr Gln
```

-continued

```
                 340                 345                 350
    Tyr Ser Ala Leu Lys Val Lys Tyr Glu Glu Leu Leu Lys Lys Cys Gln
            355                 360                 365

Glu Glu Gln Asp Ser Leu Ser His Lys Ala Val Gln Thr Ser Arg Ala
            370                 375                 380

Ala Ala Lys Asp Leu Thr Gly Val Asn Ala Gln Ser Glu Pro Val Ala
    385                 390                 395                 400

Ser Gly Trp Glu Leu Ala Ser Val Asn Pro Glu Pro Val Ser Ser Pro
                    405                 410                 415

Thr Thr Pro Pro Glu Tyr Lys Ala Leu Phe Lys Glu Ile Phe Ser Cys
                420                 425                 430

Ile Lys Lys Thr Lys Gln Glu Ile Asp Glu Gln Arg Thr Lys Tyr Arg
            435                 440                 445

Ser Leu Ser Ser His Ser
            450

<210> SEQ ID NO 146
<211> LENGTH: 9
<212> TYPE: PRT
<213> ORGANISM: Homo sapiens

<400> SEQUENCE: 146

Arg Ile Ile Thr Ser Arg Ile Leu Val
1               5

<210> SEQ ID NO 147
<211> LENGTH: 9
<212> TYPE: PRT
<213> ORGANISM: Homo sapiens

<400> SEQUENCE: 147

Asn Leu Tyr Val Ser Gly Leu Pro Lys
1               5
```